US005685821A

United States Patent [19]

Pike

[11] Patent Number: 5,685,821
[45] Date of Patent: Nov. 11, 1997

[54] METHOD AND APPARATUS FOR PERFORMING ENDOSCOPIC SURGICAL PROCEDURES

[75] Inventor: Harold Levon Pike, Castle Rock, Colo.

[73] Assignee: Arthrotek, Warsaw, Ind.

[21] Appl. No.: 659,773

[22] Filed: May 6, 1996

Related U.S. Application Data

[63] Continuation of Ser. No. 963,448, Oct. 19, 1992, abandoned.

[51] Int. Cl.$^6$ ............................................. A61B 1/015
[52] U.S. Cl. .............................. 600/118; 600/156; 604/35
[58] Field of Search .......................... 604/30–35, 65–67; 600/118, 156–159

[56] References Cited

U.S. PATENT DOCUMENTS

| | | |
|---|---|---|
| 3,900,022 | 8/1975 | Widran. |
| 4,007,742 | 2/1977 | Banko. |
| 4,180,074 | 12/1979 | Murry et al.. |
| 4,203,444 | 5/1980 | Bonnell et al.. |
| 4,261,360 | 4/1981 | Perez. |
| 4,343,300 | 8/1982 | Hattori ............................ 128/6 |
| 4,349,014 | 9/1982 | Takamatsu ....................... 128/6 |
| 4,423,727 | 1/1984 | Widran et al.. |
| 4,493,694 | 1/1985 | Wuchinich. |
| 4,493,695 | 1/1985 | Cook. |
| 4,604,089 | 8/1986 | Santangelo et al.. |
| 4,650,462 | 3/1987 | DeSatnick et al.. |
| 4,662,871 | 5/1987 | Rafelson. |
| 4,671,792 | 6/1987 | Borsanyi. |
| 4,750,902 | 6/1988 | Wuchinich et al.. |
| 4,795,424 | 1/1989 | Burner. |
| 4,798,580 | 1/1989 | DeMeo et al.. |
| 4,862,872 | 9/1989 | Yabe et al. ........................ 128/6 |
| 4,902,277 | 2/1990 | Mathies et al.. |
| 4,920,413 | 4/1990 | Nakamura et al. ............... 128/6 |
| 4,947,245 | 8/1990 | Ogawa et al. .................... 128/6 |
| 4,996,975 | 3/1991 | Nakamura ........................ 128/6 |
| 5,000,733 | 3/1991 | Mathies et al.. |
| 5,022,382 | 6/1991 | Ohshoji et al. ................... 128/4 |
| 5,152,746 | 10/1992 | Atkinson et al. ................ 604/33 |
| 5,195,960 | 3/1993 | Hossain et al.. |
| 5,213,571 | 5/1993 | Fujio et al. ...................... 604/31 |
| 5,254,087 | 10/1993 | McEwen ......................... 604/66 |
| 5,267,956 | 12/1993 | Beuchat. |
| 5,269,289 | 12/1993 | Takehana et al. ................ 128/4 |
| 5,313,936 | 5/1994 | Miyazaki et al.. |
| 5,391,144 | 2/1995 | Sakurai et al. .................. 128/6 |

FOREIGN PATENT DOCUMENTS

| | | |
|---|---|---|
| 8400258 | 1/1986 | WIPO. |
| 8500233 | 3/1986 | WIPO. |
| 9200803 | 6/1992 | WIPO. |

OTHER PUBLICATIONS

Dolk, et al., "Three Irrigation Systems for Motorized Arthroscopic Surggery: A Comparative Experimental and Clinical Study", The Journal of Arthroscopic and Related Surgery, vol. 5, No. 4, 1989.

Dolk, et al., "Elevated Position of Suction Outflow During Arthroscopic Motorized Surgery: An Experimental Study", The Journal of Arthroscopic and Related Surgery, vol. 5, No. 4, 1989.

Dolk, et al., "Elevated Position of the Irrigation Outflow During Arthroscopy: An Experimental Study", The Journal of Arthroscopic and Related Surgery, vol. 5, No. 2, 1989.

*Primary Examiner*—Mark Bockelman
*Attorney, Agent, or Firm*—Harness, Dickey & Pierce, P.L.C.

[57] ABSTRACT

An apparatus for performing endoscopic surgical procedures within an internal body cavity. The apparatus includes an imaging unit for viewing the internal body cavity. In addition, the apparatus includes an intra-articular unit for providing a flow of fluid into the internal body cavity as well as for controllably withdrawing fluid from the internal body cavity. The apparatus further includes a cart which allows electrical intercommunication between the imaging unit and the intra-articular unit whereby the operation of the imaging unit and the intra-articular unit are interdependent.

20 Claims, 12 Drawing Sheets

METHOD AND APPARATUS FOR PERFORMING ENDOSCOPIC SURGICAL PROCEDURES

This is a continuation of U.S. patent application Ser. No. 07/963,448, filed Oct. 19, 1992, which has been expressly abandoned.

FIELD OF THE INVENTION

The present invention relates to a method and apparatus for use in surgical procedures, and more particularly to a method and apparatus for use in endoscopic surgical procedures.

BACKGROUND OF THE INVENTION

Endoscopic surgery is a minimally invasive therapeutic and/or diagnostic procedure during which relatively small visualization and surgical tools are introduced into a portion of the human body such as a knee joint through relatively small incisions. Typically, at least three incisions are employed for a therapeutic procedure and at least two are employed for a diagnostic procedure. During endoscopic surgery, physiological fluid such as a sterile saline solution is allowed to flow through the joint so as to distend the joint to facilitate access to the joint. In addition, the flow of physiological fluid through the joint enhances the clarity of the field of view by removing debris from the surgical site.

The flow of fluid into the joint during endoscopic surgery is regulated by two independent but yet related functions. These two functions are the pressure of fluid within the joint and the volume of fluid flowing through the joint. The pressure of fluid within the joint determines the extent to which the joint is distended. For example, a surgeon may want to increase the pressure of fluid within the joint when the surgeon needs to view or access the end of the joint opposite to the point of insertion of the probe. In contrast, if there is bleeding or debris in the cavity, an increase in the flow rate of fluid is needed to clear the field of view. In addition, when an instrument such as a shaver with a suction tube is used, a greater flow of fluid into the cavity is required to prevent the cavity from collapsing.

Various methods are known to control the pressure and flow rate of fluid during endoscopic surgery. These methods range from certain manual methods, such as manually adjusting the height of fluid supply bags to increase pressure while maintaining flow rates using variable clamps on the tubing leading to and away from the patient, to automatic fluid control systems. Some of these automatic fluid control systems regulate flow rate in response to the sensed pressure corresponding to the pressure within the cavity. Other automatic fluid control systems attempt to maintain a constant volume of fluid flowing into the cavity and therefore a constant pressure within the joint by balancing the inflow and outflow of the physiological fluid into the cavity. Still other of these automatic fluid control systems allow for independent control of the flow rate and the pressure, allowing the system to operate at a specified number of fixed flow rates and fixed pressures.

The equipment used for endoscopic surgery in the past been relatively difficult to use. For example, a nurse generally has to connect individual tubes to various cannulas and pumps associated with the system as well as to thread tubes through peristaltic pumps. This is a relatively time consuming activity. In addition, the surgeon often has to adjust the pump speed each time the shaver is used. This is because the shaver will draw fluid from the cavity thereby requiring the surgeon to increase the flow rate of fluid into the cavity. In addition, the light source for illuminating the cavity is functionally independent of the camera used to record the image inside the cavity. Accordingly, the surgeon has to white balance the camera in order to provide a relatively clear image. In addition, because the endoscopy system is typically shared between different surgeons, the various parameters such as flow rate, cavity pressure, shaver speed and so forth have to be readjusted virtually every time a doctor begins using the equipment after another doctor has finished using the equipment.

In addition to the foregoing, the equipment used for performing surgery often uses a shaver handpiece which is subject to certain disadvantages. For example, the shaver handpiece is often driven by a motor which is connected by a gear box to the shaver blade. Not only does the presence of the gear box complicate the construction of the shaver, the gears within the gear box could fail upon receipt of excess torque also tended to cause premature failure of the shaver handpiece. In addition, because the flow of debris through the shaver handpiece does not often follow a straight path, the debris will often plug the shaver handpiece making the handpiece inoperable.

SUMMARY OF THE INVENTION

Accordingly, an advantage of the present invention is to provide an apparatus for endoscopic surgery which is relatively simple to use. In this regard, a related advantage of the present invention is to provide an apparatus for endoscopic surgery which minimizes the time required for surgeons and nurses to set up and operate.

A further advantage of the present invention is to provide an apparatus for endoscopic surgery in which the pressure within the cavity can be accurately controlled. In this regard, a related advantage of the present invention is to provide an apparatus for endoscopic surgery in which the irrigation pump controls the flow rate of fluid into the cavity while the aspiration pump is used to control the pressure of fluid within the cavity.

An additional object of the present invention is to provide an apparatus for endoscopic surgery in which various parameters associated with operating the apparatus can be stored and retrieved with relative ease. A related advantage of the present invention is to provide an apparatus for endoscopic surgery which is menu driven.

Another advantage of the present invention is to provide an apparatus for endoscopic surgery in which debris from the cavity passes through the shaver handpiece in a relatively straight direction.

Another advantage of the present invention is to provide an apparatus for endoscopic surgery which uses gear pumps to control the flow of fluid into and out of the cavity without the use of peristaltic pumps.

The present invention provides for an apparatus for endoscopic surgery which utilizes a gear pump for both the irrigation and aspiration of the fluid from the cavity. The speed of the irrigation pump is held generally constant while the speed of the aspiration pump is varied in response to the pressure within the joint. Both the irrigation pump and the aspiration pump are contained in a disposable cassette which is simply inserted into a pump drive unit. Once a flow rate for the irrigation pump is selected, the flow rate of the irrigation pump remains constant. While the input flow rate can be set at various fixed levels during examination, the irrigation pump will automatically be switched to a predetermined input flow rate when a resection tool is used. The present invention further includes a pressure sensor which senses the pressure of the fluid in the conduit connecting the irrigation pump to the cavity. The output of the pressure sensor is used for controlling and varying the speed and therefore the suction rate of the aspiration pump. As a result, the pressure in the cavity is maintained at a desired level.

The present system monitors the fluid pressure in the input conduit by using a pressure dome located in the disposable cassette. The pressure dome rises and falls with increases and decreases of fluid pressure within the cavity respectively. The pump drive unit utilizes a proximity sensor for sensing the height of the pressure dome which is then determinative of the fluid pressure. Prior art systems utilize an air column for indicating pressure which is a more complex and fragile system using an orifice which has a tendency to plug during the operation. This sensed pressure of the input conduit is corrected to accurately determine the actual pressure within the cavity. Typical endoscopy systems have a relatively long input conduit. At the same time, the inside diameter of the input conduit is relatively small so as to maintain flexibility. When fluid under pressure flows through the input conduit, a pressure drop occurs through the input conduit. This pressure drop through the input conduit, which may be a relatively large percentage of the pressure within the cavity, will be influenced by the diameter of the input conduit and also by the rate of flow through the input conduit. Accordingly, as the flow rate through the input conduit is varied, the pressure drop through the input conduit will vary correspondingly. For this reason, sensing the pressure in the input conduit alone will not accurately measure the pressure within the cavity because of the pressure drop through the input conduit. It is therefore desirable to be able to reliably determine the pressure drop through the input conduit in order to more accurately provide an indication of (and ultimately control) the pressure within the cavity based upon a pressure measurement taken at the input conduit.

Because the irrigation pump of the present invention is used to provide a fixed, selected flow rate of fluid into the cavity while the aspiration pump, through variable speed, controls pressure, the present system has several important advantages. First, the present system is able to estimate the pressure in the cavity with greater accuracy by compensating for the pressure drop which occurs through the portion of the input conduit between the pressure sensor and the cavity. This is because the pressure drop through the input conduit is a function of the flow rate through the input conduit which can be easily determined because the irrigation pump establishes the flow rate at a preselected fixed magnitude. With a fixed input flow rate, the pressure drop through the input conduit can be accurately determined and therefore the output from the pressure sensor located at the outlet of the irrigation pump can more precisely indicate the actual pressure of fluid in the cavity. With a more accurate indication of the actual pressure in the cavity, the present system can provide a more accurate way for controlling the pressure in that cavity.

In other endoscopy systems where the irrigation pump is used to control pressure, the flow rate through the input conduit (1) would vary as the speed of the input pump continuously changed to maintain the desired pressure within the cavity and (2) would be more difficult to accurately determine because of the continuous variation in flow. Because the flow rate through the input conduit would vary and be difficult to determine, the pressure drop through the input conduit would also vary and be difficult to determine. The output of the pressure sensor would therefore not provide such an accurate estimate of the pressure within the cavity. Accordingly, the fact that the irrigation pump of the present system is used to control the flow at a constant rate while the aspiration pump is used to control pressure allows a more accurate determination of both the magnitude of pressure within the cavity and the volume of flow of fluid into the cavity.

Second, another important advantage of the present system which is obtained by having the irrigation pump provide a preselected fixed flow rate while the speed of the aspiration pump is varied to control pressure involves the performance of the present system when leakage of fluid occurs from the cavity, which is quite common during endoscopic procedures. When such leakage occurs, the pressure drop sensed by the present system automatically reduces the speed of the aspiration pump in order to maintain the pressure so that less fluid flows through the output conduit. At the same time, the flow of fluid delivered by the input conduit remains unchanged. The present system is therefore able to maintain the pressure in the joint while accommodating for substantial variations in leakage without a change in the input flow rate.

In other endoscopy systems where the aspiration pump is used to provide a preselected fixed flow rate, the irrigation pump would have to supply a sufficient amount of fluid to maintain the pressure in the cavity as well as to compensate for fluid leaving the cavity (1) by leakage and (2) through the aspiration pump. When such leakage becomes large, the capacity of the irrigation pump could be exceeded as the irrigation pump attempts to increase the input flow rate to maintain the desired pressure within the cavity while also attempting to compensate for both the leakage out from the cavity as well as the fluid drawn out of the cavity by the aspiration pump. In addition, if the aspiration pump were used to provide a fixed flow rate, the amount of fluid flowing into the cavity would also not be as accurately determined because of leakage of fluid from the cavity, the amount of which could vary substantially between different operations.

There are several other important features of the present system. For example, the aspiration pump of the present system is a two-directional gear pump which allows fluid to flow through a first output conduit when the aspiration pump is driven in one direction and allows fluid to flow through a second output conduit when the aspiration pump is driven in a second direction. The flow of fluid through the second output conduit occurs when a resection tool is used. This switching of output conduits is accomplished by a series of check valves which automatically switch the conduits when the direction of the motor is reversed eliminating the need to manually adjust valves or tubing to accommodate the different flow rates coming from the separate conduits.

An additional feature of the present invention is that both the irrigation pump and the aspiration pump are gear pumps and are contained in the disposable cassette. The use of the disposable cassette significantly simplifies the process for getting ready for surgery by providing a one step system of inserting the cassette for engaging the two pumps. The use of gear pumps instead of prior art peristaltic pumps provides a system which requires less energy and is more efficient. A peristaltic pump requires the tubing to be threaded through the pump in order for the pump to function. Once assembled, most of the energy required for the pump to operate is used to compress the plastic tube and not to pump the liquid. Because the cassette system is disposable, the fluid medium can be introduced into the pump and the cassette then can be simply inserted into the pump drive unit. This one step operation significantly simplifies the steps necessary to get ready for the operation.

Moreover, the present system does not have a tachometer per se which measures the speed of the motors that drive the irrigation and aspiration pumps. Rather, the present system measures the frequency of electrical pulses generated in part by the movement of magnets within each of the motors. The frequencies of the electrical pulses are indicative of the speed of their respective motors. These electrical pulses are delivered to a microprocessor which monitors the changing frequencies of the pulses to control the speed of the irrigation and aspiration pump motors.

Further, while the present system terminates the operation of the irrigation and aspiration pumps when the pressure in the cavity becomes excessive, the present system does not immediately terminate the flow of fluid into the cavity when the pressure in the cavity falls below a predetermined limit. Rather, the aspiration pump progressively reduces its speed in an attempt to maintain the pressure within the cavity at the desired magnitude. This reduction in speed continues up to the point where the operation of the aspiration pump terminates. When this occurs, while flow of fluid into the cavity continues, there is no flow of fluid drawn from the cavity through the aspiration pump and therefore the only flow of fluid out from the cavity is by virtue of leakage.

BRIEF DESCRIPTION OF THE DRAWINGS

Various advantages of the present invention will become apparent to one skilled in the art upon reading the following specification and by reference to the following drawings in which.

DETAILED DESCRIPTION OF THE PREFERRED EMBODIMENT

The following description of the preferred embodiment of the present invention is merely exemplary in nature and is in no way intended to limit the invention or its application or uses.

Figure 1:
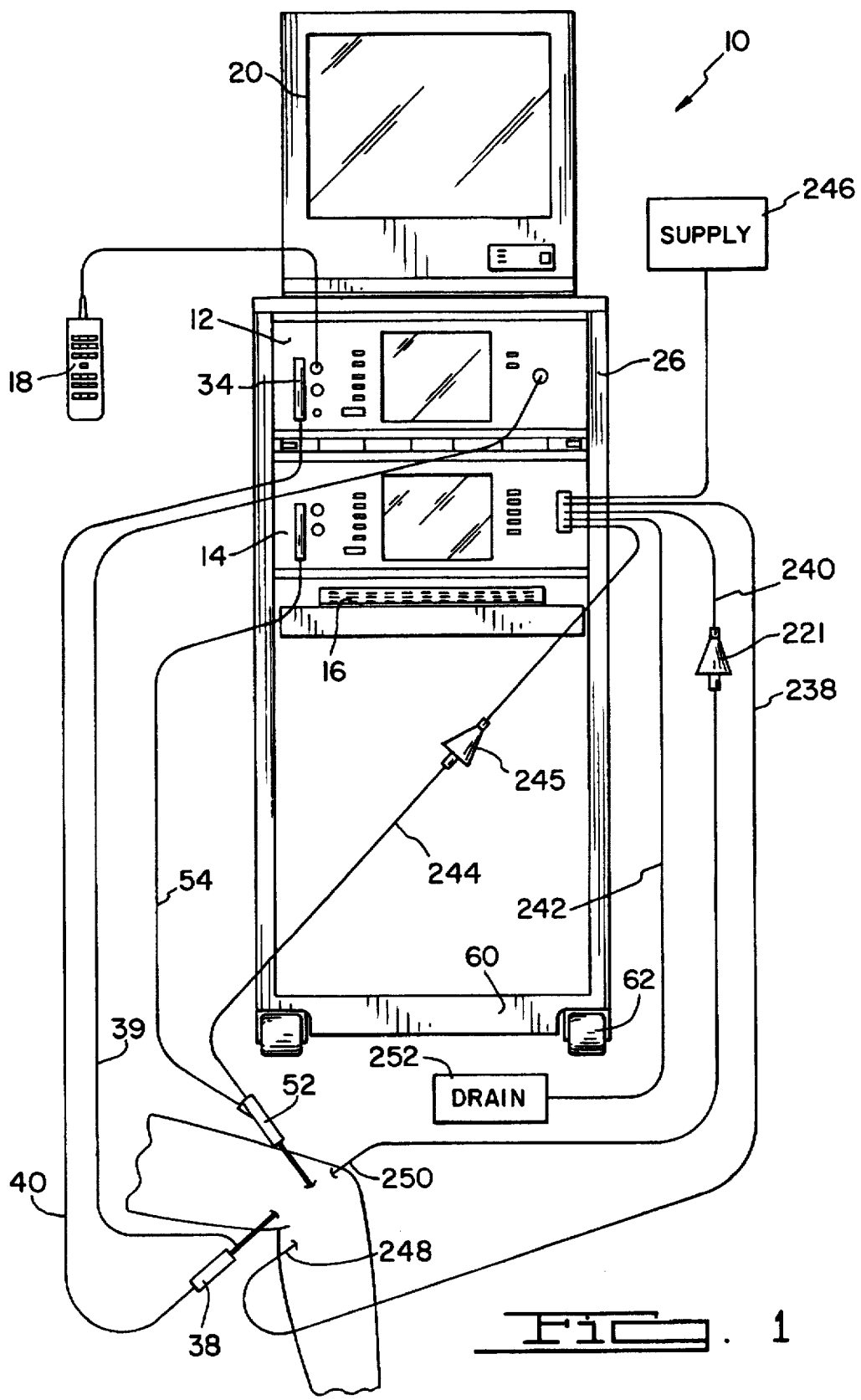
FIG. 1 is a front view of the apparatus for performing endoscopic surgical procedures according to the preferred embodiment of the present invention.
Figure 2:
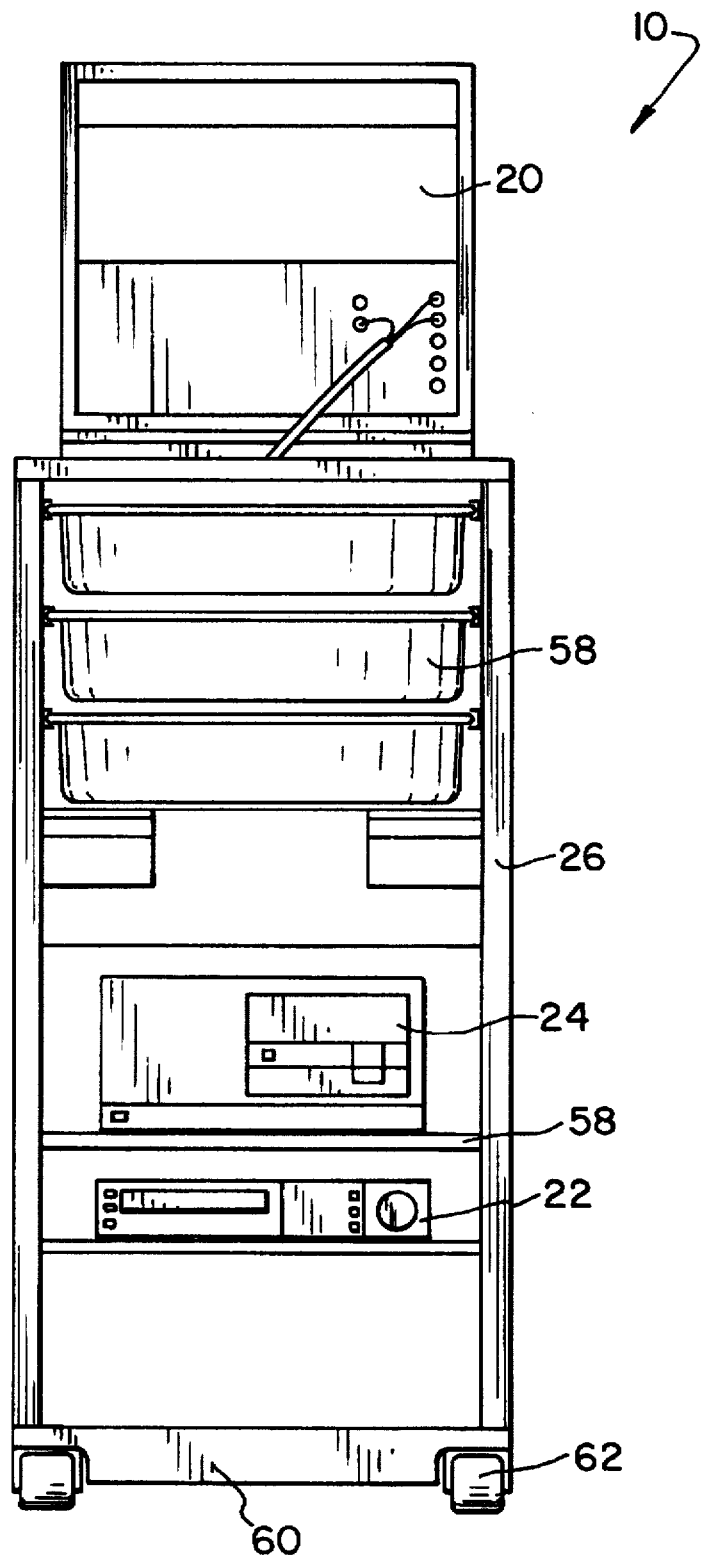
FIG. 2 is a rear view of the apparatus for performing endoscopic surgical procedures according to the preferred embodiment of the present invention.

The apparatus for performing endoscopic examination and resection apparatus of the present invention is shown in FIGS. 1 and 2 and is generally designated by the numeral 10. The apparatus 10 comprises an imaging unit 12, an intra-articular unit 14, a keyboard 16, an autoclavable remote control unit 18, a video monitor 20, a video cassette recorder 22, a video printer 24 and a cart 26. Each of these components of the apparatus 10 will be individually discussed below.

The cart 26 houses the majority of the components of the apparatus 10. The cart 26 is pre-wired for easy installation of the imaging unit 12, the intra-articular unit 14, the video cassette recorder 22 and the video printer 24. In this regard, most of the electrical conductors connecting the various components of the apparatus 10 are contained internally within the cart 26 and are connected to various electrical connectors mounted on the cart 26. By simply inserting the imaging unit 12 or the intra-articular unit 14 into the cart 26, all the necessary inter-related connections are automatically made thereby reducing the time required to set-up of the system. As will be more fully described below, the electrical conductors within the cart 26 allow the imaging unit 12 to intercommunicate with the intra-articular unit 14 so as to allow the imaging unit 12 to operate interdependently with the intra-articular unit 14. For example, the remote control unit 18 may be connected to either the imaging unit 12 or the intra-articular unit 14 and can control both. In addition, the imaging unit 12 may be used when the operation of the intra-articular unit 14 is being programmed. Other ways in which the imaging unit 12 and the intra-articular unit 14 operate interdependently are described below.

The cart 26 provides ample storage racks 58 for storage trays, the video cassette recorder 22 and the video printer 24. The cart 26 is also equipped with an isolation transformer located in the base 60 of the cart 26 which provides for electrical leakage containment of the components within the cart 26. The cart 26 can be easily maneuvered on its swivel locking caster wheels 62.

Figure 3:
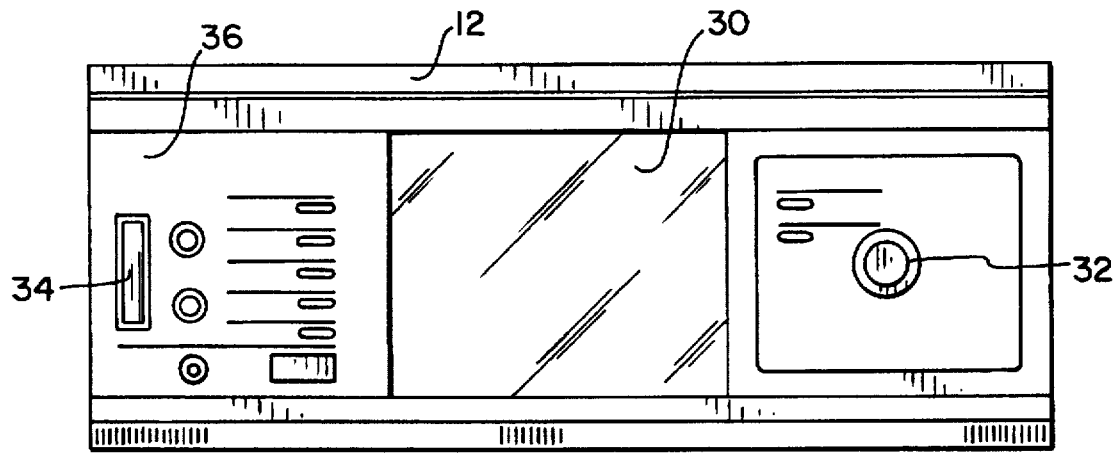
FIG. 3 is an enlarged front view of the imaging unit of the apparatus for performing endoscopic surgical procedures shown in FIG. 1 according to the preferred embodiment of the present invention.

The imaging unit 12 of the apparatus 10 as shown in FIG. 3 comprises an RGB monitor 30, a high output xenon light source 32 and a camera 34 all contained in a chassis 36. The RGB monitor 30 can be used as a programming screen with menu driven control for individual system preferences such as light illumination and picture color as more fully described below. Alternatively, the monitor 30 can be used as a secondary monitor for viewing the surgical procedure. System programming of the imaging unit 12 is accomplished by utilizing the keyboard 16 as well as by the remote control unit 18 as will also be more fully described below. The camera 34 has an auto iris which provides instant illumination adjustments to reduce glare while an auto white balance eliminates time consuming camera set-ups. The camera 34 receives optical signals from a camera head 38 which is connected to the chassis 36 by both a fiber optic cable 39 and an electrical cord 40. Operation of the various functions of the imaging unit 12 can be accomplished by controls on the front panel of the imaging unit 12 or by the remote control unit 18 as described below.

Figure 4:
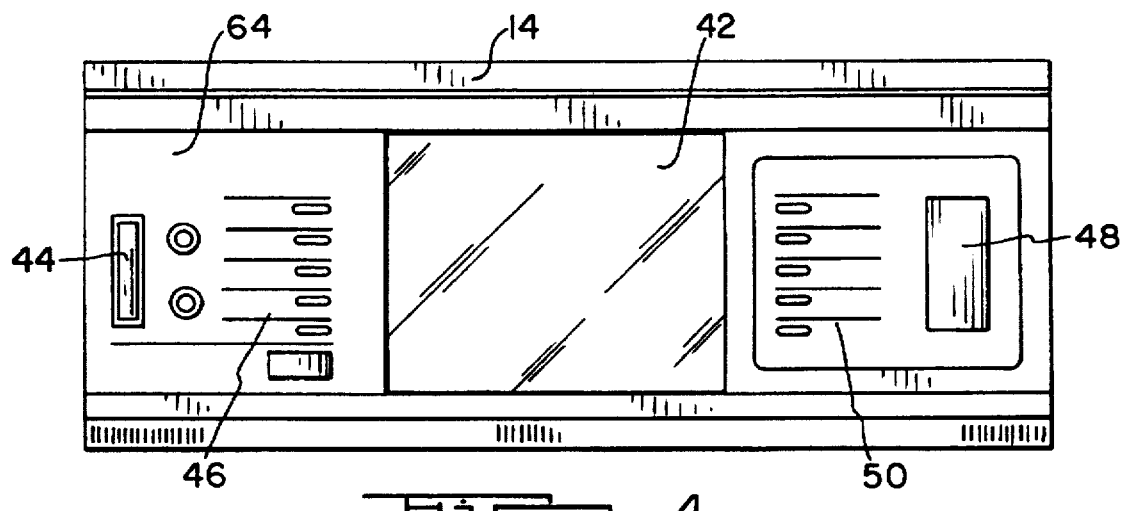
FIG. 4 is an enlarged front view of the intra-articular unit of the apparatus for performing endoscopic surgical procedures shown in FIG. 1 according to the preferred embodiment of the present invention.

The intra-articular unit 14 of the apparatus 10 as shown in FIG. 4 comprises an RGB monitor 42, a shaver power unit 44 and a pumping unit 48, all of which are contained in a chassis 64. The RGB monitor 42 provides display of current running information (e.g., the speed of the shaver, fluid flow rate and cavity pressure) and can be utilized for information on operating the apparatus 10. Inflow of fluid from the pumping unit 48 to the cavity can be accomplished through the camera head 38 or by a separate cannula, both utilizing built-in pressure protection. The shaver power unit 48 is used to drive shaver handpiece 52 (see FIG. 1) which is connected to the chassis 64 by the electrical cord 54. Operation of the various functions can be accomplished by controls on the front panel of the intra-articular unit 14 or also by means of the remote control unit 18 as described below.

Figure 5:
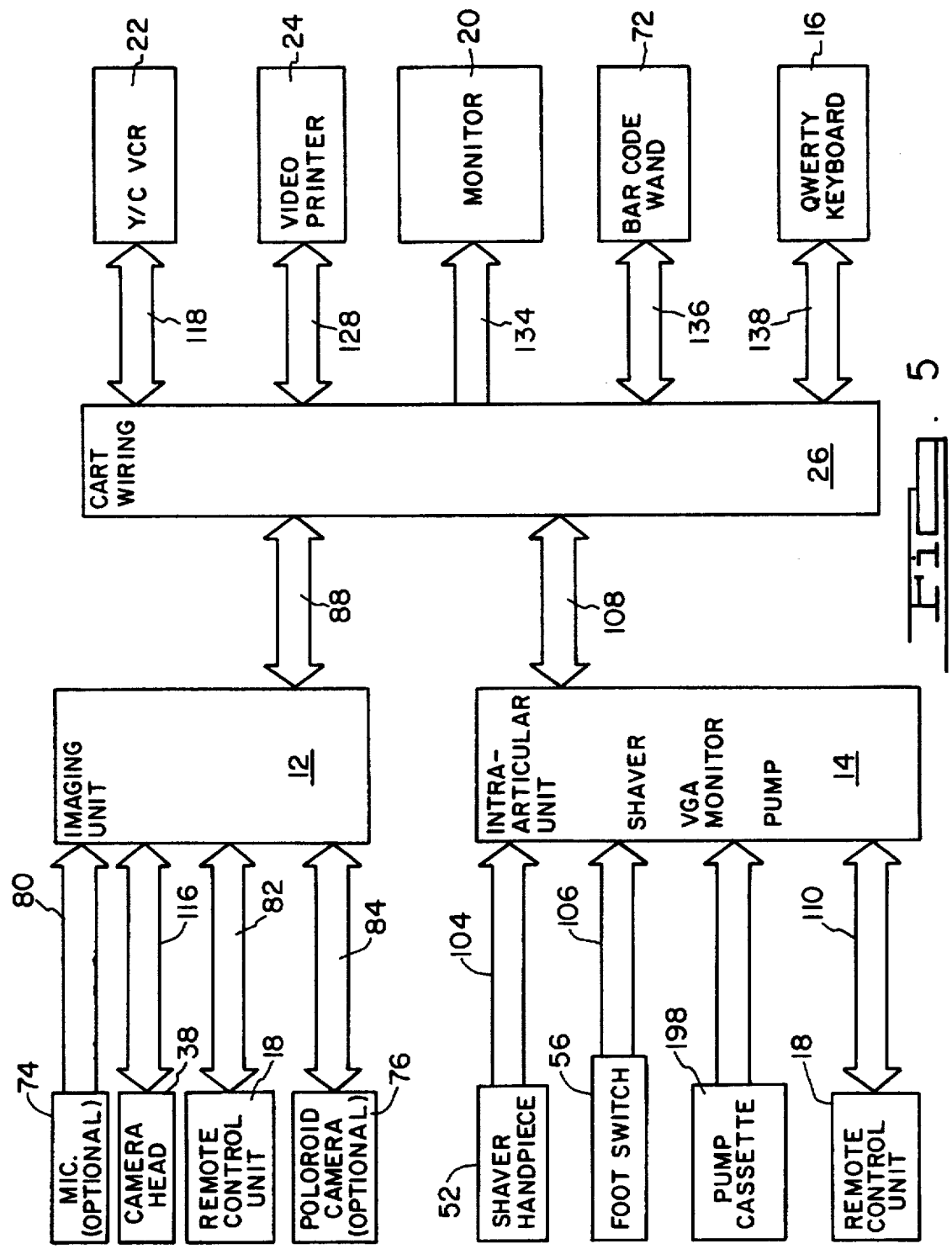
FIG. 5 is a block diagram showing the components of the apparatus for performing endoscopic surgical procedures shown in FIG. 1 according to the preferred embodiment of the present invention.

Referring now to FIG. 5, an upper level block diagram of the apparatus 10 is shown depicting the imaging unit 12, the intra-articular unit 14, the video cassette recorder 22, the video printer 24, the video monitor 20, the keyboard 16, an optional bar code wand 72 and the cart 26. The components of the imaging unit 12 and the intra-articular unit 14 will be more fully discussed below. The video monitor 20, normally located on the top of the cart 26, receives the output of the imaging unit 12 and provides a color picture of the endoscopic procedure from the output of the camera head 38. Various connections are made from the video monitor 20 to the cart 26 to provide video output for the imaging unit 12 as well as receiving output from the video cassette recorder 22. These connections are made through the bus 134 and include RGB video, y/c video input and audio input.

The video cassette recorder 22 is provided to enable the surgeon to make a taped record of the endoscopic examination or procedure. The video cassette recorder 22 is located in the rear of the cart 26 normally located on one of the storage racks 58. Various connections are made to the cart 26 for recording and playback of the pictures created by the imaging unit 12. These connections are made through the bus 118 and include composite VCR out, audio in, video cassette recorder control, y/c video, audio out and y/c video out.

The video printer 24 is provided in order to allow the surgeon to have a permanent copy of any picture displayed on the video monitor 20. The video printer 24 is also located at the rear of the cart 26 on one of the storage racks 58. Various connections are made through the cart 26 for allowing the video printer 24 to interface with the other components of the imaging unit 12. These connections are made through the bus 128 and include freeze RGB, RGB video in and RS232.

The bar code wand 72 connected to the cart 26 through the wand bus 136. The bar code wand 72 is used to allow easy and relatively quick readouts of operating room charges, patient charges or other standard information. The keyboard 16 is also an optional device and is connected to the cart 26 by the keyboard bus 138.

The remote control unit 18 may be connected to either the imaging unit 12 or the intra-articular unit 14. The operation of the remote control unit 18 is identical regardless of where the connection is made. The remote control unit 18 includes a plurality of push-button switches which control the following operational characteristics of the apparatus 10:

increase fluid flow rate
decrease fluid flow rate
increase cavity pressure
decrease cavity pressure
on/off
lavage mode
shaver stop/start
increase shaver speed
decrease shaver speed
shaver mode change (i.e., forward, reverse, oscillate)
print image
start/stop video cassette recorder
start/stop timer
increase iris contrast
auto/manual iris
decrease iris contrast
scroll up menu
enter selection on menu
scroll down menu Because the remote control unit 18 is autoclavable and therefore used in the sterile field proximate to the surgical site, the surgeon is able to control the apparatus 10 from the sterile field by using the remote control unit 18.

Figure 6:
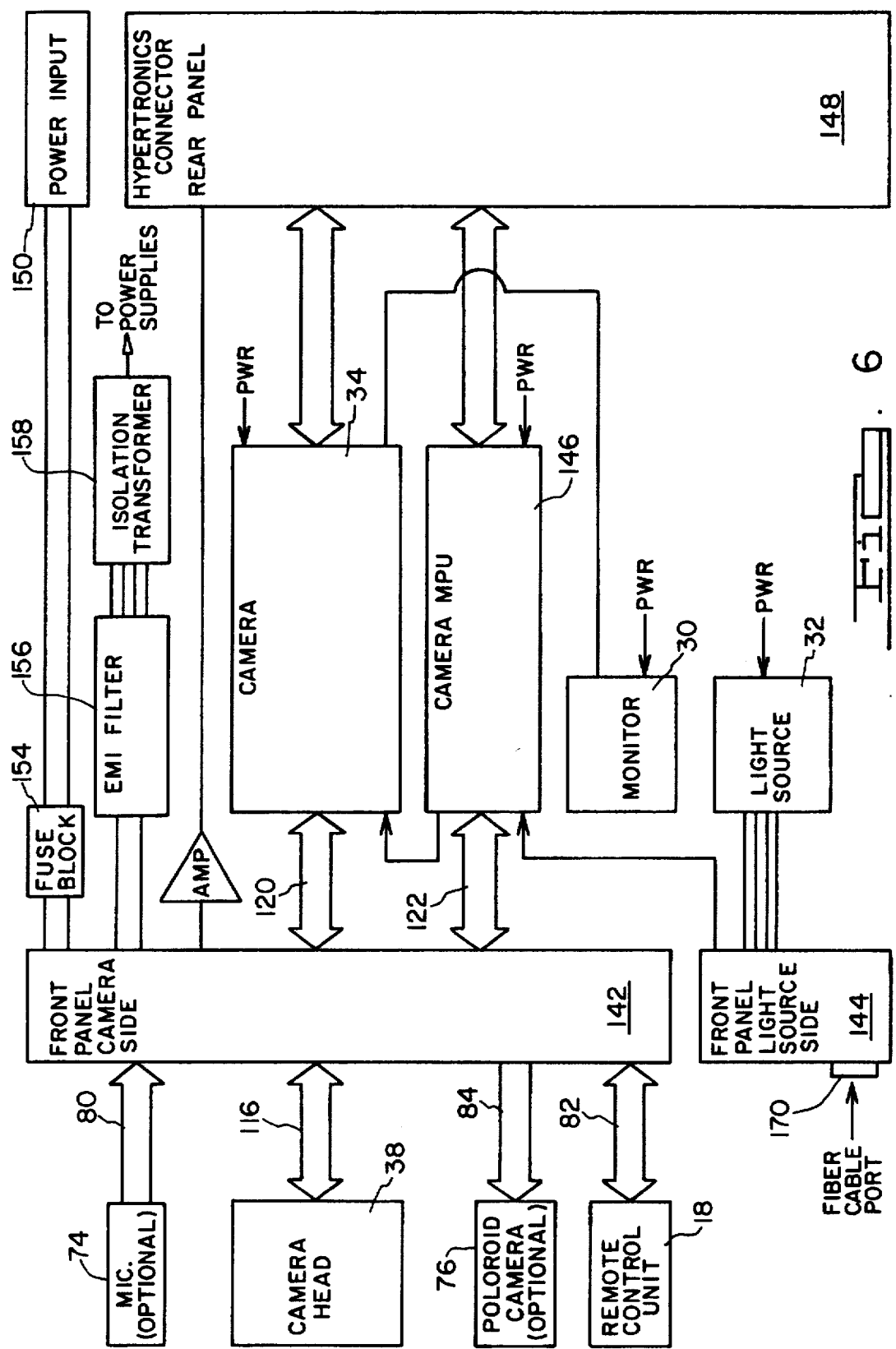
FIG. 6 is a block diagram showing the components of the imaging unit of the apparatus for performing endoscopic surgical procedures shown in FIG. 1 according to the preferred embodiment of the present invention.

Referring now to FIG. 6, a block diagram of the imaging unit 12 is shown. The imaging unit 12 comprises a camera front panel 142, a light source front panel 144, the light source 32, the RGB monitor 30, a camera MPU 146, and the camera 34. All necessary connections to the other components within the apparatus 10 are located on the rear of the imaging unit 12 and inserting the imaging unit 12 into the cart 26 makes the connections through the use of Hypertronic™ zero insertion connectors. In this regard, the insertion of the imaging unit 12 makes the following connections through the bus 88 to the cart 26: audio, video cassette recorder control, y/c video, composite video, freeze RGB video, RGB video, RS 232-to-print, remote control unit bus, serial bus (unit-to-unit), wand bus, keyboard bus, serial image unit bus and unit-to-unit enable. The camera front panel 142 provides an electrical connection to electrically couple the imaging unit 12 to the microphone 74 through the bus 80, the camera head 38 through the bus 116, the polaroid camera 76 through the bus 84 and the remote control unit 18 through the bus 82. The camera front panel 142 is also electrically coupled to the camera 34 through the bus 120, the camera MPU 146 through the bus 122 and the input power 150.

All five RS-232 serial ports of the imaging unit 12 use a plurality UARTS controlled by the camera MPU 146, each having their own baud rate generator. The S-bus output is a serial data bus with a standard protocol data system generated by the camera MPU 146 using an internal timer. All ports are double buffered allowing the camera MPU 146 to write or read characters irrespective of the peripheral timing. The camera MPU 146 itself contains multiple pulse modulators which when attached to a low pass filter produce controllable analog voltages. These voltages preferably control the adjustment of a camera iris for the camera 34 as well as the beeper volume. Multiple digital input/output lines of the camera MPU 146 are used for switch status input, remote scanning, S-bus generation, SIO control, camera control and video multiplexer control.

The RGB monitor 30 of the imaging unit 12 is preferably a 9-inch monitor which displays various menus enabling the surgeon to quickly set or change various operating parameters by using the remote control unit 18. Each menu is generated in accordance with a software program 298 (which is described in connection with FIGS. 12 and 13) by the camera MPU 146 and written to the external RAM memory at VIDSTORE, as listed in the Appendix. This data is then downloaded to a video RAM in the MPU 146 during the vertical retrace. The various menus displayed on the RGB monitor 30 will be more fully described below.

The video signal generated by the camera MPU 146 represents three identical channels of RGB information. The video signal from the camera MPU 146 is delivered to the video monitor 20, the RGB monitor 30, the video printer 24 and the video cassette recorder 22. In this regard, a composite video signal is delivered to the video cassette recorder 22, with all other peripherals receiving either composite or RGB video.

The RGB monitor 30 preferably displays the video signal from the camera MPU 146 with a computer generated overlay or with freeze images. The video printer 24 and the video cassette recorder 22 preferably receive a camera image with an overlay generated thereon. The overlays may represent patient ID or other helpful information relating to the surgical procedure. Selection of the source/destination video and sync is performed by a multiplexer in the video section operating under CPU control.

The front panel 142 of the camera 34 offers various controls for operating the apparatus 10. A power switch is electrically coupled to the input power 150 through the fuse block 154. The power switch is also electrically coupled to the various power supplies of the imaging unit 12 through an EMI filter 156 and an isolation transformer 158. In addition to the power switch, the front panel 142 of the camera 34 provides an auto iris on/off switch, a print switch, a scroll up switch, a scroll down switch and an enter switch. All of the above mentioned switches are electrically coupled to the camera MPU 146 through the bus 122.

The camera MPU 146 is preferably a Zilog Z86C97 CMOS digital TV controller containing a Z8 CPU core, on screen display generator, multiple pulse width modulator and parallel input/output ports. Documentation on this microprocessor is available from the manufacturer in the form of the Z86C27/C97 Manual and the Z8 Family Design Handbook, both documents of which are hereby incorporated by reference.

The imaging unit 12 further contains both internal and external random-access memory and an external EPROM program memory. A memory mapping may be found in module EQ, also listed in the Appendix B.

The imaging unit 12 further includes a front panel 144 of the light source 32 which provides a port 170 for connection of the optical fiber cable 39, as well as a lamp-on switch and a lamp-off switch. The lamp-on and lamp-off switches control the xenon light source 32 which delivers light to the camera head 38 through the optical fiber cable 39.

The components of the intra-articular unit 14 will now be described in greater detail with reference to FIG. 7. The intra-articular unit 14 comprises the shaver power console 46, the pump console 50, the shaver power unit 44, the pumping unit 48, the RGB monitor 42, and a shaver/pump MPU 182. All necessary connections to the other components within the apparatus are located on the rear of the intra-articular unit 14 and inserting the intra-articular unit 14 into the cart 26 makes the connections through the use of Hypertronic™ zero insertion connectors 184. In this regard, the insertion of the intra-articular unit 14 into the cart 26 makes the following connections through the bus 108 to the cart 26: serial intra-articular unit bus, data bus (unit-to-unit), remote control unit bus and unit-to-unit enable.

The shaver power console 46 provides electrical connections to electrically couple to the intra-articular unit 14 the shaver handpiece 52 through the bus 104, the foot switch 56 through the bus 106, and the remote control unit 18 through the bus 110. The shaver power console 46 is also electrically coupled to the shaver motor drive electronics 44 through the bus 90, the shaver/pump MPU 182 through the bus 92 and the input power 186. The shaver power console 46 includes a power switch which is electrically coupled to the input power 186 through a fuse block 190. The power switch is also electrically coupled to the various power supplies of the intra-articular unit 14 through an EMI filter 192 and an isolation transformer 194.

The RGB monitor 42 preferably comprises a 9 inch VGA color monitor which displays real-time system variables in a variety of bar, numeric and message formats. For example, the RGB monitor 42 may simultaneously display a bar graph of the speed of the shaver handpiece 52, an indication of the mode of operation of the shaver handpiece 52 (forward, reverse or oscillate), as well as an indication of whether the shaver handpiece 52 in on or off. Alternatively or simultaneously displayed on a split screen, the RGB monitor 42 may generate a display showing a bar graph of the flow rate of fluid into the cavity as well as the pressure of fluid in the cavity. The VGA interface for the RGB monitor 42 preferably comprises an industry standard VGA card which is mounted as a daughter board within the intra-articular unit 14.

The RGB monitor 42 provides a high resolution (640× 480) pixel VGA map. Due to this high resolution, the intra-articular unit 14 hardware is designed to maximize transfer rate between the shaver/pump MPU 182 and the VGA card in communication with the RGB monitor 42. Maximum data transfer is accomplished by the use of several techniques. First, a memory address-auto increment capability is used to allow CPU-VGA memory transfers without having to load each address prior to each data transfer. In addition, a function decode produces input/ output write, input/output read, memory write and memory read pulses with a single input/output instruction. Furthermore, a strobe pulse is generated on either the rise or fall of a generated command. This eliminates the necessity to use two instructions to produce a strobe pulse. In addition, the VGA transfer is synchronized by an automatic weight pulse stretcher. This eliminates the requirement of the CPU to test for VGA ready status.

Furthermore, the VGA screen is normally mapped as four planes to produce one out of 16 color codes and normally requires writing data four times to the same address to produce color pixels. By eliminating the allowable number of colors to 6 and restricting which colors can over-write others, the intra articular unit 14 can write a color pixel in one operation. In addition, by using a memory mapping technique, the high order bits of the VGA memory map can be set to allow a mirror image of a ROM memory, containing, for example, high resolution logo pictures. When used in conjunction with the auto increment address capability, bytes can be transferred directly from the ROM to the VGA card with one instruction. Finally, incorporating a hardware pixel rotator allows read-modify-write shifting of pixel row data with only two instructions. The combination of the above techniques increases the CPU to VGA data throughput to a peak rate of approximately 682K pixels/ second. Reference information relating to VGA programming is available from the "Programmers Guide to the EGA and VGA Cards", by Ferraro and Addison-Wesley, and "Cirrus CL-GD5320 Technical Reference Manual" by Cirrus Logic, Inc., both documents of which are hereby incorporated by reference.

Figure 7:
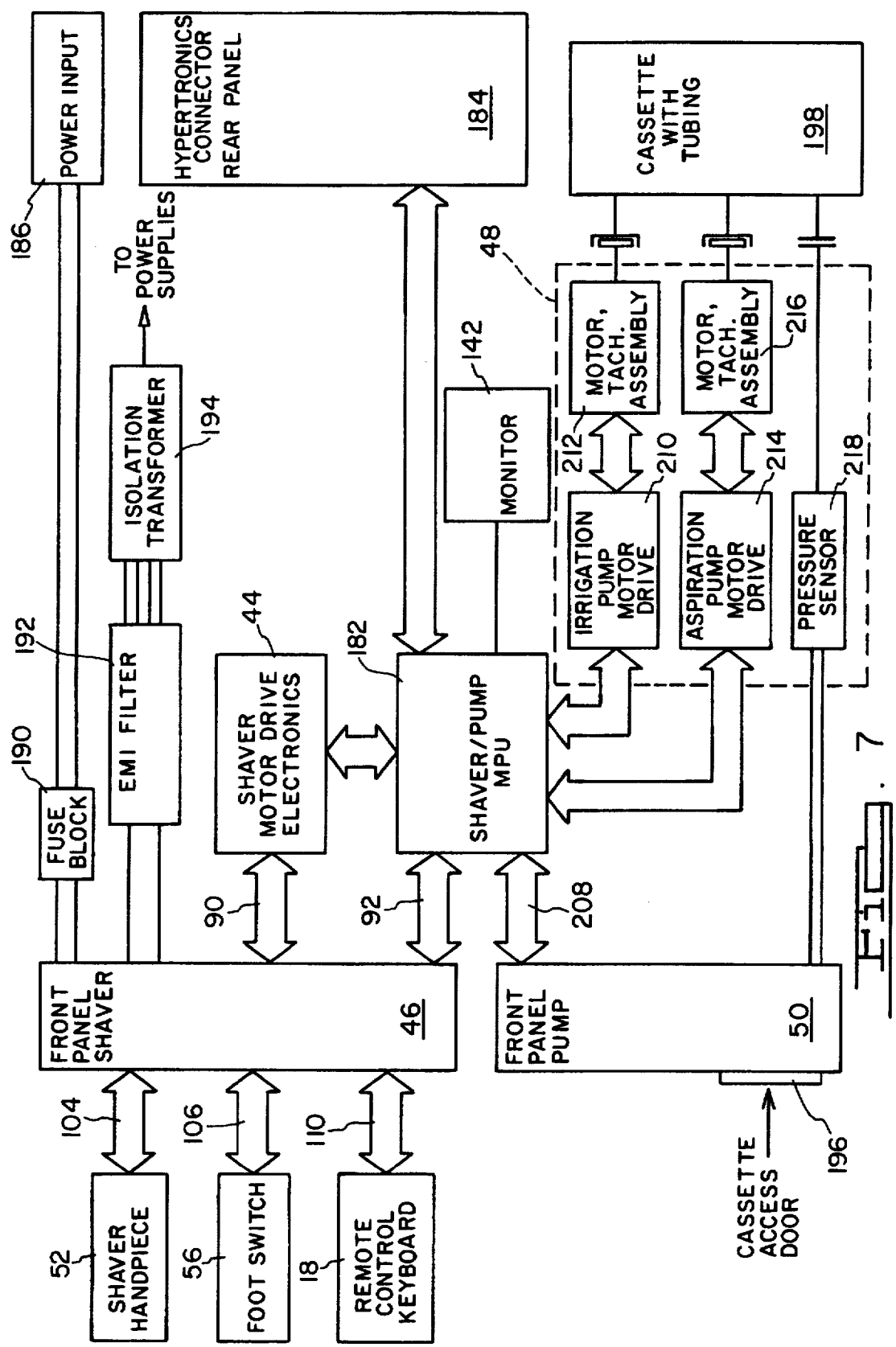
FIG. 7 is a block diagram showing the components of the intra-articular unit of the apparatus for performing endoscopic surgical procedures shown in FIG. 1 according to the preferred embodiment of the present invention.

As shown in FIG. 7, the front panel 50 of the pumping unit 48 of the intra-articular unit 14 provides an access door 196 to install a pump cassette 198, a pressure-up switch, a pressure-down switch, a flow-up switch, a flow-down switch and a pump prime switch. All of the above mentioned switches are electrically coupled to the shaver/pump MPU 182 through the bus 208.

The pumping unit 48 of the intra-articular unit 14 is electrically coupled to the shaver/pump MPU 182 and comprises an irrigation pump motor drive 210 with an associated tachometer 212, an aspiration pump motor drive 214 with an associated tachometer 216 and a pressure sensor 218. Including both the irrigation and aspiration pumps 222 and 224 within the pump cassette 198 enables both of the pumps 222 and 224 to be driven when the pump cassette 198 is inserted through the access door 196. The pressure sensor 218 monitors the system pressure as will be described later herein. The separate pumps for irrigation and aspiration have capabilities of 0-1000 ml/min and a pressure range of 0-150 mm Hg.

Figure 8:
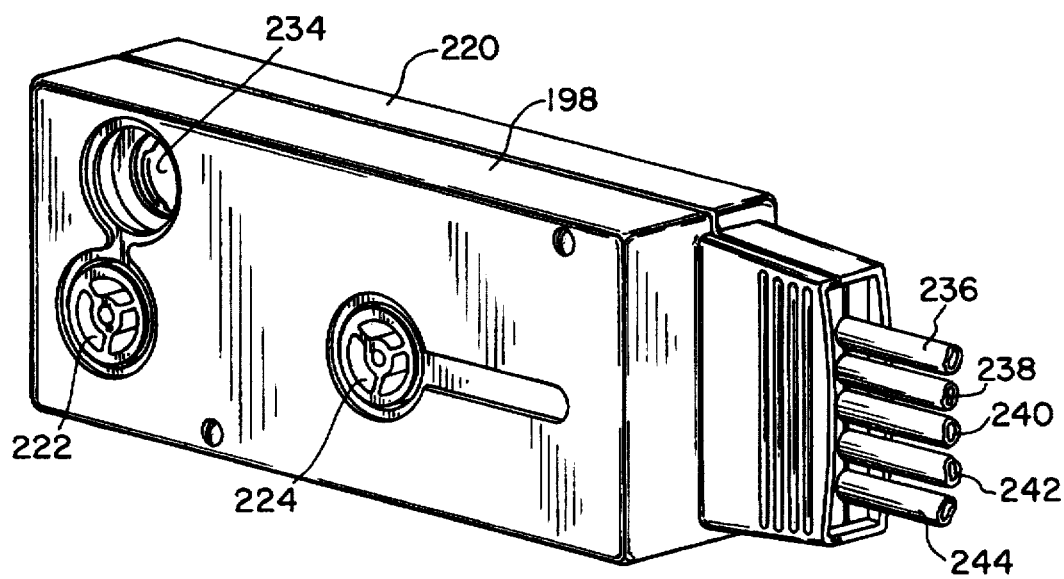
FIG. 8 is a perspective view of the pump cassette which is used with the intra-articular unit shown in FIG. 4 according to the preferred embodiment of the present invention.
Figure 9:
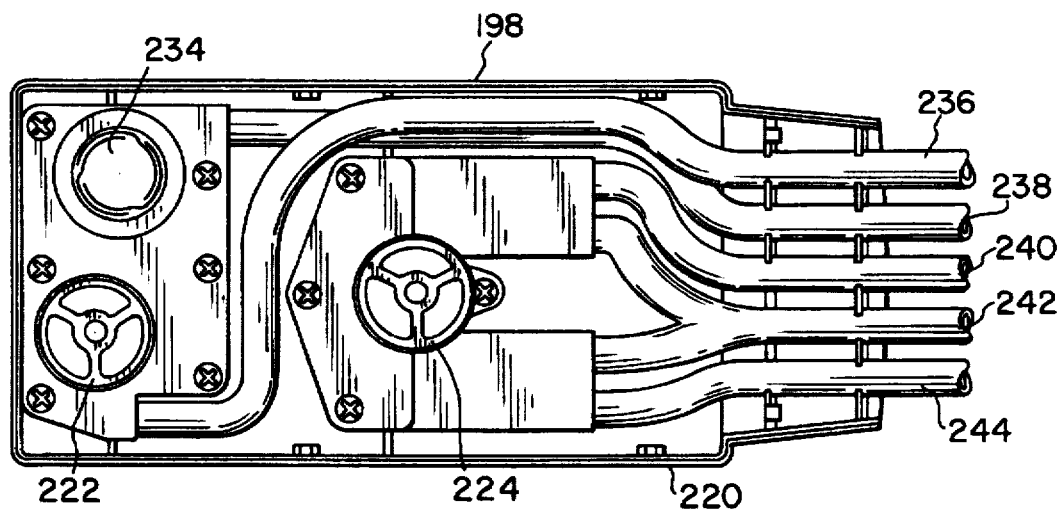
FIG. 9 is a plan view showing the internal components of the pump cassette shown in FIG. 8 according to the preferred embodiment of the present invention.
Figure 10:
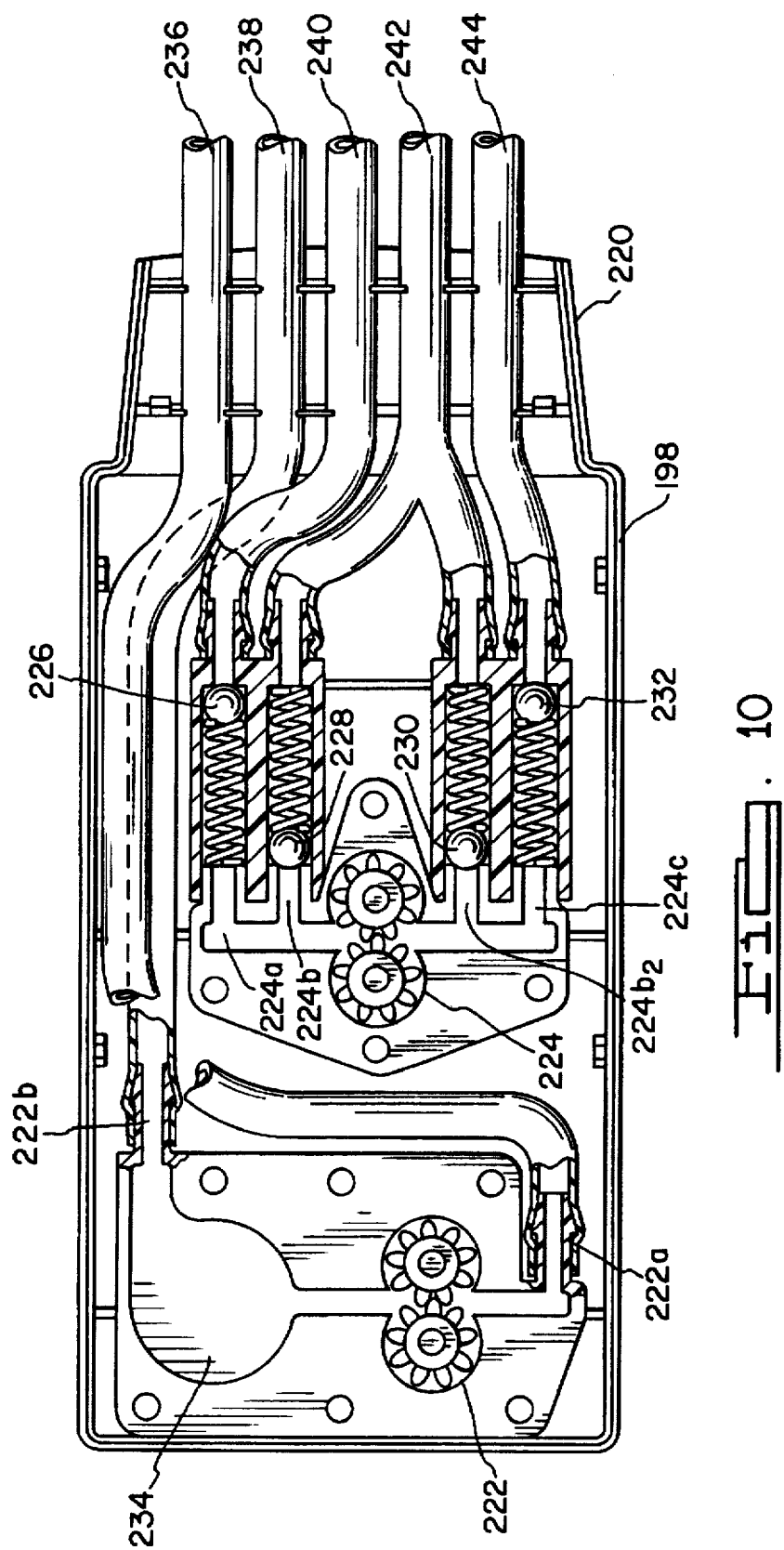
FIG. 10 is a plan view partially in cross-section of the internal components of the pump cassette shown in FIG. 8 according to the preferred embodiment of the present invention.

With reference to FIGS. 7 and 8, the tachometers 212 and 216 are not physically connected to the motors that drive the pumps 222 and 224. Rather, the pumping unit 48 generates electrical pulses by the movement of magnets on rotors of the irrigation and aspiration pumps 222 and 224 as the magnets move rotationally past stationary Hall-effect sensors. The electrical pulses are indicative of the speed of the motors and are delivered to the shaver/pump MPU 182. The shaver/pump MPU 182 uses the changing frequency of the pulses to control the speed of the motor drives 210 and 214.

The microprocessor of the shaver/pump MPU 182 is preferably a Hitachi HD647180X CMOS device containing an HD64180 CPU core, multiple timers, dual serial input/output port, a 512 byte internal ram memory and a 16K byte internal OTP program ROM memory and parallel input/output ports. Documentation for these components is available from the manufacturer in the form of HD 647180X 8 bit Microcontroller Hardware Manual and an HD 64180 Series 8 bit Microprocessor Programming Manual, both documents of which are hereby incorporated by reference. Detailed mapping for memory and input/output is defined in the Equate module EQ, as listed in the Appendix D.

The shaver motor drive electronics 44, the irrigation pump motor drive 210 and the aspiration pump motor drive 214 each determine speed and direction for each of the motors of the motor drive circuits 210 and 214. More specifically, the speed is controlled by analog voltages produced from three D/A converters. The direction of each of the irrigation and aspiration pump motors is determined by a logic level signal generated by the shaver/pump MPU 182.

The intra-articular unit 14 includes several internal monitoring circuits for monitoring motor current, motor drive fault, status and pressure sensed by the pressure sensor 218. The two port serial input/output is provided to allow communication with the imaging unit 12 or an external computer and external host computer interface. The intra-articular unit 14 may be controlled by either the front panel switches on the unit 14, the foot switch 56 or the remote control unit 18. An external, non-volatile memory contains calibration constants which control motor control offset and gain.

The pump cassette 198 will now be described in greater detail with particular reference to FIGS. 1 and 8 through 10. The pump cassette 198 comprises the housing 220, the irrigation pump 222, the aspiration pump 224, the ball check valves 226, 228, 230 and 232, the pressure dome 234 and the five fluid tubes 236, 238, 240, 242 and 244.

The tube 236 connects a fluid supply 246 with the inlet side 222a of the irrigation pump 222. The tube 238 connects the output 222b of the irrigation pump 222 to the cannula 248 being used for introducing fluid into the cavity. The pressure dome 234 reacts to the pressure present in the tube 238 so as to provide an estimate of the fluid pressure within the cavity. The tube 240 connects an outflow cannula 250 with a first input 224a of the aspiration pump 224 through the check valve 226 and the filter 221. The tube 242 connects on output 224b, and on output 224b2 of the aspiration pump 224 with a drain reservoir 252 through both the check valves 228 and 230. The tube 244 connects the outflow from the shaver handpiece 52 with a second input 224c to the aspiration pump 224 through the filter 245. The pump cassette 198 is inserted through the access door 196 (FIG. 7) into the intra-articular unit 14. Once the pump cassette 198 has been inserted into the intra-articular unit 14, the irrigation pump motor drive 210 is automatically coupled to the irrigation pump 222, the aspiration pump motor drive 214 is automatically coupled to the aspiration pump 224, and the pressure sense 218 is positioned proximate to the pressure dome 234.

While the pressure at the outlet of the irrigation pump 222 is readily measured by the pressure sensor 218 in conjunction with the pressure dome 234, the pressure sensed by the pressure sensor 218 may not accurately indicate the pressure in the cavity because the pressure drop through the tube 238 can be significant. The advantage of having the irrigation pump 222 control the flow rate into the cavity is that the flow rate through the tube 238 is known. Since the pressure drop through the tube 238 is a function of the flow rate through the tube 238, the pressure drop through the tube 238 can be accurately determined by the apparatus 10 by subtracting the known pressure drop in the tube 238 from the pressure sensed by the pressure sensor 218.

Operation of the apparatus 10 begins by insertion of the cannulas 248 and 250 into the internal cavity of the patient as shown in FIG. 1. Depending upon the specific operation being performed, the number of incisions can vary between two and four. If the surgery is exploratory in nature and the inflow of fluid is accomplished through the camera head 38, the only incisions required are for the camera head 38 and the cannula 250 for the outflow from the cavity. If the surgery is exploratory in nature, and the inflow of fluid is accomplished by a separate cannula, three incisions must be made: one for the camera head 38, one for the cannula 248 for inflow of fluid and one for the cannula 250 for outflow of fluid. When the surgery is to include use of the shaver handpiece 52, then an additional incision to those mentioned above must be made.

The pump cassette 198, being disposable, allows for the insertion and attachment of all required tubing and surgical instruments prior to insertion into the cavity. Once the patient has been prepared, the pump cassette 198 is inserted through the access door 196 of the intra-articular unit 14 and coupling of the motor drivers 210 and 214 with the gear pumps 222 and 224 respectively is accomplished. In addition, the proximity pressure sensor 218 is positioned proximate to the pressure dome 234. The imaging unit 12 and the intra-articular unit 14 are then switched on and operation of the apparatus 10 begins.

The surgeon selects a fixed flow rate for the irrigation pump 222 and a desired pressure to be maintained within the cavity either by front panel controls on the intra-articular unit 14 or by the remote control unit 18. The irrigation pump 222 begins pumping fluid from the fluid supply 246 to the cavity. The pressure within the cavity is monitored by the pressure sensor 218 reacting to the proximity of the pressure dome 234. As the pressure within the cavity increases, the pressure dome 234 expands and moves closer to the pressure sensor 218. The pressure sensor 218, being a proximity sensor, senses the change in location of the pressure dome 234 and converts the position of the pressure dome 234 into a corresponding pressure signal. Once the predetermined pressure set by the surgeon is reached, the aspiration pump 224 begins pumping fluid from the cavity through the tube 240 and the check valve 226, through the output port 224b2, through the check valve 230, and through the tube 242 to the drain reservoir 252. The speed of the aspiration pump 224 is responsive to the pressure sensor 218 and provides for a constant pressure within the cavity regardless of the leakage which may occur.

The operation continues with the irrigation pump 222 pumping at a fixed flow rate and the pressure sensor 218 maintaining a specified pressure within the cavity by controlling the speed of the aspiration pump 224. If the surgeon desires a higher pressure with the cavity, the desired selection may be made by either a switch on the front panel 50 or by the remote control unit 18. Similarly, if the surgeon desires a lower pressure, that selection is also made by a switch on the front panel 50 or the remote control unit 18. When a higher pressure is selected, the speed of the aspiration pump 224 is slowed until the higher pressure is reached. When a lower pressure is selected, the speed of the aspiration pump 224 is increased until the lower pressure is reached. In a similar fashion, the surgeon can increase or decrease the flow rate of the irrigation pump 222 by using additional switches located on the front panel 50 or the remote control unit 18. When an increase or decrease in the flow rate is selected, the pressure sensor 218 maintains the desired pressure within the cavity by controlling the speed of the aspiration pump 224.

When the surgeon has selected to use the shaver handpiece 52, the fluid within the cavity is also withdrawn through the shaver handpiece 52 in a manner described below so as to cause a change in the flow of fluid leaving the cavity. In addition, the flow rate of fluid may have to be increased to provide for the flushing of debris or blood. This increased inflow rate and the switching of outflow of fluid to go through the shaver handpiece 52 occurs automatically with the activation of the shaver handpiece 52. In this regard, when the shaver handpiece 52 is activated, the direction of the aspiration pump 224 is reversed and the speed of the irrigation pump 222 is set to a predetermined (usually higher) flow rate. The reversing of the aspiration pump 224 changes the input from the tube 240 and the check valve 226 to the tube 244 and the check valve 232. The outflow is changed from the check valve 230 to the check valve 228. As can be seen from FIG. 10, both the check valve 228 and the check valve 230 are in communication with the tube 242, which is in communication with the drain reservoir 252. During the increase in flow rate and switching of inputs to the aspiration pump 224, the pressure sensor 218, working in conjunction with the pressure dome 234, maintains the preselected pressure within the cavity. Upon deactivation of the shaver handpiece 52, the system reverts back to the operation as described above.

The shaver handpiece 52 can be controlled by front panel controls on the intra-articular unit 14 or by the remote control unit 18. In either instance, the speed of the shaver handpiece 52 can be adjusted by suitable push button switches to either increase or decrease the shaver speed, and to control start and stop operation of the shaver handpiece.

Figure 11:
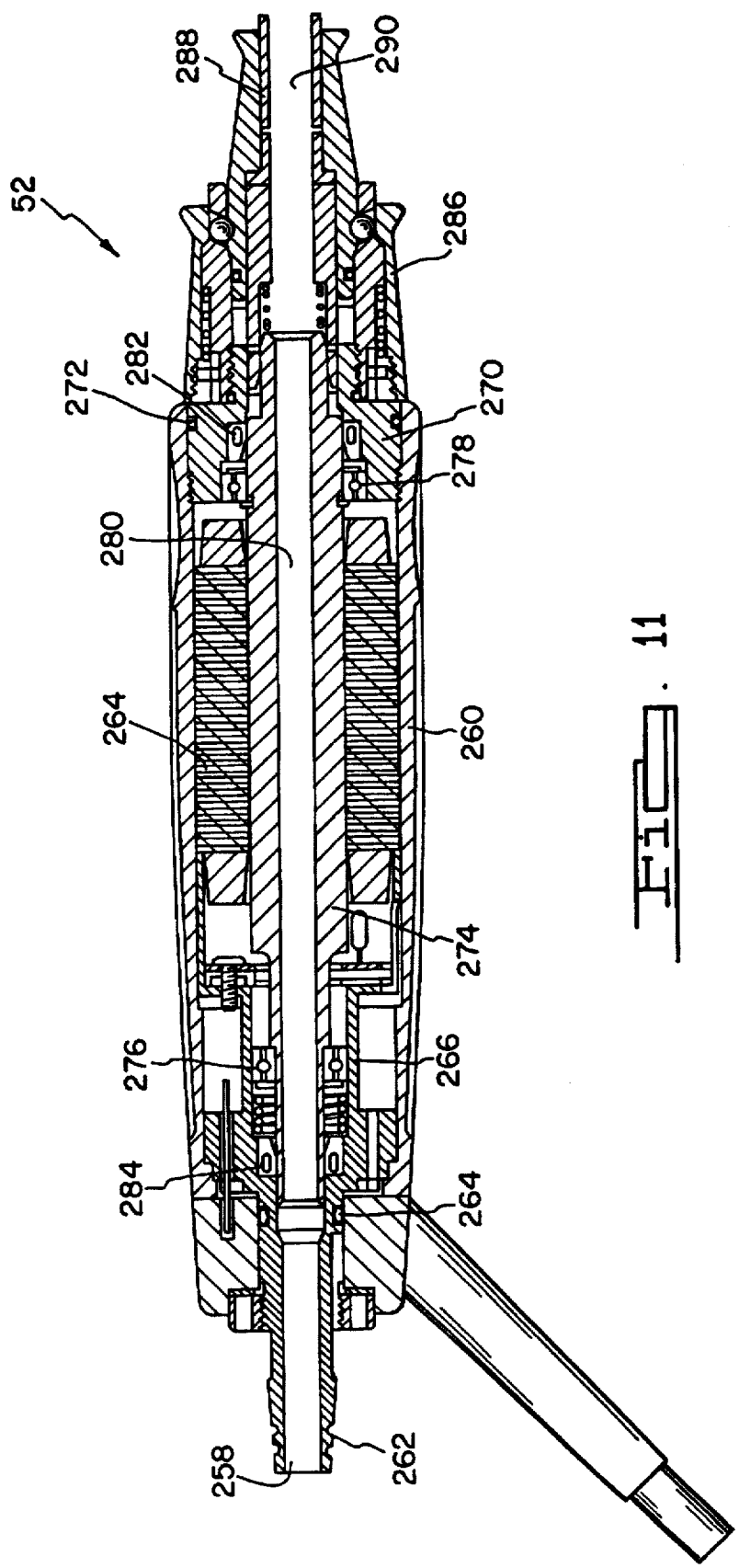
FIG. 11 is a longitudinal cross sectional view partially in cross-section of the shaver handpiece unit shown in FIG. 1 according to the preferred embodiment of the present invention.

Referring now to FIG. 11, an enlarged longitudinal cross-section of the shaver handpiece 52 is shown. The shaver handpiece 52 comprises a generally hollow cylindrical housing 260. An aspiration port 262 is located toward the rear end of the housing 260 and provides a connecting port for the tube 232. A seal 264 is located between the aspiration port 262 and the housing 260 to seal the internal portion of the housing 260. The aspiration port 262 has a hollow bore 258 to provide for the movement of fluid as will be described later herein. A motor stator 264 is positioned in the housing 260 using an interference fit between the motor stator 264 and the inside diameter of the housing 260. A frame 266 is positioned between the aspiration port 262 and the motor stator 264 within the housing 260. The frame 266 axially locates the motor stator 264 within the housing 260. An end cap 270 is fixedly secured to the end of the housing 260 opposite the aspiration port 262 to enclose the interior portion of the housing 260. A seal 272 located between the housing 260 and the end cap 270 seals the interior portion of the housing 260 from the outside environment. A hollow motor rotor 274 is rotatably positioned within the housing 260 and the motor stator 266 by a pair of bearings 276 and 278. The bearing 276 rotatably mounts the rear end of the motor rotor 274 relative to the frame 266. The bearing 278 rotatably mounts the front end of the motor rotor 274 relative to the end cap 270. The motor rotor 274 has a hollow bore 280 which is in communication with the hollow bore 258 for the movement of fluid. A pair of seals 282 and 284 seal the interior of the housing 260.

A chuck 286 is fixedly attached to the open end of the end cap 270 and provides for the quick change of the various shaver blades 288 which are needed during the procedure. The shaver blades 288 can include a full radius shaver of various sizes, a synovial resector, a meniscus cutter, a flat end cutter, a round end cutter, a side cutter, a slotted whisker cutter, a round abrader, a tapered abrader, as well as a wide variety of other shaver blades. The shaver blades 288 have a hollow bore 290 which is in communication with the hollow bore 280 of the motor rotor 274 when the shaver blade 288 is locked into the shaver handpiece 52 by the chuck 286. Locking the shaver blade 288 into the shaver handpiece 52 by the chuck 286 also connects the shaver blade 288 with the motor rotor 274 for rotation therewith.

Upon activation of the shaver handpiece 52, the motor rotor 274 rotates the blades 288 to perform the necessary operation on the patient. Activation of the shaver handpiece 52 also switches the outflow of fluid from the cavity from a separate cannula to the shaver handpiece 52 as previously described. Fluid withdrawn from the cavity travels through the hollow bore 290, through the hollow bore 280, through the hollow bore 258 and into the tube 232. During the aspiration of fluid from the cavity, the direction of travel of fluid through the shaver handpiece 52 is in a generally straight line. The design of the shaver handpiece 52 eliminates the need for the fluid to travel around corners which tend to cause clogging of the aspiration path. The generally straight path formed within the shaver handpiece 52 insures a free flow of fluid from the cavity and minimizes the tendency of the aspiration path to clog.

Figure 12:
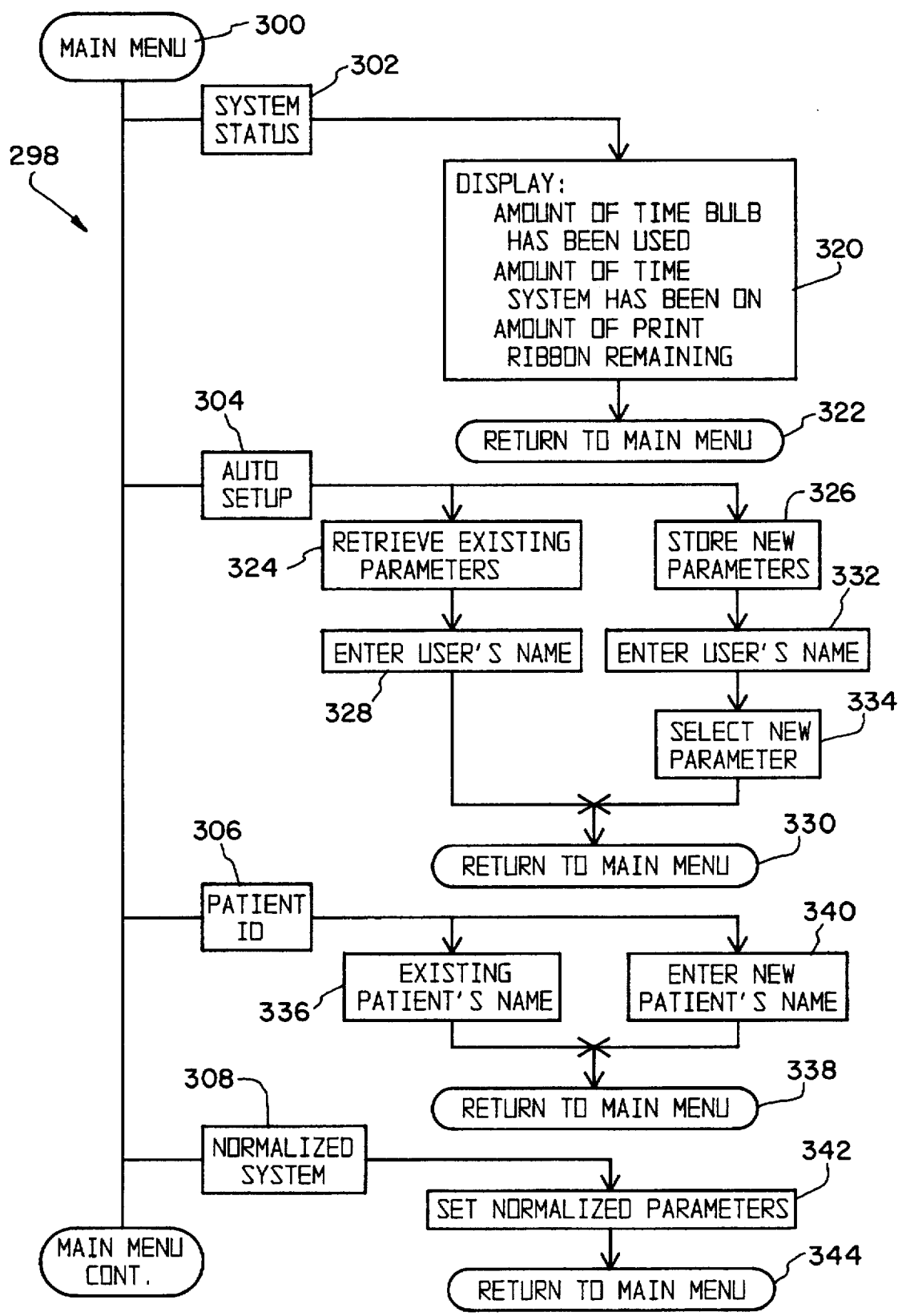
FIGS. 12–14 show a flowchart illustrating the various user-driven menus which are generated by the apparatus for performing endoscopic surgical procedures shown in FIG. 1 according to the preferred embodiment of the present invention.
Figure 13:
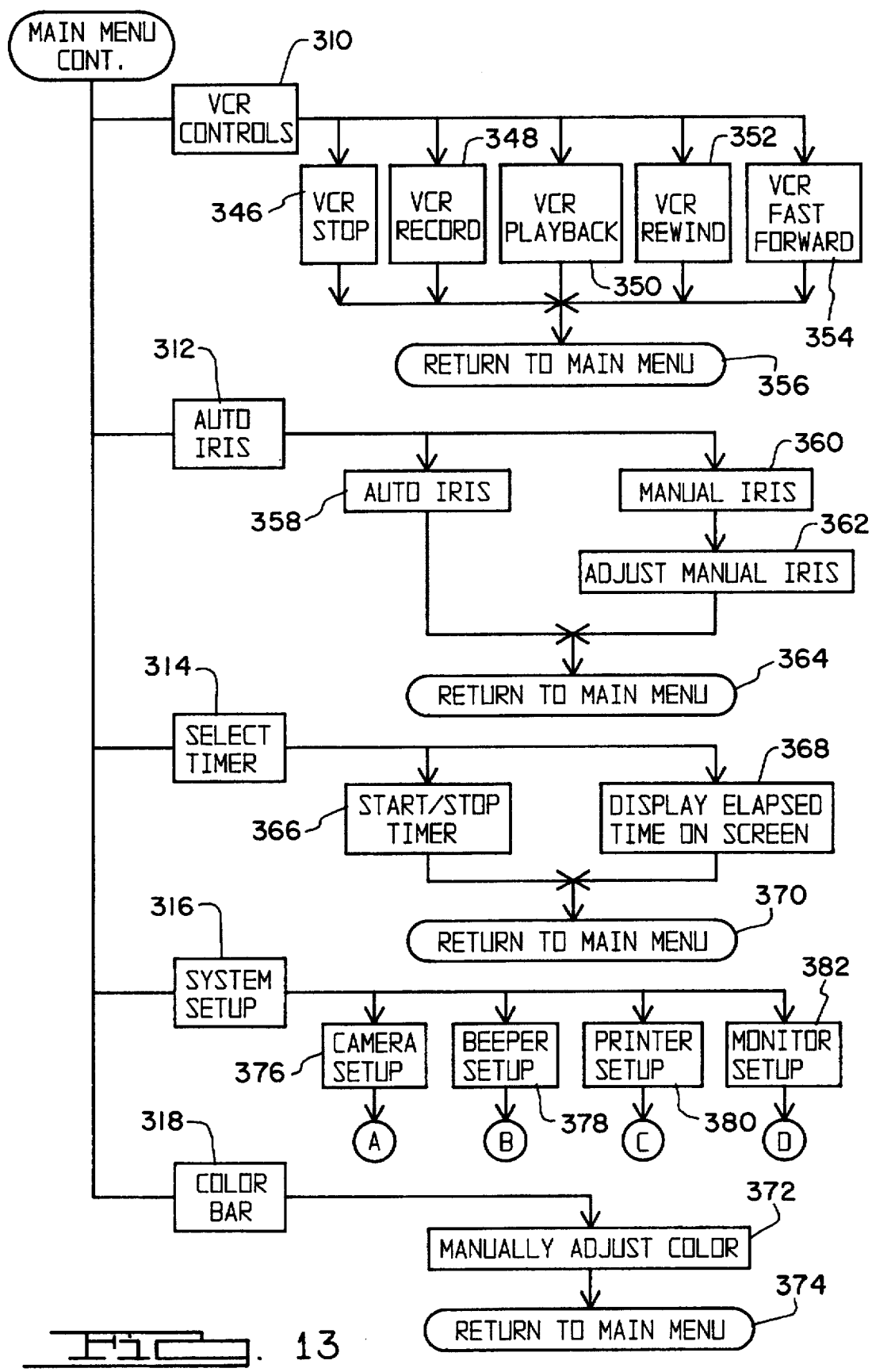
Figure 14:
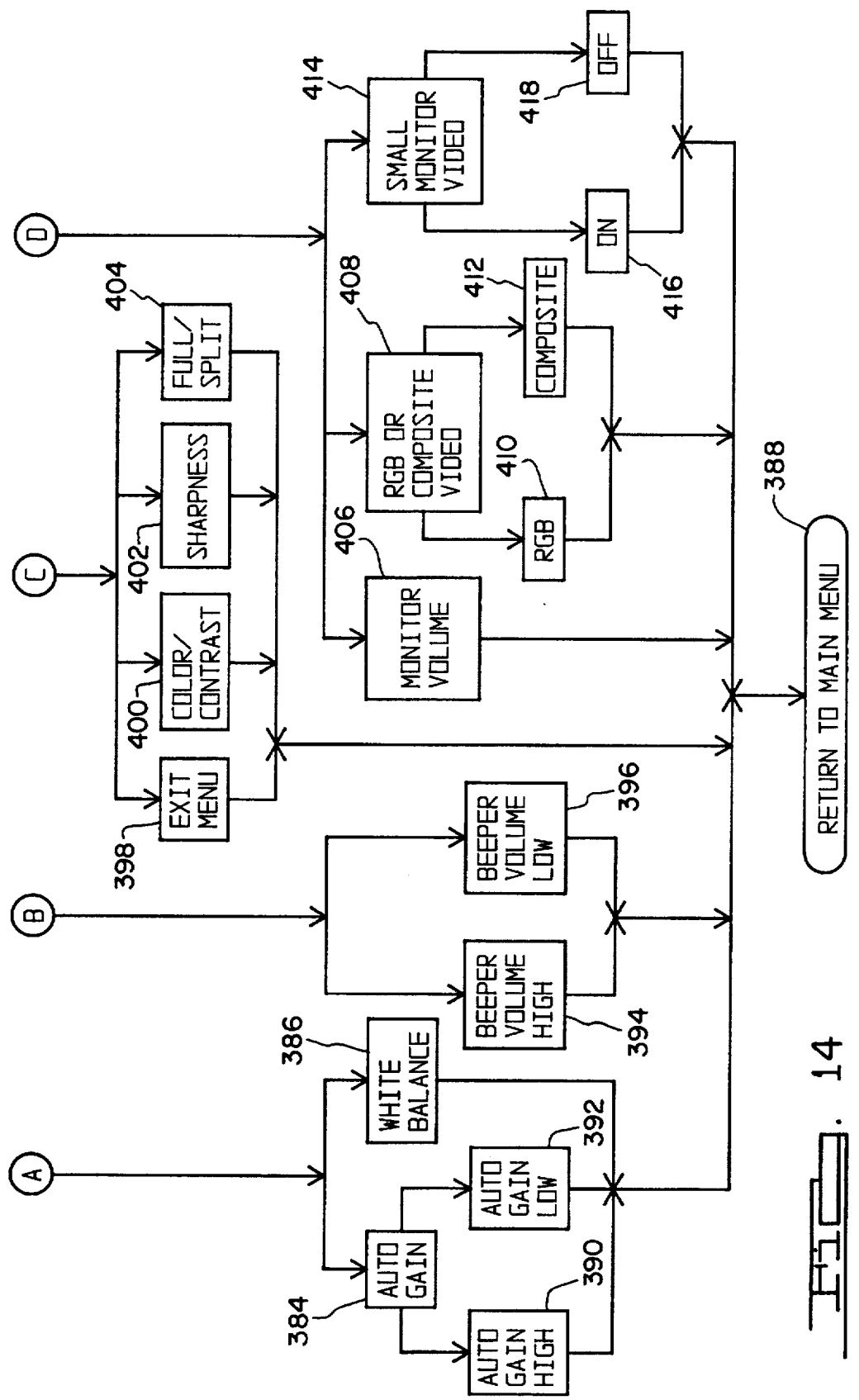

Referring now to FIGS. 12–14, there is shown a simplified flowchart 298 of the menu-driven software of the apparatus 10 of the present invention. After power up of the apparatus 10, the user may select a main menu 300 having the following nine fields representing options by which the user can adjust or set up the apparatus 10 to suit a variety of particular preferences and/or for a variety of operating parameters:

System status
    Auto setup
    Patient ID
    Normalized system
    VCR controls
    Auto iris
    Select Timer
    System setup
    Color bar The user selects one of the above nine mentioned options 302–318 by using either the keyboard 16, the remote control unit 18 or the front panel controls of the imaging unit 12. If the system status 302 option is selected, then the RGB monitor 30 of the imaging unit 12 displays the amount of time the bulb of the camera head 38 has been used (in hours), the amount of time the apparatus 10 has been on and the amount of print ribbon remaining in the video printer 24, as indicated at block 320. Accordingly, if the time of use of the bulb indicates that the bulb should be changed, or if the amount of print ribbon left indicates that the print ribbon should be changed, these items can be attended to before beginning the surgical procedure. The system 298 then returns to the main menu 300, as indicated by block 322.

If the auto setup 304 option is selected, the user is presented with the choice of either retrieving existing operating parameters as indicated by block 324, stored in the apparatus 10 or storing new operating parameters, as indicated by block 326, for the apparatus 10. If the existing parameters are to be used, then the user merely enters his/her name, as indicated by block 328, and the system 298 returns to the main menu 300, as shown by block 330. If the user desires to store new operating parameters, then the user selects and stores the new parameter(s), as indicated by the block 326, enters his/her name, as indicated by the block 332, then selects new parameters, as indicated by the block 334. This associates the new parameters with the entered user's name and may be recalled at future times by merely entering the user's name. The system 298 then returns to the main menu 300 as indicated by the block 330.

If the user selects the select patient ID field 306, then a menu showing the existing patient's name is displayed, as indicated at the block 336, and the system 298 returns to the main menu 300 as indicated by the block 338. If the user desires to enter a new patient name, then this option is provided, as indicated by the block 340, whereby the system 298 will store the new patient name entered before returning to the main menu 300, as indicated by the block 338.

If the normalized system option 308 is selected, then the system 298 automatically resets all of the operating parameters previously stored to default selections, as indicated at the block 342, before returning to the main menu 300, as indicated by block 344.

If the select VCR controls option 310 is selected by the user, a menu displaying options to select either VCR stop 346 to stop recording or playback operation of the video cassette recorder 22, enabling VCR recording 348, initiating VCR playback 350, initiating rewind 352, and initiating VCR fast forward operation 354 are provided. After the user selects the desired option the system 298 returns to the main menu 300 as shown by block 356.

If the user selects the auto iris option 312 from the main menu 300, the user will be presented with a menu displaying the option of having the iris adjustment performed automatically, as indicated by the block 358, or the option of manually adjusting the iris, as indicated by the block 360. If the manual iris adjustment option 360 is selected, the user is allowed to manually adjust the iris, as indicated by the block 362, before the system 298 returns to the main menu 300, as indicated by the block 364. If the auto iris option 358 is selected, the system 298 automatically adjusts the iris before returning to the main menu, as indicated by the block 364.

If the select timer option 314 is selected, then a menu is displayed which provides the user with the option of starting or stopping a timer for timing the surgical procedure, as indicated by the block 366, or displaying the elapsed time of the timer on the RGB monitor 30, as indicated by the block 368, before the system returns to the main menu 300, as shown by the block 370.

If the select system setup option 316 is selected, then the user is presented with a variety of options for setting up the various peripherals of the system 10, as will be described momentarily in connection with FIG. 14. Finally, if the color bar option 318 is selected by the user, a color bar is displayed on the RGB monitor 30 which can then be manually adjusted, as indicated by the block 372, before proceeding with the surgical procedure, before returning to the main menu 300, as indicated by the block 374.

Referring now to FIGS. 13 and 14, the options presented to the user if the system setup 316 option is selected from the main menu 300 are shown. When the system setup 316 option is selected, the user is presented with another menu having a camera setup 376 option, a beeper setup 378 option, a printer setup 380 option, and a monitor setup 382 option. If the camera setup 376 option is selected, then the user is presented with another menu which displays the choice of adjusting the auto gain of the camera head 38, as indicated by the block 384, or adjusting the white balance of the camera head 38, as indicated by the block 386, before returning to the main menu, as shown by the block 388. If the auto gain adjustment is selected, as indicated by the block 384, then the user is presented with yet another menu displaying the options of increasing the auto gain setting, as indicated by the block 390, or decreasing the auto gain setting, as indicated by the block 392, before the system 298 returns to the main menu 300.

If the user selects the beeper setup 378 option, then the user is presented with another menu displaying the option of increasing the beeper volume, as indicated by the block 394, or decreasing the beeper volume, as indicated by the block 396, before the system 298 returns to the main menu 300.

If the user has selected the printer setup 380 option, then another menu is displayed showing the option of exiting the current menu, as shown by the block 398, the option of setting the color/contrast of the printer 24 as shown by the block 400, the option of setting the sharpness of the printer 24, as shown by the block 402 and the option of selecting either a full or split printout, as indicated by the block 404 are provided. After selecting one of the four above mentioned options, the system 298 returns to the main menu 300, as shown by the block 388.

If the user has selected the monitor setup 382 option, then the system 298 displays a menu having four options. The first option is a monitor volume option, indicated by the block 406, which enables the volume of the RGB monitor 30 to be adjusted before returning to the main menu 300. An RGB or composite video option, as indicated by the block 408, if selected, causes another menu to be generated from which either RGB or composite video may be selected, as indicated by the blocks 410 and 412, respectively, before the system 298 returns to the main menu 300. A small monitor video option, indicated by the block 414, if selected, enables video display of the surgical procedure on the RGB monitor 30, as indicated by the block 416 or allows the RGB monitor 30 to be turned off, as indicated by the block 418, before returning to the main menu 300.

Accordingly, the above-described, menu-driven software system provides a means by which the various operating parameters and peripherals may be adjusted and/or selected quickly and easily by the user either before the surgical procedure is under way or during the procedure. The various menus of the system 298 enable a wide variety of operational parameters to be changed quickly and also without interrupting the surgical procedure once started.

While the above detailed description describes the preferred embodiment of the present invention, it should be understood that the present invention is susceptible to modification, variation and alteration without deviating from the scope and fair meaning of the subjoined claims.

APPENDICES

APPENDIX A:

LISTING OF THE SUBROUTINES USED WITH IMAGING
UNIT 12 SHOWING NESTINGS OF THE SUBROUTINES.

```
1.0 COLD
        1.00 BUFINIT
            1.000 FLUSHIN
            1.001 FLUSHOUT
        1.01 SIOINIT
        1.02 DTRINIT
        1.03 MONSEL
        1.04 DTRSET
        1.05 SYNCSEL 1.1 ENTRY
        1.10 SIORXEN
        1.11 PARMSET
            1.110 PUTPARM
            1.111 PARMLOAD
            1.112 PARMGET
        1.12 DTRSET
        1.13 MEMFILL 1.2 CLS
        1.20 DSPYON
        1.21 BLANKROW
            1.210 DISCHAR
                1.2100 SMULT
            1.211 ROWCOLOR 1.3 WARM
        1.30 CBAR
            1.300 DISINIT
            1.301 ROWCOLOR
            1.302 DMESS
                1.3020 ROWCOLOR
                1.3021 MESS
                    1.30210 SMULT
        1.31 DISPLAY
            1.310 VSYNCW
                1.3100 SIOOUT
                1.3101 FATAL
                    1.31010 CLS
                    1.31011 ROWCOLOR
                    1.31012 DTRSET
                    1.31013 HEXASCL
                        1.310130 BINBCD
                    1.31014 MESS
                        1.310140 SMULT
                    1.31015 DISPLAY
```

```
                        1.310150  VSYNCW
                            1.3101500  SIOOUT 1.31016  BEEPER
                        1.310160  BEEP 1.4  EXRAMTEST
     1.40  FATAL (1.3101)

1.5  IRAMTEST
     1.50  FATAL (1.3101)

1.6  CKEPCRC
     1.60  GENCRC
     1.61  FATAL (1.3101)

1.7  EXSIO
     1.70  SIOPUT
     1.71  SIOGET
     1.72  GETJUMP 1.8  GETDSR 1.9  CBAR
     1.90  DISINIT
     1.91  ROWCOLOR
     1.92  DSPYON
     1.93  DISLOAD 2.0  MNUESC
     2.00  CLS
     2.01  PIDEX
         2.010  ROWCOLOR
         2.011  CALCFILE
             2.0110  SMULT
         2.012  MCENTER
         2.013  MESSEX
             2.0130  SMULT 2.1  ETIMERN
         2.10  ETIMERM
             2.100  TOTALIZE
             2.101  HEXASC
                 2.1010  BINBCD
             2.102  ROWCOLOR
         2.11  ROWCOLOR 2.2  UPDATE
         2.20  GETPARM
         2.21  PUTPARM
```

```
2.3 PROPS
        2.30 PRMESS
                2.300 SIOPUT
        2.31 PRETURN
                2.310 SIOGET
                2.311 SIOPUT
        2.32 FLUSHIN
        2.33 SIOPUT
        2.34 DISPLAY (1.31015)

2.4 PRFZTERM
        2.40 PUTPARM
        2.41 PARMLOAD
        2.42 CLS
        2.43 DRIBBON
                2.430 CLS
                2.431 MNUBLOCK
                2.432 DISTYPE
                        2.4320 GETJUMP
                2.433 EXRTSND
                        2.4330 CLSNB
                        2.4331 PIDEX
                                2.43310 ROWCOLOR
                                2.43311 CALCFILE
                                        2.433110 SMULT
                                2.43312 MCENTER
                                2.43313 MESSEX
                                        2.433111 SMULT 2.5 PRINTERR
        2.50 FLUSHIN
        2.51 FLUSHOUT
        2.52 DISPRE
                2.520 MNUBLOCK
                2.521 CLS
                2.522 DISTYPE (2.432)

2.6 MONITOR
        2.60 MONSEL
        2.61 SYNCSEL 2.7 DISPLAY (1.31015)

2.8 EXSIO (1.7)

2.9 STANDBY
    2.90 EXSIO (1.7)
    2.91 VSYNCW (1.310)
```

```
3.0 GETDSR 3.1 LOGO
      3.10 DSPYON
      3.11 DISCLEAR
            3.110 BLANKROW
                  3.1100 DISCHAR
                        3.11000 SMULT
                  3.1101 ROWCOLOR
      3.12 DISLOAD
      3.13 LOGONBX
            3.130 MESS
                  3.1301 SMULT
            3.131 ROWCOLOR
            3.132 DSPYON 3.2 MNUESC
      3.20 CLS
      3.21 PIDEX (2.4331)

3.3 ETIMERN (2.1)

3.4 UPDATE (2.2)

3.5 PCONNECT 3.6 PROPS (2.3)

3.7 PRFZTERM (2.4)

3.8 PRINTERR (2.5)

3.9 MONITOR (2.6)

4.0 DISPLAY (1.31015)

4.1 EXLAMP
    4.10 DTRSET 4.2 SYSINIT
    4.20 MEMFILL
    4.21 MEMMOVE
    4.22 EXNORM
          4.220 PARMSET (1.11)
          4.221 CLS
          4.222 MESSTO
                4.2220 CLS
                4.2221 DMESS
```

```
                              4.22210 ROWCOLOR
                              4.22211 MESS
                                      4.222110 SMULT
        4.23 DMESS (4.2221)
        4.24 DISPLAY (1.31015)

4.3 DISCLEAR
    4.30 BLANKROW 4.4 DISTATUS
    4.40 MNUBLOCK
    4.41 DISTYPE
         4.410 GETJUMP
    4.42 DMESS (4.2221)

MAIN LOOP 4.5 EXSIO (1.7)

4.6 STANDBY (2.9)

4.7 SWITCHOP
    4.70 REMKEY
         4.700 REMSCAN
    4.71 UUPARMOP
    4.72 FPSWIN
         4.720 GETDSR
    4.73 SWITCHES
         4.730 MENUUP
               4.7300 MNUBLOCK
               4.7301 VLIMIT
               4.7302 CBAREXIT
                      4.73020 DISINIT
                      4.73021 EXRTSND (2.433)
         4.731 MENUDN
               4.7310 MNUBLOCK
               4.7311 VLIMIT
               4.7312 CBAREXIT
                      4.73120 DISINIT
                      4.73121 EXRTSND (2.433)
         4.732 KTIMER
         4.733 MNUESC
               4.7330 CLSNB
               4.7331 PIDEX (2.4331)
         4.734 MNUOPEX
               4.7340 MNUBLOCK
               4.7341 DISTYPE (2.432)
         4.735 GETJUMP
         4.736 CLS
```

```
4.737 MNUBLOCK
4.738 DISTYPE (2.432)
4.739 PARMLOAD
4.740 PUTPARM
4.741 DISPRE (2.52)
4.742 IDOPS
     2.7420 IDMOVE
          2.74200 SMULT
     2.7421 PIDLOAD
     2.7422 SUMOVE
     2.7423 SUSTORE
     2.7424 DBLOCK3
          2.74240 DSPYON
          2.74241 CLEARROW
               2.742410 ROWCOLOR
               2.742411 MESS
          2.74242 SMULT
          2.74243 ROWCOLOR
          2.74244 MESSEX
               2.742440 SMULT
2.743 PIDOPS
     2.7430 IDMOVE (2.7420)
     2.7431 PIDLOAD
     2.7432 CLROW0
     2.7433 CLIDBUF
     2.7434 DBLOCK3 (2.7424)
2.744 MESSTO (4.222)
2.745 PIDEX (2.4331)
2.746 ROWCOLOR
2.747 MESSEX (2.74244)
2.748 WANDC
     2.7480 CAPMOVE
          2.74800 SMULT
     2.7481 PARMLOAD
     2.7482 MEMFILL
2.749 CAPDIS
     2.7490 ROWCOLOR
     2.7491 MESSEX (2.74244)
2.750 DISCHAR
     2.7500 SMULT
2.751 CLROW0
2.752 CFFULL
     2.7520 ROWCOLOR
     2.7521 MESS
          2.75210 SMULT
     2.7522 CLIDBUF
2.753 CLIDBUF
2.754 IDERASE
     2.7540 SMULT
```

```
              2.755 SUERASE
                   2.7550 SMULT
              2.756 DBLOCK3 (2.7424)
              2.757 GUUCRC
                   2.7570 GENCRC
              2.758 SIOPUT
              2.759 SENDDAT
                   2.7590 SIOPUT
              2.760 FLUSHOUT
              2.761 PARMGET 4.8 MNUESC (4.733)

4.9 KEYBDOP
         4.90 FLUSHIN
         4.91 CLIDBUF
         4.92 GETKB
              4.920 SIOGET
              4.921 SIOPUT
         4.93 ROWCOLOR
         4.94 DISCHAR (2.750)

5.0 ETIMERN (2.1)

5.1 UPDATE (2.2)

5.2 PCONNECT 5.3 PROPS (2.3)

5.4 PFZTERM (2.4)

5.5 NORMTERM
         5.50 EXRTSND (2.433)

5.6 RECTERM
         5.60 EXRTSND (2.433)

5.7 VCRROVL
         5.70 CAPDIS
              5.700 ROWCOLOR
              5.701 MESSEX (2.74244)

5.8 VCRMESS
         5.80 MESS (2.7521)
         5.81 ROWCOLOR 5.9 PRINTERR (2.5)
```

```
6.0 POFFLINE
    6.00 FLUSHIN
    6.01 FLUSHOUT
    6.02 PARMSET (1.11)
    6.03 DISPRE (2.52)

6.1 SENDSB
    6.10 SBUSSGET
    6.11 FLUSHOUT 6.2 MONITOR
    6.20 MONSEL
    6.21 SYNCSEL 6.3 DISPLAY (1.31015)

6.4 BEEPER
    6.40 BEEP 6.5 WANDH
    6.51 FLUSHIN
    6.52 SIOPUT
    6.53 MEMFILL
    6.54 SIOGET 6.6 EXLAMP
    6.60 DTRSET 6.7 LOGONB
    6.70 MESS (2.7521)
    6.71 ROWCOLOR
    6.72 DSPYON 6.8 UUPGET
    6.80 SIOGET
    6.81 SIOPUT
    6.82 GENCRC
    6.83 PARMLOAD
    6.84 FLUSHIN 6.9 HKEEP
    6.90 DTRSET

LOOP FOREVER MAIN
```

45

Additional nesting from Interrupts 7.0 VSYNCIPT             ;INTERRUPT ON DISPLAY VERTICAL RETRACE 7.1 SIOIPT               ;INTERRUPT ON RECEIVED SIO CHARACTER
    7.10 SBUSSIPT 7.2 RTCIPT               ;INTERRUPT ON REAL TIME CLOCK
    7.11 SBUSSIPT 7.3 SBUSSIPT             ;INTERRUPT ON S-BUSS CLOCK TIMER Table Executed Routines 7.4 EXPRE 7.5 EXPSTORE
    7.50 EXPRE 7.6 EXPRNT
    7.60 EXPRE 7.7 EXPRUFZ
    7.70 EXPRE 7.8 EXIRIS
    7.80 DTRSET 7.9 EXPRSH
    7.90 EXPRE 8.0 DBLOCK5
    8.00 DSPYON
    8.01 ROWCOLOR
    8.02 HEXASCL
        8.020 BINBCD
    8.03 SMULT
    8.04 MESS (2.7521)

8.1 IDSEL
    8.10 CLIDBUF
    8.11 MNUBLOCK
    8.12 DISTYPE (2.432)

```
8.2 EXPRFOR
    8.20 EXPRE 8.3 EXBEEPVS 8.4 EXCADJ
    8.40 EXPRE 8.5 EXAUTOI
    8.50 PARMSET (1.11)
    8.51 DTRSET 8.6 CBARON
    8.60 CLS
    8.61 DISINIT
    8.62 ROWCOLOR
    8.63 DISLOAD
    8.64 MNUBLOCK
    8.65 DSPYON 8.7 EXVCRLO
    8.70 VCRLOUT
        8.71 DISPRE (2.52)
        8.72 PARMLOAD
        8.73 MNUBLOCK
        8.74 DISTYPE (2.432)

8.8 EXSMV
    8.80 EXRTS
        8.800 CLSNB
            8.8000 BLANKRNB
                8.80000 ROWCOLOR
                8.80001 MESS (2.7521)
            8.8001 DSPYON 8.9 PIDCAP
    8.90 CAPLOAD
        8.900 CALCFILE
        8.901 CAPMOVE
            8.9010 SMULT
        8.902 PARMLOAD
    8.91 EXRTSND (2.433)

9.0 EXRTS
    9.00 CLSNB (8.800)
    9.01 DBLOCK4
        9.010 DSPYON
        9.011 ROWCOLOR
        9.012 HEXASCS
```

```
              9.0120 HEXASC
         9.013 SMULT
         9.014 MCENTER
         9.015 MESS (2.7521)

9.1 EXAGAIN
    9.10 PARMGET 9.2 EXPFONT
    9.21 EXPRE 9.3 EXCFONX
    9.30 EXPRE
    9.31 EXCADJ
         9.310 EXPRE 9.4 EXTSET
    9.40 MNUBLOCK
    9.41 DISTYPE (2.432)

9.5 RECALLI
    9.50 PARMSET (1.11)
    9.51 CLS
    9.52 DMESS (4.2221)
    9.53 AUTOIDX
         9.530 ROWCOLOR
         9.531 CALCFILE
         9.532 MCENTER
         9.533 MESSEX (2.74244)
    9.54 MESSTO (4.222)

9.6 AUTOIDX (9.53)

9.7 RECALLID
    9.70 CALCFILE
    9.71 CAPMOVE
         9.710 SMULT
    9.72 PARMGET
    9.73 RECALLI (9.5)

9.8 DBLOCK6
    9.80 DBLOCK2 (10.0)

9.9 EXTIM
```

```
10.0 DBLOCK2
     10.00 DSPYON
     10.01 ROWCOLOR
     10.02 HEXASCS (9.012)
     10.03 MCENTER
     10.04 MESS (2.7521)

10.1 DBLOCK3 (2.7424)

10.2 DBLOCK4 (9.01)

10.3 DBLOCK7
     10.30 DSPYON
     10.31 CLEARROW (2.74241)

10.4 EXCAMS
     10.40 MNUBLOCK
     10.41 DISTYPE (2.432)

10.5 EXCCD
     10.50 EXPRE
     10.51 PARMLOAD 10.6 EXMONVOL
     10.60 PARMGET
     10.61 SBCTRL
           10.610 SIOPUT 10.7 EXMSEL
     10.70 PARMGET
     10.71 SBCTRL (10.61)

10.8 EXPON
     10.80 PARMGET
     10.81 PARMLOAD
     10.82 SBCTRL (10.61)

10.9 EXPRCLM
     10.90 SBCTRL (10.61)

10.10 EXPRFP
      10.100 EXPRE 10.11 EXPRGRL
      10.110 EXPRE 10.12 EXPRIPOS
      10.120 EXPRE
```

```
10.13 EXPRVPR
    10.130 MNUBLOCK
    10.131 DISTYPE (2.432)
    10.132 DISPRE (2.52)

10.14 EXSENDC
    10.140 EXPRE 10.15 EXSEV
    10.150 EXPRE 10.16 EXSFI
    10.160 PARMLOAD
    10.161 PUTPARM
    10.162 MNUBLOCK
    10.163 DISTYPE (2.432)

10.17 EXVCREX
    10.170 PARMGET
    10.171 SBCTRL (10.61)

10.18 EXVCROP
    10.180 VCRLOUT
        10.1800 DISPRE
    10.181 EXRTS (8.80)

10.19 EXWHBAL
    10.190 DTRSET
    10.191 EXRTS (8.80)

10.20 SBCTRL (10.61)

10.21 VCRLOUT
    10.210 DISPRE (2.52)

10.22 CAPLOAD
    10.220 CALCFILE
    10.221 CAPMOVE (9.71)
    10.222 PARMLOAD 10.23 HEXASCS (9.012)
```

APPENDIX B:

DESCRIPTION OF THE PROGRAM USED WITH THE IMAGING UNIT 12

1. MAIN ROUTINE

The MAIN routine is the top level routine for the imaging unit 12. A listing of MAIN is reproduced below. The portions of MAIN labeled MAINY, MAIN0, MAIN1 and MAIN1A are for initialization, while the portions MAIN1AA and MAIN1AB are for self-testing. In addition, the portions labeled MAIN1AB, MAIN1B and MAIN2 represent the warm-up procedure, while the portion identified as MAIN3 represents the main functional loop of MAIN.

```
        DW   0                   ;1ST 2 LOCATIONS RESERVED
;Interrupt Vectors.

;VSYNC IPT IRQ1 (0002H)
;This interrupt occurrs each VSYNC.

DW VSYNCIPT              ;VSYNC IPT VECTOR

;SPARE IPT IRQ2 (0004H)
;This interrupt is not used.

DW GUARD                 ;GUARDED MEMORY OR I/O

;SIO IPT IRQ3 (0006H)
;This interrupt services the SIO.

DW SIOIPT                ;SIO IPT VECTOR

;RTC IPT IRQ4, TIMER T0 (0008H)
;This interrupt services the real time clock.

DW RTCIPT                ;RTC IPT VECTOR

;S BUSS IPT IRQ5, TIMER T1 (000AH)
;This interrupt services the C buss generator.

DW SBUSSIPT              ;S BUSS IPT VECTOR

;RESET (000CH)
;This is the CPU reset vector.

MAINY:
        LD PORT01,#P01_MODE      ;INIT PORT 1
        LD PORT02,#P02_MODE      ;INIT PORT 2
        LD PORT03,#P03_MODE      ;INIT PORT 3
        LD STK_LSB,#STK_TOP      ;INIT STACK PTR
        LD STK_MSB,#0
        SRP #WRB0                ;SET REG BANK #0
```

```
                LD 0D0H,#F0H                ;-> EMULATOR OVER-LAY
                LD 0D1H,#01H
                LD I_IPR,#IPR_MODE          ;INIT INTERRUPT PRIORITY
                LD I_IMSK,#IMR_MODE         ;INIT INTERRUPT MASK

CALL COLD                   ;COLD START INITIALIZE
MAIN0:
                ;JR MAIN0
MAIN1:
                CALL ENTRY
                CALL CLS
MAIN1A:                                     ;INIT LOOP
                CALL WARM                   ;WARM-UP #1
MAIN1AA:
                CALL ERAMTEST               ;EXT RAM TEST
                CALL IRAMTEST               ;INT RAM TEST
                LD R4,#0FFH                 ;CRC TEST
                CALL CKEPCRC
                LD R0,FLAG10
                AND R0,#38H
                CP R0,#38H
                JR NZ,MAIN1AA               ;LOOP UNTIL TESTS COMPLETE
MAIN1AB:
                CALL WARM                   ;WARM-UP #2
                CALL WARM                   ;WARM-UP #3
                CALL WARM                   ;WARM-UP #4
                CALL WARM                   ;WARM-UP #5
                INC INITDSPY                ;NEXT MESSAGE
                CALL WARM                   ;SELF TEST
                INC INITDSPY                ;NEXT MESSAGE

CALL WARMSET                ;SET-UP #1
                AND FLAG4,#0FEH             ;RESET CBAR
                CALL WARMSET                ;SET-UP #2
                AND FLAG4,#0FEH             ;RESET CBAR
                CALL WARMSET                ;SET-UP #3
MAIN1B:
                CALL EXSIO
                CALL STANDBY
                CALL GETDSR
                CALL LOGO                   ;SET-UP #4
                CALL MNUESC
                CALL ETIMERN
                CALL UPDATE
                CALL PCONNECT
                CALL PROPS
                CALL PRFZTERM
                CALL PRINTERR
                CALL MONITOR
                CALL DISPLAY
                CALL EXLAMP
                LD R0,FLAG4
                AND R0,#3
                CP R0,#3
                JR NZ,MAIN1B                ;LOOP UNTIL DONE
```

```
                CALL SYSINIT            ;INIT IF /IRQ2 LO

CALL DISCLEAR           ;CLEAR SCREEN
MAIN2:
                CALL DISTATUS
                LD UUSTATE,#3           ;DOWNLOAD SHAVER PARMS
MAIN3:
                OR FLAG6,#40H           ;MAIN LOOP SET
                CALL EXSIO
                CALL STANDBY
                CALL SWITCHOP
                CALL MNUESC
                CALL KEYBDOP
                CALL ETIMERN
                CALL UPDATE
                CALL PCONNECT
                CALL PROPS              ;PRINTER OPS
                CALL PRFZTERM
                CALL NORMTERM
                CALL RECTERM
                CALL VCRROVL
                CALL VCRMESS
                CALL PRINTERR
                CALL POFFLINE
                CALL SENDSB
                CALL MONITOR
                CALL DISPLAY
                CALL BEEPER
                CALL WANDH
                CALL EXLAMP
                CALL LOGONB
                CALL UUPGET
                CALL HKEEP
                JR MAIN3
```

2. EQUATE SECTION

The following is the Equate Section of the program associated with the imaging unit 12.

'EQ'

```
        Mapped I/O definition.
EMEM      EQU   4000H         ;EXTERNAL NON-VOLITILE RAM
CTC21     EQU   6000H         ;CTC #4 (PRINTER BAUD)
CTC22     EQU   6001H         ;CTC #5 (KEYBOARD BAUD)
CTC23     EQU   6002H         ;CTC #6 (SPARE)
CTC2CTRL  EQU   6003H         ;CTC #2 CONTROL
SIO1DATA  EQU   8000H         ;SIO #1 (WAND) DATA
SIO1CTRL  EQU   8001H         ;SIO #1 (WAND) CONTROL
SIO2DATA  EQU   8400H         ;SIO #2 (U-U) DATA
SIO2CTRL  EQU   8401H         ;SIO #2 (U-U) CONTROL
SIO3DATA  EQU   8800H         ;SIO #3 (EXT) DATA
```

```
SIO3CTRL    EQU     8801H           ;SIO #3 (EXT) CONTROL
SIO4DATA    EQU     8C00H           ;SIO #4 (PRINTER) DATA
SIO4CTRL    EQU     8C01H           ;SIO #4 (PRINTER) CONTROL
SIO5DATA    EQU     9000H           ;SIO #5 (KEYBOARD) DATA
SIO5CTRL    EQU     9001H           ;SIO #5 (KEYBOARD) CTRL
CTC11       EQU     0C000H          ;CTC #1 (WAND BAUD)
CTC12       EQU     0C001H          ;CTC #2 (U-U BAUD)
CTC13       EQU     0C003H          ;CTC #3 (EXT BAUD)
CTC1CTRL    EQU     0C003H          ;CTC #1 CONTROL
```

Internal Mapped I/O definition.

```
PWMMODE             EQU     0FC10H          ;PWM1-PWM8 OUTPUT PORT MODE
PWMOUT              EQU     0FC11H          ;PWM OUTPUT PORT REGISTER
PWM9                EQU     0FC1BH          ;BEEP VOLUME PWM PORT
PWM10               EQU     0FC1CH          ;AUTO IRIS PWM PORT
```

General register (internal ram).

```
INDEX0              EQU     04H             ;INDEX PTR TEMP (R4)
P3SAVE              EQU     05H             ;PORT #3 SAVE (R5)
P_PWMP              EQU     06H             ;PWM OUTPUT PORT SAVE
FPSWITCH            EQU     P_PWMP+1        ;FP SWITCH CODE
FPSLAST             EQU     FPSWITCH+1      ;LAST FP SWITCH CODE
UUCRC               EQU     FPSLAST+1       ;UU MESSAGE CRC
BEEPC               EQU     UUCRC+2         ;BEEP DURATION COUNTER
BEEPCMND            EQU     BEEPC+1         ;BEEP COMMAND
STATCOL             EQU     BEEPCMND+1      ;MENU DISPLAY TYPE 5 COLOR SELECT

FLAG0               EQU     STATCOL+1       ;FLAG #0
                                            ;D0 = PRINTER ADJUST DISPLAY MODE
                                            ;D1 = CBAR DISPLAY MODE
                                            ;D2 = CLEAR OR STORE MEMORY MODE
                                            ;D3 = UNFREEZE DISPLAY
                                            ;D4 = PRINT FREEZE ERROR
                                            ;D5 = VCR PLAY IN PROGRESS
                                            ;D6 = VCR RECORD IN PROGRESS
                                            ;D7 = VCR MODE MESSAGE DISPLAYED

PFMDLY              EQU     FLAG0+1         ;MONITOR UNFREEZE DELAY
```

Working register bank 0, program service.
10H-1FH

General register (internal ram).

```
RSCOL1      EQU     20H             ;REMOTE KEY COLUMN ARRAY (1-4)
RSCOL2      EQU     RSCOL1+1
RSCOL3      EQU     RSCOL2+1
RSCOL4      EQU     RSCOL3+1
IBINPTR     EQU     RSCOL4+1        ;SIO INPUT BUFFER INPUT PTR ARRAY
                                    ;WAND
                                    ;U-U
                                    ;EXT
                                    ;PRINTER
```

```
IBOUTPTR    EQU  IBINPTR+5      ;KEYBOARD
OBINPTR     EQU  IBOUTPTR+5     ;SIO INPUT BUFFER OUTPUT PTR ARRAY
                                ;SIO OUTPUT BUFFER INPUT PTR ARRAY

;WAND
                                ;U-U
                                ;EXT
                                ;PRINTER
                                ;CBUSS
OBOUTPTR    EQU  OBINPTR+5      ;SIO OUTPUT BUFFER OUTPUT PTR ARRAY
INSTAT      EQU  OBOUTPTR+5     ;SIO INPUT BUFFER STATUS ARRAY
                                ;0:0:0:0:0:X:F:E
                                ;E=EMPTY, F=FULL, X=RCVR ERRORS
                                ;WAND
                                ;U-U
                                ;EXT
                                ;PRINTER
                                ;KEYBOARD
OUTSTAT     EQU  INSTAT+5       ;SIO OUTPUT BUFFER STATUS ARRAY
                                ;0:0:0:0:0:B:F:E
                                ;E=EMPTY, F=FULL, B=BUSY
                                ;WAND
                                ;U-U
                                ;EXT
                                ;PRINTER
                                ;CBUSS
SIOCMRSV    EQU  OUTSTAT+5      ;SIO COMMAND WRITE ARRAY (1-5)
                                ;0:0:RTS:ER:SBK:RXE:DTR:TXEN
                                ;TXEN=1 ENABLE XMITTER
                                ;DTR=1      /DTR PIN =0
                                ;RXE=1      ENABLE RECEIVER
                                ;SBK=1      SEND BREAK
                                ;ER=1       RESET ERROR FLAG
                                ;RTS=1      /RTS PIN =0
EXDATA      EQU  SIOCMRSV+5     ;SIO EXECUTE DATA BUFFER
ROW         EQU  EXDATA+4       ;DISPLAY ROW POINTER
COL         EQU  ROW+1          ;DISPLAY COLUMN POINTER
ATEMP       EQU  COL+1          ;TEMPORARY
BTEMP       EQU  ATEMP+1        ;TEMPORARY
CTEMP       EQU  BTEMP+1        ;TEMPORARY
FLAG1       EQU  CTEMP+1        ;FLAG #1
                                ;D0 = RTC SECOND TICK
                                ;D1 = ELAPSED TIME DISPLAY ON
                                ;D2 = NORMAL DISPLAY PAGE ON
                                ;D3 = SHAVER DISPLAY PAGE ON
                                ;D4 = DISPLAY LOAD ENABLE
                                ;D5 = VERTICAL SYNC TICK
                                ;D6 = ELAPSED TIMER ON
                                ;D7 = MENU DISPLAY PAGE ON
FLAG2       EQU  FLAG1+1        ;FLAG #2
                                ;D0 = SHAVER ON LINE
                                ;D1 = TEMP
                                ;D2 = NON ZERO UU CODE SENT
                                ;D3 = PRINTER CONNECTED
                                ;D4 = PRINTER PRINTING
                                ;D5 = PRINTER ERROR
```

```
                              ;D6 = VIDEO LOAD TOGGLE
                              ;D7 = UPDATE COMPLETE
FLAG3        EQU   FLAG2+1    ;FLAG #3
                              ;D0 = AUTO ID FILE FULL
                              ;D1 = PATIENT ID FILE FULL
                              ;D2 = NULL ID ENTRY PATIENT ID
                              ;D3 = INVALID KEY CODE
                              ;D4 = PATIENT ID TOGGLE
                              ;D5 = MENU UP/DN/ENT KEY
                              ;D6 = 9 BYTE PRINT INQUIRE
                              ;D7 = VOLUME SET SHORT BEEP
FLAG4        EQU   FLAG3+1    ;FLAG #4
                              ;D0 = COLOR BAR TEST COMPLETE
                              ;D1 = LOGO TEST COMPLETE
                              ;D2 = MENU DISPLAY MODE ON
                              ;D3 = OVERLAY DISPLAY MODE
                              ;D4 = AUTO-IRIS SET DISPLAY MODE
                              ;D5 = PRINT-FREEZE DISPLAY MODE
                              ;D6 = WAND INPUT AVAILABLE
                              ;D7 = PATIENT ID MENU ON
FLAG5        EQU   FLAG4+1    ;FLAG #5
                              ;D0 = OP ERROR BEEP TOGGLE
                              ;D1 = KEYBOARD SHORT BEEP
                              ;D2 = SWITCH KEY TOGGLE
                              ;D3 = SWITCH OP ERROR
                              ;D4 = KEY UPDATE SLOW ONLY
                              ;D5 = SWITCH SHORT BEEP
                              ;D6 = UP/DOWN PAUSE
                              ;D7 = TEMP FOR KEY ROUTINES
FLAG6        EQU   FLAG5+1    ;FLAG #6
                              ;D0 = 10 BYTE PRINT INQUIRE
                              ;D1 = PRINT SHORT BEEP
                              ;D2 = PRINTER OFF LINE
                              ;D3 = SKIP RECALL ID MENU
                              ;D4 = NULL ID ENTRY AUTO-ID
                              ;D5 = S BUSS ENABLED
                              ;D6 = IN MAIN LOOP
                              ;D7 = PRINTER GET PR10RTN
FLAG7        EQU   FLAG6+1    ;FLAG #7
                              ;D0 = PRINTER PR9RTN AVAILABLE
                              ;D1 = PRINT RIBBON LEFT AVAILABLE
                              ;D2 = RECALL ID IN PROGRESS
                              ;D3 = NORMALIZE IN PROGRESS
                              ;D4 = INIT IN PROGRESS
                              ;D5 = PRINTER PR10RTN AVAILABLE
                              ;D6 = =>1 RECALL PERFORMED
                              ;D7 = SBUSS SENDING
FLAG8        EQU   FLAG7+1    ;FLAG #8
                              ;D0 = GET PRINT STATUS IN PROGRESS

;D1 = PRINT STATUS AVAILABLE
                              ;D2 = PRINT RECOVERY INIT IN
PROGRESS
                              ;D3 = PRINT RECOVERY INIT DONE
                              ;D4 = NO MENU CENTERING
                              ;D5 = SET VCR RECORD OVLY ON
```

```
                                        ;D6 = VCR RECORD OVLY IN PROGRESS
                                        ;D7 = SYSTEM UPDATE COMPLETE
DIGBUF          EQU     FLAG8+1         ;DISPLAY BUFFER(+8)

Working register bank 1, interrupt service.
    60H-6FH

IOPTRI          EQU     6AH             ;I/O PTR PAIR R10-R11
TPTR1I          EQU     6CH             ;PTR PAIR R12-R13
TPTR2I          EQU     6EH             ;PTR PAIR R14,R15

Working register bank 2, interrupt service.

SBUSSWB         EQU     70H             ;S BUSS WORKING BUFFER (5 BYTES)
SBBC            EQU     75H             ;S BUSS BIT COUNT
SBBYP           EQU     76H             ;S BUSS BYTE POINTER
DIV500          EQU     7AH             ;/500 RTC COUNTER RR10
SEC             EQU     7DH             ;SEC RTC COUNTER R13
MIN             EQU     7EH             ;MIN RTC COUNTER R14
HR              EQU     7FH             ;HR  RTC COUNTER  R15

General purpose Ram

NOENT           EQU     80H             ;# ENTRIES THIS MENU
ENTYPE          EQU     NOENT+1         ;DATA ENTRY TYPE
ENTNO           EQU     ENTYPE+1        ;ENTRY #
MINVAL          EQU     ENTNO+1         ;MINIMUM MENU VALUE
VALNO           EQU     MINVAL+1        ;ACTUAL MENU VALUE
MAXVAL          EQU     VALNO+1         ;MAXIMUM MENU VALUE
MNUMP           EQU     MAXVAL+1        ;-> EXT RAM ENTRY # AND VALUE #
MNUPTR          EQU     MNUMP+2         ;-> MENU BASE
NXBLK           EQU     MNUPTR+2        ;-> NEXT MENU BLOCK
SKIPPTR         EQU     NXBLK+2         ;-> VALUE SKIP LIST BASE
RMSWITCH        EQU     SKIPPTR+2       ;REMOTE SWITCH
RSLAST          EQU     RMSWITCH+1      ;LAST REMOTE SWITCH ENTRY
KTC             EQU     RSLAST+1        ;KEY TIMER TICK COUNT
KLTHC           EQU     KTC+1           ;KEY TIMER UPDATE TRANSITION COUNT

DB4COLOR        EQU     KLTHC+1         ;ROW BKGND COLOR USED BY DBLOCK4
MNUTO           EQU     DB4COLOR+1      ;MENU DISPLAY TIMEOUT COUNTER
KSWITCH         EQU     MNUTO+2         ;KEYBOARD SWITCH
THISBLK         EQU     KSWITCH+1       ;CURRENT MENU BLOCK POINTER
PIDCUR          EQU     THISBLK+2       ;PATIENT ID CURSOR POSITION
DTEMP           EQU     PIDCUR+1        ;TEMPORARY ID SECTION
DTRSAV          EQU     DTEMP+1         ;DTR STATUS

;0:0:0:OVLEN:CTEMP:WHBAL:UUEN:AIRIS
PRBYTE1         EQU     DTRSAV+1        ;PRINT RETURN BYTE #1
PRBYTE2         EQU     PRBYTE1+1       ;PRINT RETURN BYTE #2
CHPOS           EQU     PRBYTE2+1       ;CHARACTER POSTION DETECT
CHPOS1          EQU     CHPOS+1         ;CHARACTER POSTION DETECT #1
CHPOS2          EQU     CHPOS+2         ;CHARACTER POSTION DETECT #2
POPS            EQU     CHPOS2+1        ;PRINTER OPS STATE COUNTER
PRSENDB         EQU     POPS+1          ;PRINTER SEND BYTES
PRCOM           EQU     PRSENDB+2       ;PRINTER SEND STRING POINTER
```

```
PERR        EQU  PRCOM+2      ;PRINT ERROR CODE
PRDLY       EQU  PERR+1       ;RESPONSE DELAY COUNTER
UDPARM      EQU  PRDLY+1      ;UPDATE PARAMETER #
PFDTIMC     EQU  UDPARM+1     ;PRINT & FREEZE DELAY TIME COUNTER

PRSTATUS    EQU  PFDTIMC+2    ;PRINTER STATUS
PR9RTN      EQU  PRSTATUS+1   ;PRINTER 9 BYTE INQUIRE RETURN
PRIBLEFT    EQU  PR9RTN+1     ;PRINTER RIBBON LEFT
TERMTO      EQU  PRIBLEFT+2   ;TERMINATION COUNT FOR NORMALIZE
                                AND RECALL
PR10RTN     EQU  TERMTO+2     ;PRINTER 10 BYTE INQUIRE RETURN
DB2COLOR    EQU  PR10RTN+1    ;BKGND COLOR FOR DBLOCK2
DB7COLOR    EQU  DB2COLOR+1   ;ROW & CHARACTER COLOR FOR DBLOCK7

PRECDLYC    EQU  DB7COLOR+1   ;PRINT RECOVERY DELAY COUNTER
PINITREC    EQU  PRECDLYC+1   ;PRINT RECOVERY INIT DELAY COUNTER

CAPADR      EQU  PINITREC+2   ;PRINT CAPTIONS ADDRESS POINTER
TIMER0      EQU  CAPADR+2     ;TIMER #0
SBFRAME     EQU  TIMER0+1     ;S BUSS FRAME SYNC COUNTER
VOL20L      EQU  SBFRAME+1    ;20" SYSTEM VOLUME LAST SETTING
PPTIMC      EQU  VOL20L+1     ;PRINT 2ND PRESS DELAY COUNTER
WBALC       EQU  PPTIMC+1     ;WHITE BALANCE PULSE TIMER
DSRSAV      EQU  WBALC+1      ;DSR SAVE
                              ;D0 = /AUTOIRIS
                              ;D1 = /UURTS (0=SHAVER ON-LINE)
                              ;D2 = /SPARE1
                              ;D3 = /SPARE2
                              ;D4 = PDTR (1=PRINTER ON-LINE)
INITDSPY    EQU  DSRSAV+1     ;INIT DISPLAY STATE

FLAG10      EQU  INITDSPY+1   ;FLAG10
                              ;D0 = PFZ PRINT ERROR DISPLAY
                              ;D1 = EXT SIO LOGGED ON
                              ;D2 = DISABLE INTERNAL SWITCH OPS
                              ;D3 = EPROM CRC COMPLETE
                              ;D4 = ERAM TEST COMPLETE
                              ;D5 = IRAM TEST COMPLETE
                              ;D6 = FILE FULL DISPLAYED
                              ;D7 = 9" BACKGROUND ON

FLAG11      EQU  FLAG10+1     ;FLAG11
                              ;EXT SIO EASEDROP
                              ;D0 = UU IN
                              ;D1 = UU OUT
                              ;D2 = PRINTER IN
                              ;D3 = PRINTER OUT
                              ;D4 = WAND IN
                              ;D5 = KEYBOARD IN
                              ;D6 = STANDBY
                              ;D7 = CLS TOGGLE

FLAG12      EQU  FLAG11+1     ;FLAG12
                              ;D0 = LOGO DISPLAYED
                              ;D1 = SEND CAPTIONS IN PROGRESS
                              ;D2 = NON-DISPLAYABLE WAND ENTRY
```

```
EXBUFC      EQU  FLAG12+1      ;EXT SIO BUFFER RVCD COUNT
EXBUFAL     EQU  EXBUFC+1      ;EXT SIO BUFFER ADDRESS LO
EXBUFAH     EQU  EXBUFAL+1     ;EXT SIO BUFFER CODE-ADDRESS HI
EXBUFDAT    EQU  EXBUFAH+1     ;EXT SIO BUFFER DATA
EPCRCH      EQU  EXBUFDAT+1    ;EPROM CRC HI
EPCRCL      EQU  EPCRCH+1      ;EPROM CRC LO
EPCRCAH     EQU  EPCRCL+1      ;EPROM CRC ADDRESS HI
EPCRCAL     EQU  EPCRCAH+1     ;EPROM CRC ADDRESS LO
FPTRTEMP    EQU  EPCRCAL+1     ;TEMP FILE PTR
UUSTATE     EQU  FPTRTEMP+2    ;UU PARM MACHINE STATE
UUPCNT      EQU  UUSTATE+1     ;UU RECEIVED CHARACTER COUNT
NX          EQU  UUPCNT+1      ;NEXT
RAMTOP      EQU  0CFH          ;TOP OF RAM
```

Stack
Note: D0-D7 required by emulator.

```
STK_TOP     EQU  0EFH          ;TOP OF STACK
```

Program constants

```
WRB0        EQU  10H           ;R0-R15 WORKING REGISTER BANK 0
WRB1        EQU  60H           ;R0-R15 WORKING REGISTER BANK 1
WRB2        EQU  70H           ;R0-R15 WORKING REGISTER BANK 2
KDLY1       EQU  100           ;UP/DOWN KEY PAUSE DELAY
(*LOOPTIMES)
DLY1S       EQU  60            ;1S DELAY
DLY2S       EQU  120           ;2S DELAY
DLY3S       EQU  180           ;3S DELAY
DLY4S       EQU  240           ;4S DELAY
DLY5S       EQU  300           ;5S DELAY
DLY6S       EQU  360           ;6S DELAY
DLY8S       EQU  480           ;8S DELAY
ELTCNTP     EQU  60            ;ELAPSED TIME DISPLAY UPDATE
(*1/60)
ETCOLOR     EQU  8             ;ELAPSED TIME CHAR COLOR
ETROW       EQU  0             ;ELAPSED TIME ROW POSITION
ETCOL       EQU  0             ;ELAPSED TIME COL POSITION
ETMCOLOR    EQU  6             ;ELAPSED TIME MENU CHAR COLOR
ETMROW      EQU  6             ;ELAPSED TIME MENU ROW POSITION
ETMCOL      EQU  6             ;ELAPSED TIME MENU COL POSITION
PFMDLYT     EQU  30            ;MONITOR UNFREEZE DELAY
POLY        EQU  8005H         ;CRC POLYNOMINAL
```

External Memory Mapping

```
VIDSTORE    EQU  EMEM+300H     ;VIDEO MEMORY STORE
MENUNO      EQU  VIDSTORE+172  ;BASE OF MENU AND VALUE NUMBERS
PATID       EQU  MENUNO+180    ;BASE OF PATIENT ID BUFFER
PATFILE     EQU  PATID+20      ;BASE OF PATIENT DATA FILE
MENUSAV     EQU  PATFILE+122   ;MACHINE STATE SAVE BUFFER
AUTOID      EQU  MENUSAV+220   ;BASE OF AUTO-SET ID BUFFER
AUTOFILE    EQU  AUTOID+20     ;BASE OF AUTO-SET DATA FILE
MENLAST     EQU  AUTOFILE+222  ;LAST SET MACHINE PARAMETERS
SYSHRA      EQU  MENLAST+20    ;SYSTEM HRS TOTAL SEC:MIN:HR:HR
```

```
LMPHRA    EQU   SYSHRA+4           ;LAMP HRS TOTAL SEC:MIN:HR:HR
LRESETA   EQU   LMPHRA+4           ;LAMP RESET SWITCH MEMORY
RIBBONA   EQU   LRESETA+1          ;RIBBON LEFT
PRERRA    EQU   RIBBONA+2          ;PRINT ERROR #
CAPTION1  EQU   PRERRA+2           ;PRINTER CAPTIONS LINE 1 (80 BYTES)
CAPTION2  EQU   CAPTION1+80        ;PRINTER CAPTIONS LINE 2 (80 BYTES)
WANDBUF   EQU   CAPTION2+80        ;WAND INPUT BUFFER (21 BYTES)
UUPARM    EQU   WANDBUF+21         ;UU PARM LIST
NEXR      EQU   UUPARM+5           ;NEXT

Program Constants

BK9       EQU   1                  ;9" CAMERA BACKGROUND
INITDLY   EQU   255                ;INIT DELAY LOOP TIME (*LOOPTIMES)
CBTEST    EQU   255                ;COLOR BAR TEST TIME (*LOOPTIMES)
LGTEST    EQU   255                ;LOGO TEST TIME (*LOOPTIMES)
BEEPSH    EQU   7                  ;SHORT BEEP DURATION (*LOOPTIMES)
BEEPLG    EQU   30                 ;LONG BEEP DURATION (*LOOPTIMES)
BEEPOP    EQU   7                  ;OP ERROR BEEP DURATION (*LOOPTIMES/2)
BEEPOFF   EQU   30                 ;BEEP OFF DURATION (*LOOPTIMES)
MINVOL    EQU   70                 ;MINIMUM VOLUME
MNUCC     EQU   2                  ;MENU CHARACTER COLOR
MNUBKG    EQU   8                  ;MENU BACKGROUND
MNUHL     EQU   4                  ;MENU HIGHLIGHT
MNUCC2    EQU   6                  ;MENU (DBLOCK2) CHARACTER COLOR
MNUBKG2   EQU   8                  ;MENU (DBLOCK2) BACKGROUND
MNUHL2    EQU   0                  ;MENU (DBLOCK2) HIGHLIGHT
PMNUCC    EQU   2                  ;PATIENT DATA MENU CHARACTER COLOR
PMNUBKG   EQU   8                  ;PATIENT MENU BACKGROUND
PMNUHL    EQU   4                  ;PATIENT MENU HIGHLIGHT
OVLYCC    EQU   6                  ;OVERLAY MESSAGE CHARACTER COLOR
OVLYCC2   EQU   6                  ;OVLY MESSAGE WITH ROW BACKGROUND CHAR COLOR
OVLYHL    EQU   4                  ;OVLY MESSAGE ROW BKGND COLOR
MOVLYCC   EQU   6                  ;MULTIPLE OVERLAY CHARACTER COLOR
MOVLYCC2  EQU   2                  ;MULTIPLE OVERLAY WITH ROW BACKGROUND
                                    CHARCOLOR
MOVLYHL   EQU   4                  ;MULTIPLE OVERLAY ROW BKGND COLOR
DMESSC    EQU   6                  ;DMESS CHARACTER COLOR
PIDCC     EQU   6                  ;PATIENT ID MENU CHARACTER COLOR
STATCLR   EQU   6                  ;STATUS MENU CHARACTER COLOR
ERRCLR    EQU   5                  ;ERROR AND LOGO CHARACTER COLOR
KTIMELS   EQU   15                 ;KEY TIMER UPDATE SLOW (*LOOPTIMES)
KTIMEHS   EQU   2                  ;KEY TIMER UPDATE FAST (*LOOPTIMES)
KLOTOHI   EQU   4                  ;KEY TIMER LO-HI TRANSITION POINT
PGSTATD   EQU   4                  ;PRINTER GET STATUS DELAY (*LOOPTIMES)
PGSTATD2  EQU   4                  ;PRINTER GET STATUS (SEND CAPTIONS)
PEXECD    EQU   19                 ;PRINTER GET EXECUTE RESPONSE DELAY
(*LOOPTIMES)
PEXECD2   EQU   60                 ;PRINTER GET EXECUTE (SEND CAPTIONS)
PFDTIML   EQU   <240               ;PRINT-FREEZE DELAY (*LOOPTIMES)
PFDTIMH   EQU   >240
PRTIML    EQU   <4400              ;PRINT DELAY (*LOOPTIMES)
PRTIMH    EQU   >4400
PRECDLY   EQU   120                ;PRINT ERROR RECOVERY DELAY
PINITDLY  EQU   600                ;PRINT ERROR INIT DELAY
PPTIM     EQU   45                 ;PRINT 2ND PRESS DELAY INIT
```

```
WBALCT    EQU   30          ;WHITE BALANCE PULSE TIME
SYNFAIL   EQU   35000       ;VSYNC LOOP FAIL TIME
SHUTDLY   EQU   80          ;SHUTTER ON DELAY (*LOOPTIMES)
GRTIME    EQU   200         ;GET RIBBON LEFT TIME (*LOOPTIMES)
RIBW      EQU   6           ;RIBBON LOW WARNING COUNT
PWPINIT   EQU   8EH         ;D0 = /REMCS
                            ;D1 = /REMCK
                            ;D2 = /SYNCSEL
                            ;D3 = /AGAIN
                            ;D4 = SELMONB
                            ;D5 = BEEPEN
                            ;D6 = /BEEPEN
                            ;D7 = /KINHB

Terminal error codes

VSTO_F    EQU   0           ;NO VSYNC FAIL
GIO_F     EQU   1           ;GUARDED I/O OR MEMORY
EPCRC_F   EQU   2           ;EPROM CRC FAIL
ERAM_F    EQU   3           ;EXTERNAL RAM FAIL
IRAM_F    EQU   4           ;INTERNAL RAM FAIL

Special registers

P01_MODE  EQU   96H         ;PORT 0-1 MODE
                            ;MPX I/O, NORMAL TIMING, INTERNAL STACK

P02_MODE  EQU   0FFH        ;PORT 2 MODE = INPUT
P03_MODE  EQU   00H         ;PORT 3 MODE
                            ;P30=P31=P33 = INPUT
                            ;P34=P35=P36 = OUTPUT
IPR_MODE  EQU   1EH         ;INTERRUPT PRIORITY
                            ;GROUP A: IRQ5>IRQ3
                            ;GROUP B: IRQ0>IRQ2
                            ;GROUP C: IRQ4>IRQ1
                            ;B > A > C
IMR_MODE  EQU   80H         ;INTERRUPT MASK
                            ;ENABLE MASTER & EMULATOR ONLY
PORT01    EQU   248         ;PORT 0-1 MODE
PORT02    EQU   246         ;PORT 2 MODE
PORT03    EQU   247         ;PORT 3 MODE
STK_LSB   EQU   255         ;STACK PTR LSB
STK_MSB   EQU   254         ;STACK PTR MSB
I_IMSK    EQU   251         ;INTERRUPT MASK REGISTER
I_IPR     EQU   249         ;INTERRUPT PRIORITY REGISTER
T0_PRE    EQU   245         ;TIMER #0 PRESCALE BY REGISTER
T0_DIV    EQU   244         ;TIMER #0 DIVIDE BY REGISTER
T_MODE    EQU   241         ;TIMER MODE REGISTER
T1_PRE    EQU   243         ;TIMER #1 PRESCALE BY REGISTER
T1_DIV    EQU   242         ;TIMER #1 DIVIDE BY REGISTER
P_2       EQU   2           ;PORT 2
P_3       EQU   3           ;PORT 3
```

External memory addresses.
Note: any SIO input-output buffer group may not cross an msb address boundry.

```
WANDIBOT    EQU   4000H           ;SIO WAND INPUT BUFFER BOTTOM
WANDITOP    EQU   403FH           ;SIO WAND INPUT BUFFER TOP
WANDOBOT    EQU   4040H           ;SIO WAND OUTPUT BUFFER BOTTOM
WANDOTOP    EQU   407FH           ;SIO WAND OUTPUT BUFFER TOP
SBUSOBOT    EQU   4240H           ;S BUSS OUTPUT BUFFER BOTTOM

LAMPHR      EQU   LMPHRA+2        ;-> ELAPSED TIME LAMP HOURS
SYSHR       EQU   SYSHRA+2        ;-> ELAPSED TIME SYSTEM HOURS
            END
```

3. TABLE SECTION

The following is the Table Section of the program for the imaging unit 12.

'TABLES'

```
;     Remote Unit switch code table.
;
RSWTBLA     DB    0,0,0,0,0,0,0,0          ;0-7
            DB    0,7,8,10,0,2,16,5        ;8-15
            DB    0,6,9,11,12,14,1,3       ;16-23
            DB    0,26,27,13,0,15,17,4     ;24-31
            DB    32,0                     ;CROSSKEY,DISCONNECT
;
;     Switch command table.
;
SCMND       DW    SW0             ;NO KEYS
            DW    SW1             ;AUTO IRIS (R+FP)
            DW    SW2             ;PRINT (R+FP)
            DW    SW3             ;MENU ENTER (R+FP)
            DW    SW4             ;MENU DOWN (R+FP)
            DW    SW5             ;MENU UP (R+FP)
            DW    SWSR            ;PUMP START/STOP (R)
            DW    SWSR            ;PUMP FLOW UP (R)
            DW    SWSR            ;PUMP FLOW DOWN (R)
            DW    SWSR            ;LAVAGE (R)
            DW    SWSR            ;SHAVER START/STOP (R)
            DW    SWSR            ;SHAVER RPM UP (R)
            DW    SWSR            ;SHAVER RPM DOWN (R)
            DW    SWSR            ;SHAVER MODE (R)
            DW    SW14            ;VCR (R)
            DW    SW15            ;TIMER (R)
            DW    SW16            ;ILLUM UP (R)
            DW    SW17            ;ILLUM DOWN (R)
            DW    SW0             ;SPARE (18)
            DW    SW19            ;WAND INPUT READY (W)
            DW    SW20            ;KEYBOARD BK SPACE (K)
            DW    SW21            ;KEYBOARD CR (K)
            DW    SW22            ;KEYBOARD UP (K)
            DW    SW23            ;KEYBOARD DOWN (K)
            DW    SW24            ;KEYBOARD DEL (K)
            DW    SW0             ;KEYBOARD END (K)
            DW    SWSR            ;PUMP PRESSURE UP (R)
```

```
          DW    SWSR           ;PUMP PRESSURE DN (R)
          DW    SW0            ;SPARE (28)
          DW    SW0            ;SPARE (29)
          DW    SW0            ;SPARE (30)
          DW    SW0            ;SPARE (31)
          DW    SWOPE          ;CROSSKEY (32)
          DW    SW33           ;DISCONNECT (33)
          DW    SWSR           ;SHAVER UPLOAD (34)
          DW    SW35           ;SHAVER DOWNLOAD (35)
;
;     External SIO Command Table.
;
EXSIOCM   DW    EXSC0          ;RAM READ
          DW    EXSC1          ;RAM WRITE
          DW    EXSC2          ;EXT RAM READ
          DW    EXSC3          ;EXT RAM WRITE
          DW    EXSC4          ;EPROM READ (4K)
          DW    EXSC5          ;DISABLE SWITCHOPS
          DW    EXSC6          ;ENABLE SWITCHOPS
          DW    EXSC7          ;LOG-ON
          DW    EXSC8          ;STANDBY
          DW    EXSC9          ;CALL
          DW    EXSC10         ;EASEDROP UU IN
          DW    EXSC11         ;EASEDROP UU OUT
          DW    EXSC12         ;EASEDROP PRINTER IN
          DW    EXSC13         ;EASEDROP PRINTER OUT
          DW    EXSC14         ;EASEDROP WAND IN
          DW    EXSC15         ;EASEDROP KEYBOARD IN
;
;     S Buss command table.
;     Note: EOF = 0FFH
;
SBCMND    DB    05H,9DH,0FFH   ;VCR RECORD
          DB    05H,98H,0FFH   ;VCR STOP
          DB    05H,9BH,0FFH   ;VCR REWIND
          DB    05H,9AH,0FFH   ;VCR PLAY
          DB    05H,98H,0FFH   ;VCR STOP
          DB    05H,9CH,0FFH   ;VCR FF
          DB    05H,0AEH,0FFH  ;VCR POWER-ON
          DB    00H,0AEH,0FFH  ;TV POWER-ON
          DB    00H,92H,0FFH   ;TV VOLUME UP
          DB    00H,93H,0FFH   ;TV VOLUME DOWN
          DB    00H,0C5H,0FFH  ;TV SELECT CAMERA LINE B
          DB    00H,0C0H,0FFH  ;TV SELECT VCR LINE A
          DB    00H,0AFH,0FFH  ;TV POWER-OFF
SBCSPARE  DB    00H,00H,0FFH   ;TEST ONLY
          DB    05H,0D8H,0FFH  ;VCR SPEED TOGGLE
          DB    05H,0DAH,0FFH  ;VCR DATA SCREEN TOGGLE
          DB    05H,0AEH,0FFH  ;VCR POWER ON
          DB    05H,0AFH,0FFH  ;VCR POWER OFF
          DB    05H,0AAH,0FH   ;VCR TOGGLE ANT VTR/TV
          DB    05H,0CFH,0FFH  ;VCR TOGGLE LINE INPUT
          DB    05H,0CDH,0FFH  ;VCR MENU SELECT
          DB    05H,0C3H,0FFH  ;VCR MENU UP
          DB    05H,0C2H,0FFH  ;VCR MENU DN
          DB    05H,0D1H,0FFH  ;VCR MENU EXECUTE
```

```
             DB     05H,0E2H,0FFH         ;VCR MENU LEFT
             DB     05H,0E1H,0FFH         ;VCR MENU RIGHT
;
;       Printer ops command table.
;
PRCOMTBL     DW     PROPS0                ;IDLE
             DW     PROPS1                ;SEND GET STATUS
             DW     PROPS2                ;SEND EXECUTE
             DW     PROPS3                ;CK RESPONSE
             DW     PROPS8                ;SEND GET STATUS (SEND CAPTIONS)
             DW     PROPS9                ;SEND PREAMBLE
             DW     PROPS10               ;SEND CAPTIONS
             DW     PROPS11               ;SEND POSTAMBLE
;
;       Display type address list.
;
DTYPECM      DW     DBLOCK1               ;TYPE #0
             DW     DBLOCK1               ;TYPE #1
             DW     DBLOCK2               ;TYPE #2
             DW     DBLOCK3               ;TYPE #3
             DW     DBLOCK2               ;TYPE #4
             DW     DBLOCK6               ;TYPE #5
             DW     DBLOCK3               ;TYPE #6
             DW     DBLOCK4               ;TYPE #7
             DW     DBLOCK7               ;TYPE #8
             DW     DBLOCK5               ;TYPE #9
             DW     DBLOCK6               ;TYPE #10
             DW     DBLOCK7               ;TYPE #11
;
;       Normalized default parameters table.
;
NORMTBL      DB     2,1                   ;PRINTER FORMAT FULL PAGE (+0)
             DB     2,0                   ;AUTO IRIS
             DB     2,0                   ;ID OVLY
             DB     2,0                   ;TIMER OVLY
             DB     2,1                   ;VCR/20" POWER ON
             DB     2,1                   ;PRINTER CLEAR MEMORY
             DB     2,0                   ;AUTO GAIN
             DB     0,0                   ;SPARE
;
             DB     2,1                   ;PRINTER FONT ON/OFF (+1)
             DB     2,1                   ;PRINTER VIDEO MODE (R-B-G) SELECT DB     2,1                   ;PRINTER CLEAR ID CAPTIONS
             DB     1,0                   ;PRINTER FREEZE
             DB     1,0                   ;PRINTER FONT WITH CAPTIONS
             DB     2,1                   ;PRINTER UNFREEZE
             DB     1,0                   ;PRINTER GET RIBBON LEFT
             DB     0,0                   ;9" VIDEO ON/OFF
;
;
             DB     2,0                   ;IRIS LEVEL (+2)
             DB     0,0                   ;MOD 2 PARM BYTE #1 (+3)
             DB     2,1                   ;PRINTER SHARPNESS LEVEL (+4)
             DB     1,0                   ;PRINTER FORMAT (+5)
             DB     2,0                   ;MONITOR INPUT SELECT (MENU) (+6)
```

```
          DB    0,0             ;MOD 2 PARM BYTE #2 (+8)
          DB    4,0             ;BEEP VOLUME (+9)
          DB    4,0             ;PRINTER RED LEVEL (+10)
          DB    4,0             ;PRINTER BLUE LEVEL (+11)
          DB    4,0             ;PRINTER GREEN LEVEL (+12)
          DB    4,0             ;PRINTER LIGHT LEVEL (+13)
          DB    4,0             ;PRINTER DARK LEVEL (+14)
          DB    1,0             ;PRINTER COLOR ADJUST MENU SELECT (+15)

DB    2,0             ;PRINTER IMAGE POSITION (+16)
          DB    2,1             ;PRINTER SEND ID CAPTION (+17)
          DB    2,1             ;VCR CONTROL (+18)
          DB    2,0             ;LAST SET (SPARE) (+19)
;
;    Print Recovery Initialization table.
;
PIRTBL    DB    2,1             ;PRINTER FORMAT FULL PAGE (+0)
          DB    0,0             ;AUTO IRIS
          DB    0,0             ;ID OVERLAY
          DB    0,0             ;TIMER OVERLAY
          DB    0,0             ;VCR/20" POWER ON
          DB    0,0             ;PRINTER CLEAR MEMORY
          DB    0,0             ;AUTO GAIN
          DB    0,0             ;SPARE
;
          DB    2,0             ;PRINTER FONT ON/OFF (+1)
          DB    2,1             ;PRINTER VIDEO SELECT R-B-G
          DB    0,0             ;PRINTER CLEAR ID CAPTIONS
          DB    1,0             ;PRINTER STORE/FREEZE
          DB    1,0             ;PRINTER PRINT WITH CAPTIONS
          DB    2,1             ;PRINTER UNFREEZE
          DB    2,1             ;PRINTER GET RIBBON LEFT
          DB    0,0             ;9" VIDEO ON/OFF
;
          DB    0,0             ;IRIS LEVEL (+2)
          DB    0,0             ;MOD 2 PARM BYTE #1 (+3)
          DB    4,0             ;PRINTER SHARPNESS LEVEL (+4)
          DB    4,0             ;PRINTER FORMAT SELECT (+5)
          DB    0,0             ;MONITOR INPUT SELECT (MENU) (+6)
          DB    0,0             ;MONITOR VOLUME (+7)
          DB    0,0             ;MOD 2 PARM BYTE #2 (+8)
          DB    0,0             ;BEEP VOLUME (+9)
          DB    4,0             ;PRINTER RED LEVEL (+10)
          DB    4,0             ;PRINTER BLUE LEVEL (+11)
          DB    4,0             ;PRINTER GREEN LEVEL (+12)
          DB    4,0             ;PRINTER LIGHT LEVEL (+13)
          DB    4,0             ;PRINTER DARK LEVEL (+14)
          DB    1,0             ;COLOR ADJUST MENU SELECT (+15)
          DB    4,0             ;PRINTER IMAGE POSITION (+16)
          DB    2,0             ;PRINTER SEND ID CAPTION (+17)
          DB    0,0             ;VCR CONTROL (+18)
          DB    0,0             ;LAST SET (SPARE) (+19)
;
;    SIO Initialization, ports #1-#5.
;
;    S2:S1:EP1:EP0:L2:L1:1:0
```

```
;
;       S2:S1            Stop bits   1=1 bit, 2=1.5 bits, 3=2 bits
;       EP1:EP0          Parity      0=disable, 1=odd, 3=even
;       L2:L1            Data Length 0=5 bits, 1=6 bits, 2=7 bits, 3=8
bits
;
SIOX    DB      4EH                 ;WAND, NO PARITY, 1SB, 8DB, 16X CLOCK
        DB      4EH                 ;U-U, NO PARITY, 1SB, 8DB, 16X CLOCK
        DB      4EH                 ;EXT, NO PARITY, 1SB, 8DB, 16X CLOCK
        DB      4EH                 ;PRINTER, NO PARITY, 1SB, 8DB, 16X
CLOCK
        DB      4EH                 ;KEYBOARD, NO PARITY, 1SB, 8DB, 16X
CLOCK
;
;       SIO baud rates created by CTC #1 and CTC #2.
;
SIOBDR  DB      27                  ;WAND, 9600 BAUD
        DB      213                 ;U-U,  1200 BAUD
        DB      27                  ;EXT, 9600 BAUD
        DB      53                  ;PRINTER, 4800 BAUD
        DB      213                 ;KEYBOARD, 1200 BAUD
        DB      27                  ;SPARE, 9600 BAUD
;
;       SIO Command write at initialization.
;       /RTS = 1, all ports.
;
SIOCTBL DB      0                   ;WAND, AIRIS = 1
        DB      0                   ;U-U, /UUEN =1
        DB      0                   ;EXT, /WHBAL = 1
        DB      0                   ;PRINTER, /CTEMPEXT = 1
        DB      0                   ;KEYBD, /OVLENA = 1
;
;       Message end of file character.
;
EOFCHAR         DB      '$'
;
;       Printer command string table.
;
;       First byte is the number of bytes to be sent.
;       Second byte is the position of the send string of value #1.
;       Third byte is the position of the send string of value #2.
;       A zero value position indicates the value is a literal.
;       The values are retrieved from DIGBUF and DIGBUF+1 respectively.
;       The value positions are occupied by a '*' in the string.
;
PRGSTAT         DB      9,0,0,02H,00H,03H,0FFH,0FCH     ;GET STATUS
                DB      01H,04H,47H,03H
;
PRFM    DB      9,0,7,02H,00H,03H,0FFH,0FCH     ;FONT CTRL ON/OFF
        DB      01H,8CH,'*',03H
;
PRADJC          DB      9,6,7,02H,00H,03H,0FFH,0FCH     ;ADJUST COLOR
                DB      01H,'*','*',03H
;
;
```

```
PRSFCM          DB      9,0,7,02H,00H,03H,0FFH,0FCH     ;PRINTER
STORE-FREEZE/CLEAR
                DB      01H,83H,'*',03H
PRNT            DB      9,0,0,02H,00H,03H,0FFH,0FCH     ;PRINTER PRINT WITH
CAPTIONS
                DB      01H,80H,8EH,03H
PRSLV           DB      9,0,7,02H,00H,03H,0FFH,0FCH     ;PRINTER SELECT
VIDEO
                DB      01H,8BH,'*',03H
PRFORM          DB      9,0,7,02H,00H,03H,0FFH,0FCH     ;PRINTER SELECT
FORMAT
                DB      01H,84H,'*',03H
PRUNFZ          DB      9,0,7,02H,00H,03H,0FFH,0FCH     ;PRINTER SELECT
MONITOR/MEMORY
                DB      01H,89H,'*',03H
PRSHRP          DB      9,0,7,02H,00H,03H,0FFH,0FCH     ;PRINTER SELECT
SHARPNESS
                DB      01H,90H,'*',03H
PRIS            DB      9,6,7,02H,00H,03H,0FFH,0FCH     ;PRINTER SELECT IMAGE
                DB      01H,'*','*',03H
PRGRL           DB      9,0,0,02H,00H,03H,0FFH,0FCH     ;PRINTER RIBBON
LEFT INQUIRE
                DB      01H,04H,0ADH,03H
PRCCD           DB      9,0,0,02H,00H,03H,0FFH,0FCH     ;PRINTER CLEAR
CAPTIONS
                DB      01H,8EH,19H,03H
PRCSD           DB      7,0,0,02H,00H,0A2H,0FFH,5DH     ;PRINTER SEND
CAPTIONS (160)
                DB      01H,43H                          ;NOTE TRAILER
REQUIRED
;
;
;       Binary to BCD conversion table.
;
BCDTBL  DB      00,00,01
        DB      00,00,02
        DB      00,00,04
        DB      00,00,08
        DB      00,00,16H
        DB      00,00,32H
        DB      00,00,64H
        DB      00,01,28H
        DB      00,02,56H
        DB      00,05,12H
        DB      00,10H,24H
        DB      00,20H,48H
        DB      00,40H,96H
        DB      00,81H,92H
        DB      01,63H,84H
        DB      03,27H,68H
;
;       Display initialization color bar test
;
CBINTBL DB      0BH             ;POS SYNC:PXSZ=0:RES=HI:RTB=3
        DB      10H             ;VERT POSITION
        DB      7               ;HORIZ POSITION
```

```
            DB      81H             ;DSPY ON:BKGND OFF:FRNG OFF:BKG BLUE
            DB      10H             ;ROW SPACING
            DB      0               ;FADE POSITION
            DB      0               ;BAR CTRL
            DB      0               ;BAR POSITION
;
;       Display initialization normal mode
;
DINTBL      DB      0BH             ;POS SYNC:PXSZ=0:RES=HI:RTB=3
            DB      6               ;VERT POSIITON
            DB      8               ;HORIZ POSITION
            DB      81H             ;DSPY ON:BKGND OFF:FRNG OFF:BKG BLUE
            DB      27              ;ROW SPACING
            DB      0               ;FADE POSITION
            DB      0               ;BAR CTRL
            DB      0               ;BAR POSITION
;
;       Messages
;
;
BLANKM          DB  '                    $'     ;BLANK
BLANK4          DB  '    $'                     ;4 SP
;
DIGITM          DB  '!!!!$'                     ;4 CHARACTER DIGIT
;
VCRRECM         DB  'REC$'                      ;VCR RECORD
VCRPLAYM        DB  'PLAY$'                     ;VCR PLAY
;
WARMUP          DB  '     WARM UP     $'        ;WARM UP
SLFTST          DB  '   SELF TEST V2.4 $'       ;SELF TEST
STUP            DB  '      SET UP      $'       ;SET UP
SINITM          DB  'SYSTEM INITIALIZED $'      ;SYS INIT
TERR            DB  'FATAL ERROR !$'            ;TERMINAL ERROR
FFULLM          DB  'FULL-SELECT THEN DEL$'     ;ID FILE FULL
CKRIB           DB  'WARNING RIBBON LOW $'      ;RIBBON LOW
CKLMP           DB  'WARNING CHANGE LAMP$'      ;LAMP HRS HI
;
;       Menu blocks.
;       First entry is the number of entries this menu.
;       Next entry is the type which governs display and input.
;       Next entry is -> base of this menu list (0 = none).
;       Next entry is -> base of the next block list (0 = none).
;       Next entry is -> base of the skip value list (optional).
;
;       Block menus.
;
BLK0    DB      10                              ;TOP LEVEL, # ENTRIES
        DB      0,0,0,0,0,1,1,1,0,0             ;TYPE CODE
        DW      MENUN0                          ;-> MENU # (EXT RAM)
        DB      0,0                             ;MIN-MAX VALUE
        DW      MENU0                           ;-> MENU
        DW      DISTATUS,IDSEL,IDSEL            ;NEXT BLOCK ->
        DW      EXNORM,EXVCRLO,BLK04,BLK05
        DW      BLK06,CBARON,EXRTSND
;
BLK00B  DB      1                               ;PATIENT ID LEVEL 1
```

```
            DB    6                       ;TYPE CODE
            DW    MENUNO+2                ;-> MENU # (EXT RAM)
            DB    0,0                     ;MIN-MAX VALUE
            DW    0                       ;MENU ->
            DW    PIDCAP                  ;NEXT BLOCK ->
;
BLK00C      DB    1                       ;AUTO SET-UP LEVEL 1
            DB    6                       ;TYPE CODE
            DW    MENUNO+40               ;-> MENU # (EXT RAM)
            DB    0,0                     ;MIN-MAX VALUE
            DW    0                       ;MENU ->
            DW    IDSKMNU                 ;NEXT BLOCK ->
;
BLK0A       DB    1                       ;VOLUME ADJUST LEVEL 1
            DB    5                       ;TYPE CODE
            DW    MENUNO+26               ;-> MENU # (EXT RAM)
            DB    0,0                     ;MIN-MAX VALUE
            DW    MENU0A                  ;MENU ->
            DW    EXRTSND                 ;NEXT BLOCK ->
;
BLK03       DB    6                       ;VCR LEVEL 1
            DB    0,0,0,0,0,0             ;TYPE CODE
            DW    MENUNO+4                ;-> MENU # (EXT RAM)
            DB    0,0                     ;MIN-MAX VALUE
            DW    MENU03                  ;MENU ->
            DW    EXVCROP,EXVCROP,EXVCROP ;NEXT BLOCK ->
            DW    EXVCROP,EXVCROP,EXVCROP
;
BLK04       DB    2                       ;AUTO IRIS LEVEL 1
            DB    0,1                     ;TYPE CODE
            DW    MENUNO+6                ;-> MENU # (EXT RAM)
            DB    0,0                     ;MIN-MAX VALUE
            DW    MENU04                  ;MENU ->
            DW    EXRTS,BLK041            ;NEXT BLOCK ->
;
BLK04T      DB    2                       ;AUTO IRIS DISPLAY ONLY
            DB    7,7                     ;TYPE CODE
            DW    MENUNO+6                ;-> MENU # (EXT RAM)
            DB    0,0                     ;MIN-MAX VALUE
            DW    MENU04                  ;MENU ->
            DW    0,0                     ;NEXT BLOCK ->
;
BLK05       DB    3                       ;TIMER LEVEL 1
            DB    0,0,0                   ;TYPE CODE
            DW    MENUNO+8                ;-> MENU # (EXT RAM)
            DB    0,0                     ;MIN-MAX VALUE
            DW    MENU05                  ;MENU ->
            DW    EXTSET1,EXTSET2,EXTSET3 ;NEXT BLOCK ->
;
BLK06       DB    4                       ;SYSTEM SET-UP LEVEL 1
            DB    0,1,1,1                 ;TYPE CODE
            DW    MENUNO+10               ;-> MENU # (EXT RAM)
            DB    0,0                     ;MIN-MAX VALUE
            DW    MENU06                  ;MENU ->
            DW    EXPRVPR,BLK062          ;NEXT BLOCK ->
            DW    BLK064,BLK063
```

```
            DB      0,0                     ;MONITOR VOLUME (+7)
            DB      0,0                     ;MOD 2 PARM BYTE #2 (+8) (+8)
            DB      2,0                     ;BEEP VOLUME (+9)
            DB      2,8                     ;PRINTER RED LEVEL (+10)
            DB      2,8                     ;PRINTER BLUE LEVEL (+11)
            DB      2,8                     ;PRINTER GREEN LEVEL (+12)
            DB      2,8                     ;PRINTER LIGHT LEVEL (+13)
            DB      2,8                     ;PRINTER DARK LEVEL (+14)
            DB      1,0                     ;PRINTER COLOR ADJUST MENU SELECT
(+15)
            DB      1,0                     ;PRINTER IMAGE POSITION (+16)
            DB      2,1                     ;PRINTER SEND ID CAPTION (+17)
            DB      0,0                     ;VCR CONTROL (+18)
            DB      2,0                     ;LAST SET (SPARE) (+19)
;
;       Post Recall ID set table.  Values set following download of
;       PID file MENSAV into MENUNO.
;
RECTBL      DB      2,1                     ;PRINTER FORMAT FULL PAGE (+0)
            DB      0,0                     ;AUTO IRIS
            DB      0,0                     ;ID OVLY
            DB      0,0                     ;TIMER OVLY
            DB      2,1                     ;VCR/20" POWER ON
            DB      2,1                     ;PRINTER CLEAR MEMORY
            DB      0,0                     ;AUTO GAIN
            DB      0,0                     ;SPARE
;
            DB      2,1                     ;PRINTER FONT ON/OFF (+1)
            DB      1,1                     ;PRINTER VIDEO SELECT R-B-G
            DB      2,1                     ;PRINTER CLEAR ID CAPTIONS
            DB      1,0                     ;PRINTER FREEZE
            DB      1,0                     ;PRINTER PRINT
            DB      2,1                     ;PRINTER UNFREEZE
            DB      1,0                     ;PRINTER GET RIBBON LEFT
            DB      0,0                     ;9" VIDEO ON/OFF
;
            DB      0,0                     ;IRIS LEVEL (+2)
            DB      0,0                     ;MOD 2 PARM BYTE #1 (+3)
            DB      0,0                     ;PRINTER SHARPNESS (+4)
            DB      0,0                     ;PRINTER FORMAT SELECT (+5)
            DB      0,0                     ;MONITOR INPUT SELECT (MENU) (+6)
            DB      0,0                     ;MONITOR VOLUME (+7)
            DB      0,0                     ;MOD 2 PARM BYTE #2 (+8)
            DB      0,0                     ;BEEP VOLUME (+9)
            DB      0,0                     ;PRINTER RED LEVEL (+10)
            DB      0,0                     ;PRINTER BLUE LEVEL (+11)
            DB      0,0                     ;PRINTER GREEN LEVEL (+12)
            DB      0,0                     ;PRINTER LIGHT LEVEL (+13)
            DB      0,0                     ;PRINTER DARK LEVEL (+14)
            DB      1,0                     ;COLOR ADJUST MENU SELECT (+15)
            DB      2,0                     ;PRINTER IMAGE POSITION (+16)
            DB      2,1                     ;PRINTER SEND ID CAPTION (+17)
            DB      2,1                     ;VCR CONTROL (+18)
            DB      2,0                     ;LAST SET (SPARE) (+19)
;
;       The first 16 values are bit (0/1) entry number locations,
```

```
;       the next 18 values are value number locations.
;       A zero loads a zero entry # or value into the MENUSAV file
;       and performs NOP during retrieval.
;
PARMTBL     DW      MENUNO+23           ;-> PRINTER FORMAT FULL PAGE (+0)
            DW      MENUNO+6            ;-> AUTO IRIS
            DW      MENUNO+18           ;-> ID OVLY
            DW      MENUNO+16           ;-> TIMER OVLY
            DW      MENUNO+80           ;-> VCR/20" POWER ON
            DW      MENUNO+21           ;-> PRINTER CLEAR MEMORY
            DW      MENUNO+36           ;-> AUTO GAIN
            DW      0                   ;-> SPARE
;
            DW      MENUNO+62           ;-> PRINTER FONT ON/OFF (+1)
            DW      MENUNO+66           ;-> PRINTER VIDEO SELECT R-B-G
            DW      MENUNO+76           ;-> PRINTER CLEAR CAPTIONS
            DW      MENUNO+63           ;-> PRINTER FREEZE
            DW      MENUNO+64           ;-> PRINTER PRINT
            DW      MENUNO+65           ;-> PRINTER UNFREEZE
            DW      MENUNO+67           ;-> PRINTER GET RIBBON LEFT
            DW      MENUNO+46           ;-> 9" VIDEO ON/OFF
;
            DW      MENUNO+15           ;-> IRIS LEVEL (+2)
            DW      MENUNO+84           ;-> MOD 2 PARM BYTE #1 (+3)
            DW      MENUNO+48           ;-> PRINTER SHARPNESS LEVEL (+4)
            DW      MENUNO+50           ;-> PRINTER FORMAT SELECT (+5)
            DW      MENUNO+24           ;-> MONITOR INPUT SELECT LEVEL
(MENU) (+6)
            DW      MENUNO+27           ;-> MONITOR VOLUME LEVEL (+7)
            DW      MENUNO+86           ;-> MOD 2 PARM BYTE #2 (+8)
            DW      MENUNO+33           ;-> BEEP VOLUME LEVEL (+9)
            DW      MENUNO+53           ;-> PRINTER RED LEVEL (+10)
            DW      MENUNO+55           ;-> PRINTER BLUE LEVEL (+11)
            DW      MENUNO+57           ;-> PRINTER GREEN LEVEL (+12)
            DW      MENUNO+59           ;-> PRINTER LIGHT LEVEL (+13)
            DW      MENUNO+61           ;-> PRINTER DARK LEVEL (+14)
            DW      MENUNO+44           ;-> PRINTER COLOR ADJUST MENU SELECT
(+15)
            DW      MENUNO+22           ;-> PRINTER IMAGE POSITION (+16)
            DW      MENUNO+78           ;-> PRINTER SEND ID CAPTION (+17)
            DW      MENUNO+68           ;-> VCR CONTROL (+18)
            DW      MENUNO+28           ;-> LAST SET (SPARE) (+19)
;
;       Parm change execution table.  Values are addresses of execution
;       routines executed when a parameter changes.  A zero value
;       indicates no execution.
;
EXRTBL      DW      EXPRFP              ;PRINTER FORMAT FULL PAGE (+0)
            DW      EXAUTOI             ;AUTO IRIS
            DW      0                   ;ID OVLY
            DW      EXTIM               ;TIMER OVLY
            DW      EXPON               ;VCR/20" POWER ON
            DW      EXPRCLM             ;PRINTER CLEAR MEMORY
            DW      EXAGAIN             ;AUTO GAIN
            DW      0                   ;SPARE
;
```

```
            DW      EXPFONT         ;PRINTER FONT ON/OFF (+1)
            DW      EXSEV           ;PRINTER VIDEO MODE (R-B-G) SELECT

DW      EXCCD           ;PRINTER CLEAR ID CAPTIONS
            DW      EXPSTORE        ;PRINTER FREEZE
            DW      EXPRNT          ;PRINTER PRINT WITH CAPTIONS
            DW      EXPRUFZ         ;PRINTER UNFREEZE
            DW      EXPRGRL         ;PRINTER GET RIBBON LEFT
            DW      EXSMV           ;9" VIDEO ON/OFF
;
            DW      EXIRIS          ;IRIS LEVEL (+2)
            DW      0               ;MOD 2 PARM BYTE #1 (+3)
            DW      EXPRSH          ;PRINTER SHARPNESS LEVEL (+4)
            DW      EXPRFOR         ;PRINTER FORMAT SELECT (+5)
            DW      EXMSEL          ;MONITOR INPUT SELECT LEVEL
(MENU)(+6)
            DW      EXMONVOL        ;MONITOR VOLUME LEVEL (+7)
            DW      0               ;MOD 2 PARM BYTE #2 (+8)
            DW      EXBEEPVS        ;BEEP VOLUME LEVEL (+9)
            DW      EXCADJR         ;PRINTER RED LEVEL (+10)
            DW      EXCADJB         ;PRINTER BLUE LEVEL (+11)
            DW      EXCADJG         ;PRINTER GREEN LEVEL (+12)
            DW      EXCADJL         ;PRINTER LIGHT LEVEL (+13)
            DW      EXCADJD         ;PRINTER DARK LEVEL (+14)
            DW      EXCFONX         ;COLOR ADJUST MENU SELECT (+15)
            DW      EXPRIPOS        ;PRINTER IMAGE POSITION (+16)
            DW      EXSENDC         ;PRINTER SEND ID CAPTION (+17)
            DW      EXVCREX         ;VCR CONTROL (+18)
            DW      LASTSET         ;LAST SET (SPARE) (+19)
;
;       Initialization table.
;
PINTBL      DB      2,1             ;PRINTER FORMAT FULL PAGE (+0)
            DB      4,0             ;AUTO IRIS
            DB      2,0             ;ID OVERLAY
            DB      2,0             ;TIMER OVERLAY
            DB      2,1             ;VCR/20" POWER ON
            DB      2,1             ;PRINTER CLEAR MEMORY
            DB      2,0             ;AUTO GAIN
            DB      0,0             ;SPARE
;
            DB      2,1             ;PRINTER FONT ON/OFF (+1)
            DB      2,1             ;PRINTER VIDEO SELECT R-B-G
            DB      2,1             ;PRINTER CLEAR ID CAPTIONS
            DB      1,0             ;PRINTER STORE/FREEZE
            DB      1,0             ;PRINTER PRINT WITH CAPTIONS
            DB      2,1             ;PRINTER UNFREEZE
            DB      2,1             ;PRINTER GET RIBBON LEFT
            DB      4,0             ;9" VIDEO ON/OFF
;
            DB      4,0             ;IRIS LEVEL (+2)
            DB      0,0             ;MOD 2 PARM BYTE #1 (+3)
            DB      4,0             ;PRINTER SHARPNESS LEVEL (+4)
            DB      0,0             ;PRINTER FORMAT SELECT (+5)
            DB      4,0             ;MONITOR INPUT SELECT LEVEL (MENU)(+6)
            DB      2,0             ;MONITOR VOLUME LEVEL (+7)
```

```
;
;
BLK00A      DB      2                               ;OLD/NEW ID SET-UP
            DB      0,0                             ;TYPE CODE
            DW      MENUNO+12                       ;-> MENU # (EXT RAM)
            DB      0,0                             ;MIN-MAX VALUE
            DW      MENU00A                         ;MENU ->
            DW      RECALLN,RECALLY                 ;NEXT BLOCK ->
;
BLK041      DB      1                               ;MANUAL IRIS LEVEL 2
            DB      2                               ;TYPE CODE
            DW      MENUNO+14                       ;-> MENU # (EXT RAM)
            DB      -25,25                          ;MIN-MAX VALUE
            DW      MENU041                         ;MENU ->
            DW      EXRTSND                         ;NEXT BLOCK ->
;
BLK050      DB      2                               ;TIMER DISPLAY ON/OFF
LEVEL 2
            DB      0,0                             ;TYPE CODE
            DW      MENUNO+16                       ;-> MENU # (EXT RAM)
            DB      0,0                             ;MIN-MAX VALUE
            DW      MENU050                         ;MENU ->
            DW      EXRTS,EXRTSND                   ;NEXT BLOCK ->
;
;
BLK060      DB      4                               ;PRINTER SET-UP SELECT
LEVEL 2
            DB      0,1,0,0                         ;TYPE CODE
            DW      MENUNO+42                       ;-> MENU # (EXT RAM)
            DB      0,0                             ;MIN-MAX VALUE
            DW      MENU060                         ;MENU ->
            DW      EXRTSND,BLK060A                 ;NEXT BLOCK ->
            DW      EX060C,EXSFI
;
BLK060A     DB      5                               ;PRINTER COLOR SELECT
LEVEL 3
            DB      0,0,0,0,0                       ;TYPE CODE
            DW      MENUNO+44                       ;-> MENU # (EXT RAM)
            DB      0,0                             ;MIN-MAX VALUE
            DW      MENU060A                        ;MENU ->
            DW      EX060AA,EX060AB                 ;NEXT BLOCK ->
            DW      EX060AC,EX060AD,EX060AE
;
BLK060C     DB      3                               ;PRINTER SHARPNESS LEVEL
3
            DB      0,0,0                           ;TYPE CODE
            DW      MENUNO+48                       ;-> MENU # (EXT RAM)
            DB      0,0                             ;MIN-MAX VALUE
            DW      MENU060C                        ;MENU ->
            DW      EX060,EX060,EX060               ;NEXT BLOCK ->
;
BLK060D     DB      3                               ;PRINTER FORMAT LEVEL 3
            DB      0,0,0                           ;TYPE CODE
            DW      MENUNO+50                       ;-> MENU # (EXT RAM)
            DB      0,0                             ;MIN-MAX VALUE
            DW      MENU060D                        ;MENU ->
```

```
              DW      EX060,EX060,EX060             ;NEXT BLOCK ->
;
;
;
BLK060AA        DB      1                       ;PRINTER R COLOR LEVEL 4
                DB      2                       ;TYPE CODE
                DW      MENUNO+52               ;-> MENU # (EXT RAM)
                DB      0,15                    ;MIN-MAX VALUE
                DW      MENU60AR                ;MENU ->
                DW      EX060                   ;NEXT BLOCK ->
;
;
BLK060AB        DB      1                       ;PRINTER B COLOR LEVEL 4
                DB      2                       ;TYPE CODE
                DW      MENUNO+54               ;-> MENU # (EXT RAM)
                DB      0,15                    ;MIN-MAX VALUE
                DW      MENU60AB                ;MENU ->
                DW      EX060                   ;NEXT BLOCK ->
;
;
BLK060AC        DB      1                       ;PRINTER G COLOR LEVEL 4
                DB      2                       ;TYPE CODE
                DW      MENUNO+56               ;-> MENU # (EXT RAM)
                DB      0,15                    ;MIN-MAX VALUE
                DW      MENU60AG                ;MENU ->
                DW      EX060                   ;NEXT BLOCK ->
;
BLK060AD        DB      1                       ;PRINTER LIGHT LEVEL 4
                DB      2                       ;TYPE CODE
                DW      MENUNO+58               ;-> MENU # (EXT RAM)
                DB      0,15                    ;MIN-MAX VALUE
                DW      MENU60AL                ;MENU ->
                DW      EX060                   ;NEXT BLOCK ->
;
BLK060AE        DB      1                       ;PRINTER DARK LEVEL 4
                DB      2                       ;TYPE CODE
                DW      MENUNO+60               ;-> MENU # (EXT RAM)
                DB      0,15                    ;MIN-MAX VALUE
                DW      MENU60AD                ;MENU ->
                DW      EX060                   ;NEXT BLOCK ->
;
BLK062          DB      3                       ;MONITOR SET-UP LEVEL 2
                DB      1,1,1                   ;TYPE CODE
                DW      MENUNO+30               ;-> MENU # (EXT RAM)
                DB      0,0                     ;MIN-MAX VALUE
                DW      MENU062                 ;MENU ->
                DW      BLK0A,BLK062A,BLK062B   ;NEXT BLOCK ->
;
BLK062A         DB      2                       ;MONITOR SET-UP LEVEL 3
                DB      0,0                     ;TYPE CODE
                DW      MENUNO+24               ;-> MENU # (EXT RAM)
                DB      0,0                     ;MIN-MAX VALUE
                DW      MENU062A                ;MENU ->
                DW      EXRTS,EXRTS             ;NEXT BLOCK ->
;
BLK062B         DB      2                       ;MONITOR SELECT LEVEL 3
```

```
              DB    0,0              ;TYPE CODE
              DW    MENUNO+46        ;-> MENU # (EXT RAM)
              DB    0,0              ;MIN-MAX VALUE
              DW    MENU062B         ;MENU ->
              DW    EXRTS,EXRTS      ;NEXT BLOCK ->
;
BLK063        DB    1                ;BEEP VOLUME LEVEL 2
              DB    10               ;TYPE CODE
              DW    MENUNO+32        ;-> MENU # (EXT RAM)
              DB    -10,10           ;MIN-MAX VALUE
              DW    MENU063          ;MENU ->
              DW    EXRTSND          ;NEXT BLOCK ->
;
BLK064        DB    2                ;CAMERA SET-UP LEVEL 2
              DB    1,1              ;TYPE CODE
              DW    MENUNO+34        ;-> MENU # (EXT RAM)
              DB    0,0              ;MIN-MAX VALUE
              DW    MENU064          ;MENU ->
              DW    BLK064A,BLK064B  ;NEXT BLOCK ->
;
BLK064A       DB    2                ;AUTO GAIN LO-HI LEVEL 3
              DB    0,0              ;TYPE CODE
              DW    MENUNO+36        ;-> MENU # (EXT RAM)
              DB    0,0              ;MIN-MAX VALUE
              DW    MENU064A         ;MENU ->
              DW    EXRTS,EXRTS      ;NEXT BLOCK ->
;
BLK064B       DB    2                ;WHITE BAL LEVEL 3
              DB    0,0              ;TYPE CODE
              DW    MENUNO+38        ;-> MENU # (EXT RAM)
              DB    0,0              ;MIN-MAX VALUE
              DW    MENU064B         ;MENU ->
              DW    EXWHBAL,EXWHBAL  ;NEXT BLOCK ->
;
BLK065        DB    4                            ;INIT/STATUS TITLE LEVEL 0
              DB    9,9,9,9          ;TYPE CODE
              DW    MENUNO+70        ;-> MENU # (EXT RAM)
              DB    0,4              ;MIN-MAX VALUE
              DW    MENU65           ;MENU ->
              DW    0,LAMPHR,SYSHR,RIBBONA   ;NEXT BLOCK ->
;
BLK066        DB    1                ;DISPLAY RIBBON LEFT LEVEL 0
              DB    9                ;TYPE CODE
              DW    MENUNO+72        ;-> MENU # (EXT RAM)
              DB    0,0              ;MIN-MAX VALUE
              DW    MENU66           ;MENU ->
              DW    RIBBONA          ;NEXT BLOCK ->
;
BLK067        DB    1                ;DISPLAY PRINT ERROR LEVEL 0
              DB    9                ;TYPE CODE
              DW    MENUNO+74        ;-> MENU # (EXT RAM)
              DB    0,1              ;MIN-MAX VALUE
              DW    MENU67           ;MENU ->
              DW    PRERRA           ;NEXT BLOCK ->
;
```

```
BLK068          DB    1                  ;CBAR MENU DISPLAY
                DB    11                 ;TYPE CODE (?)
                DW    MENUNO+82          ;-> MENU # (EXT RAM)
                DB    0,0                ;MIN-MAX VALUE
                DW    MENU60AA           ;MENU ->
                DW    CBAREXIT           ;NEXT BLOCK ->
;
MENU0           DB '   SYSTEM STATUS     $'   ;TOP LEVEL LEVEL 0
                DB '   AUTO SET-UP       $'
                DB '   PATIENT ID        $'
                DB '   NORMALIZE SYSTEM  $'
                DB '   VCR               $'
                DB '   AUTO IRIS         $'
                DB '   TIMER             $'
                DB '   SYSTEM SET-UP     $'
                DB '   COLOR BAR         $'
                DB '   EXIT MENUS        $'
;
MENU0A          DB '   ADJUST VOLUME -+  $'   ;VOLUME ADJUST LEVEL 1
;
MENU00A         DB 'SAME SYSTEM SET-UP   $'   ;PATIENT ID RECALL LEVEL
2
                DB 'LOAD FILE FOR SET-UP$'
;
MENU03          DB '   VCR RECORD        $'
                DB '   VCR STOP          $'
                DB '   VCR REWIND        $'
                DB '   VCR PLAY          $'
                DB '   VCR STOP          $'
                DB '   VCR FAST FORWARD  $'
;
MENU04          DB '   IRIS AUTO MODE    $'
                DB '   IRIS MANUAL MODE  $'
;
MENU05          DB '    TIMER RUN        $'
                DB '    TIMER STOP       $'
                DB '    TIMER RESET-RUN  $'
;
MENU06          DB '   PRINTER SET-UP    $'
                DB '   MONITOR SET-UP    $'
                DB '   CAMERA SET-UP     $'
                DB '   BEEPER SET-UP     $'
;
MENU041         DB '   IRIS SET !!!!     $'   ;MANUAL IRIS LEVEL 2
;
MENU050   DB ' TIMER DISPLAY OFF   $'   ;TIMER DISPLAY ON/OFF LEVEL 2
          DB ' TIMER DISPLAY ON    $'
;
MENU060         DB ' EXIT MENU          $'   ;PRINTER SELECT LEVEL 2
                DB ' SET COLOR/CONTRAST $'
                DB ' SET SHARPNESS      $'
                DB ' SET FULL/SPLIT     $'
;
MENU060A  DB ' ADJUST RED          $'   ;PRINTER COLOR SELECT LEVEL 3
```

```
              DB ' ADJUST BLUE           $'
              DB ' ADJUST GREEN          $'
              DB ' ADJUST LIGHT          $'
              DB ' ADJUST DARK           $'
;
MENU060C  DB ' SHARPNESS LO          $'    ;PRINTER SHARPNESS LEVEL 3
              DB ' SHARPNESS MED         $'
              DB ' SHARPNESS HI          $'
;
MENU060D  DB ' FULL IMAGE            $'    ;PRINTER FORMAT LEVEL 3
              DB ' SPLIT IMAGE 4         $'
              DB ' SPLIT IMAGE 9         $'
;
MENU60AA  DB '                       $'    ;PRINTER ADJUST LEVEL 4
;
MENU60AR  DB 'RED !!!!               $'    ;COLOR ADJUST RED
MENU60AB  DB 'BLUE !!!!              $'    ;COLOR ADJUST BLUE
MENU60AG  DB 'GREEN !!!!             $'    ;COLOR ADJUST GREEN
MENU60AL  DB 'LIGHT !!!!             $'    ;COLOR ADJUST LIGHT
MENU60AD  DB 'DARK !!!!              $'    ;COLOR ADJUST DARK
;
MENU062       DB ' MONITOR VOLUME        $'    ;MONITOR SET-UP LEVEL 2
              DB ' RGB - COMPOSITE       $'
              DB ' SMALL MONITOR VIDEO$'       ;9" VIDEO ON/OFF
;
MENU062A  DB ' RGB SELECT            $'    ;MONTIOR SET-UP LEVEL 3
              DB ' COMPOSITE SELECT      $'
;
MENU062B      DB ' VIDEO ON              $'    ;9" VIDEO
              DB ' VIDEO OFF             $'
;
MENU063       DB ' BEEP VOLUME !!!!      $'    ;BEEP VOLUME LEVEL 2
;
MENU064       DB ' AUTO GAIN             $'    ;CAMERA SET-UP LEVEL 2
              DB ' WHITE BALANCE         $'
;
MENU064A      DB ' AUTO GAIN LO          $'    ;AUTO GAIN LEVEL 3
              DB ' AUTO GAIN HI          $'
;
MENU064B      DB ' SET WHITE BALANCE     $'    ;WHITE BALANCE LEVEL 3
              DB ' EXIT MENU             $'
;
;
MENU65        DB '                       $'    ;STATUS TITLE (2 LISTS)
CODE #0
              DB '   LAMP HOURS: !!!!    $'    ;PRINTER ON LINE
              DB 'SYSTEM HOURS: !!!!     $'
              DB 'PRINT RIBBON: !!!!     $'
;
              DB '                       $'    ;CODE #1
              DB '   LAMP HOURS: !!!!    $'    ;PRINTER OFF LINE
              DB 'SYSTEM HOURS: !!!!     $'
              DB 'PRINTER IS OFF LINE    $'
;
MENU66        DB '   RIBBON LEFT !!!!    $'    ;RIBBON LEFT
;
```

```
MENU67          DB '    PRINTER BUSY     $'    ;PRINT ERROR LIST
CODE(0)
                DB '    PRINTER ERROR    $'    ;CODE (1)
                DB '    PRINTER OFF LINE $'    ;CODE (2)
                DB '    PRINTER ON LINE  $'    ;CODE (3)
                DB '    PRINTER OFF      $'    ;CODE (4)
                DB '    WAND ENTRY ERROR $'    ;CODE (5)
;
LOGOMSG         DB 'ARTHROTEK I.E.S 1000$'     ;MESSAGES
TIMEM           DB '         !!:!!:!!$'
TIMEMM          DB '!!:!!:!!          $'
CKVCR           DB '    CHECK VCR TAPE  $'
SETSYS          DB '    SETTING SYSTEM  $'
SETNORM         DB ' NORMALIZING SYSTEM $'
TSTOP           DB '    TIMER STOPPED   $'
VCRREC          DB '    VCR RECORD      $'
VCRSTOP         DB '    VCR STOP        $'
        END
```

4. SUBROUTINES

The following are the various subroutines which are used by the Imaging Unit 12.

'AUTOIDX'

This routine displays the Auto ID (AUTOFILE) on row #5 as a centered overlay provided it is set ON else NOP. Entry at AUTOIDX2 displays the ID unconditionally, but the Row # must be loaded.

'BEEP'

This routine controls the beeper. Enter with BEEPCMND as follows:

```
        BEEPCMDN  = 0 off
                  = 1 short
                  = 2 short in progress
                  = 3 long
                  = 4 long in progress
                  = 5 op error
                  = 6 op error in progress
                  = 7 forced off period
```

Following a short or long beep duration, the beep is turned off and BEEPCMND is set = 0. Volume is set to the level of MENUNO+33 provided flag FLAG3:7 is set, after which it is cleared.

'BEEPER'

This routine arbitrates and controls the beeper.

'BINASC'

This routine returns four ASCII hexadecimals in buffer DIGBUF from a 16 bit binary number entered in R0:R1.

'BINBCD'

This routine converts a 16 bit unsigned binary number contained in register pair R0:R1 into a packed six digit BCD number returned in R2:R3:R4.

'BLANKRNB'

This routine blanks an entire row at ROW and sets the row color transparent unless FLAG10:D7=1 then background = BK9.

'BLANKROW'

This routine blanks an entire row at ROW and sets the row color transparent.

'BUFINIT'

This routine flushes all input and output buffers.

'CALCFILE'

This routine calculates the index for the ASCII data of the current entry of the AUTO/PID ID files and returns it in R14:R15. Enter with R14:R15 -> file base (AUTOFILE or PATFILE).

'CAPDIS'

This routine displays the print caption zones Z1 thru Z7 on rows Z3-Z7.

'CAPLOAD'

This routine loads the current ID at file -> R14:R15 to buffer CAPTION1 and then sends the buffer to the printer.

'CAPMOVE'

This routine moves 20 characters from a file at R14:R15 -> to the Print Caption field at zone R2 (0-7).

'CBAR'

This routine displays the color bar test pattern for CBTEST looptimes after which the test complete flag (FLAG4:0) is set.

'CBAREXIT'

This routine inits the normal screen pattern and executes a normal exit.

'CBARON'

This routine displays the color bar test pattern as a menu selection. Exit is to BLK068.

'CFFULL'

This routine displays the File Full message for ID files on Row #0 and sets the file full displayed flag. The ID buffer is cleared.

'CKEPCRC'

This routine checks R4 bytes of run time code from 0000H to EPTOPA. When completed, flag FLAG10:D3 is set. Enter with R14:R15 -> EPTOPA - 2 at CKEPCX to calculate CRC, CKEPCRC to check CRC. Break at CKEPCY to return CRC in R10:R11. Note: EPCRCH:EPCRCL and EPCRCAH:EPCRCAL must be zeroed prior to the first test entry.

'CLEARROW'

This routine blanks a row at ROW and sets row and character color = R0.

'CLIDBUF'

This routine clears the ID Buffer at -> FPTRTEMP (PATFILE or AUTOFILE) by loading it with <SP>.

'CLROW0'

This routine clears Row #0 for ID file functions.

'CLS'

This routine clears all rows and sets the background transparent.

'CLSNB'

This routine clears all rows and sets the background transparent unless FLAG10:D7=1 then background=BK9.

'COLD'

This routine is the cold start initialization.

'DBLOCK1'

This routine displays a menu block. The display consists of rows #0 and #7 blank. Row #1 thru row #6 are menu rows displayed as follows:

1) The entry row ENTNO is highlighted with row background color MNUHL.
2) The start row (#1) is displayed as ENTNO = 0 for NOENT <=6 or ENTNO -3 < 0 else as ENTNO - 3.
3) The last row (#6) is displayed as the start row + 5.
4) All rows > NOENT are blanked.
5) Screen background color = MNUBKG.
6) Character color = MNUCC.

'DBLOCK2'

This routine displays a menu block. A single menu is displayed at row #3. Rows #0,2-7 are unchanged. If a '!!!!' string exists within the displayed menu, it is replaced with the contents of the external ram VALUE number corresponding to that menu. The menu is centered unless the no center flag FLAG8:4 is set. If DB2COLOR = 0 then screen background is transparent else it is set to MNUBKG2.

```
MNUHL2    = row highlight color
MNUBKG2   = screen background color
MNUCC2    = character color
```

'DBLOCK3'

This routine displays a menu block for PID and AUTO ID file entry. The display consists of rows #1 and #7 blank. Row #0 (PID/AUTO ID input) is left unmodified. Rows #2 thru #6 are PID/AUTO ID's displayed as follows:

1) The entry row ENTNO is highlighted with row background color PMNUHL.
2) The start row (#2) is displayed as ENTNO = 0 for NOENT <=5 or ENTNO -2 < 0 else as ENTNO - 2.
3) The last row (#6) is displayed as the start row + 4.
4) All rows > NOENT are blanked.
5) Screen background color = PMNUBKG.
6) Character color = PMNUCC.

Note: NOENT and ENTNO are retrieved from the PID/AUTO data file.
Enter with FPTRTEMP -> file (PATFILE or AUTOFILE).

'DBLOCK4'

This routine displays a menu block. A single menu is displayed at
row ROW and centered. If a '!!!!' string exists within the displayed
menu, it is replaced with the contents of the external ram VALUE
number corresponding to that menu. Enter with DB4COLOR as follows:

DB4COLOR   = 0       transparent, character color = OVLYCC
                      = 1       transparent screen background
                                row background = OVLYHL
                                character color = OVLYCC2

If FLAG10:D7=1 background = BK9 else transparent.

'DBLOCK5'

This routine displays a menu block. The number of menus designated
by the block is displayed as an overlay starting at row #0. If a
'!!!!' string exists within the menu it is replaced by a 4 digit
number value. This value is derived from a 16 bit value residing in
external ram at an address pointed to by the next block list of the
menu block. The menu is from a menu list. The list chosen is
determined by the menu select value (ENTNO). All lists must be
sequential and contain the same number of menus (NOENT).

Transparent, Color = STATCOL

'DBLOCK6'

This routine displays a menu block. Operation is identical to
DBLOCK2 except on a screen background of MNUBKG2 rather then
transparent background and the menu is not centered.

'DBLOCK7'

This routine is a no message menu display. The screen is cleared,
background set transparent. Row and character color are set to
DB7COLOR (0=transparent).

'DISCHAR'

This routine loads an ASCII character contained in register R0 at row
ROW (0-7) and column COL (0-19) into the video store. The character
and row colors are unchanged.

'DISCLEAR'

This routine blanks all characters of all 8 rows and sets all row colors to transparent.

'DISINIT'

This routine initializes the display OSD registers to a group of values contained in a table at ->@RR12. The display attribute (FC03H), the bar control (FC06H) and bar position (FC07H) values are also loaded to the Video Ram Store.

'DISLOAD'

This routine loads the entire cpu video ram with the contents of the external ram video store and also the display attribute register, bar control register and bar position register. This routine is intended to immediately follow a wait for vertical sync interrupt such that it is executed during the vertical retrace. The screen attributes are always loaded, but either the first four rows (FLAG2:6=0) or the second four rows (FLAG2:6=1) are loaded according to the video load toggle flag. This keeps load time under the vertical retrace period. FLAG1:4 is cleared only after the last four rows have been loaded.

'DISPLAY'

This routine waits for the vertical retrace sync then loads the CPU video ram if the load enable flag (FLAG1:4) is set. The load is in two sections (1st and last 4 rows) after which FLAG1:4 is cleared. This imposes a loop time of 1/60sec if no display load occurs and 1/30sec if one does.

'DISPRE'

This routine displays the print error as an overlay. Enter with R0 as follows:

```
            R0 = 0        printer busy
               = 1        printer error
               = 2        printer off line
               = 3        printer on line
               = 4        printer off
               = 5        wand entry error
```

'DISTATUS'

This routine clears the screen and displays the status as an overlay. The printer on-off line (FLAG6:2) and the shaver on-off line (FLAG2:0) determine which menu list is displayed.

'DISTYPE'

This routine displays a menu characterized by the menu block list which must be loaded at the time of entry according to menu type (ENTYPE), entry # (ENTNO) and menu (MNUPTR). For certain menu types, the value (VALNO) is also displayed.

'DMESS'

This routine displays a message at -> R10:R11, row ROW with character color DMESSC on a transparent background unless FLAG10:D7=1 then background = BK9.

'DRIBBON'

This routine displays the ribbon left as an overlay. If in the menu, overlay or AI display mode then NOP and return carry set else clear.

'DSPYON'

This routine turns the display and background on/off. Enter as follows:

```
            R0    = 0   transparent (background off)
                  = 1   black
                  = 2   blue
                  = 3   green
                  = 4   cyan
                  = 5   red
                  = 6   magenta
                  = 7   yellow
                  = 8   white carry = 0   display off
                  = 1   display on
```

'DTRINIT'

This routine loads the DTR save byte DTRSAV with the complement of the DTR bits contained in the SIO command byte array SIOCMRSV.

'DTRSET'

This routine sets the SIO DTR bit in DTRSAV, the SIO and the command write save array (SIOCMRSV) to the contents of the R0 register on entry:

|       | d4      | d3     | d2      | d1   | d0     |
|-------|---------|--------|---------|------|--------|
|       | /ovlena | intlmp | /whbal  | uuen | /airis | d5-d7 = don't care

```
d0 = 0        auto iris = auto
d1 = 1        /uuen out = 0   (unit-unit enable on)
d2 = 1        /whbal    = 0   (0 pulse white balance on)
d3 = 1        select internal lamp
d4 = 0        select overlay on
```

'ENTRY'

This routine sets up parameters for entry into the test loop.

```
V2.4
CRC =9E81H
```

'EPTOP'

This module contains the Program Eprom CRC and must be placed as the last run time module with CRC HI then CRC LO bytes of the Program CRC. The CRC is calculated using routine CKEPCRC.

'ERAMTEST'

This routine checks external ram from 4000H-5FFFH.

'ETIMERN'

This routine updates the elapsed timer display each second provided the elapsed timer flag is set (FLAG1:1=1) and the normal display page flag is set (FLAG1:2=1) else NOP.

'ETIMERM'

This routine updates the elapsed timer display each second for the timer menu mode. The timer is displayed on row ETMROW and column ETMCOL. Character color is ETMCOLOR. The system must be in timer menu display else NOP. The system and lamp elapsed time is incremented in this routine.

'EXAGAIN'

This routine executes the auto gain hi-lo function.

'EXAUTOI'

This routine loads the Iris select port auto (AIRIS=1) or manual (AIRIS=0) according to the state of menu select MENUNO+6.

'EXBEEPVS'

This routine enables the short beep with volume set.

'EXCADJ'

This routine outputs the contents of MENUNO+53 thru MENUNO+61 as color levels for R,B,G,L,D when entry is at EXCADJR,EXCADJB EXCADJG,EXCADJL,EXCADJD respectively to the printer.

'EXCAMS'

This routine selects monitors as 20"=9"= print freeze input. Return is to menu blocks BLK060AA thru BLK060AE. Entry at EX060 returns 20"=9" = real time input with exit to BLK060.

'EXCCD'

This routine clears printer captions memory and sets the UNFREEZE parameter on. This is necessary since each clear of printer captions results in a locked unsync state until an unfreeze command is issued.

'EXCFONX'

This routine outputs the selected color adjust level of block BLK060A (MENUNO+44) to the printer.

'EXIRIS'

This routine sets iris parameters. If IRIS is set auto mode, line AIRIS is set HI else LO. The contents of the manual iris VALNO (MENUNO+15) is loaded to port PWM10.

'EXLAMP'

This routine sets /CTEMPEXT HI if the internal lamp line P_2 is HI (EXT Lamp) else /CTEMPEXT is set LO (INT Lamp).

'EXMONVOL'

This routine controls the 20" monitor (system) volume initiated by changes of MENUNO+27.

'EXMSEL'

This routine selects the video input for the 20" monitor:
```
        parm #20   = 0     R-B-G Line B
                   = 1     Composite Line A
```

The routine executes for changes in MENUNO+24.

'EXNORM'

This routine normalizes the system save parameters from table NORMTBL. The normalize in progress flag (FLAG7:3) is set and the normalizing system message displayed.

'EXPFONT'

This routine sets the printer font on/off.

'EXPON'

This routine sets the 20" monitor and VCR power-on.

'EXPRCLM'

This routine clears the video frame of printer memory and then displays the memory (freeze) mode. The clear command is then reset.

'EXPRE'

This routine is used to set-up for printer execution. If the printer is executing another routine, the print error flag (FLAG2:5) is set and carry is returned set else clear. R14:R15 is returned -> menuno indexed by R0 on entry. R0 is returned with the indexed MENUNO value.

'EXPRFOR'

This routine selects the printer format as full, split4 or split9 or 1, 4, or 9 images in freeze frame according to the menu set of MENUNO+50. The printer image position (MENUNO+22) is set to zero since the printer does likewise.

'EXPRFP'

This routine formats the printer for full page mode regardless of the format set by MENUNO+50. The command is cleared following execution.

'EXPRGRL'

This routine gets the amount of printer ribbon left which is returned in PRIBLEFT:PRIBLEFT+1. After execution the command is reset.

'EXPRIPOS'

This routine sets the printer memory store target based on
the printer image position value (MENUNO+22). If the image
position exceeds #3 for SPLIT4 mode or #8 for SPLIT9 mode or
0 for full mode, the image position is zeroed else the image
position is set to MENUNO+22 for SPLIT4 or SPLIT9 modes.

'EXPRNT'

This routine issues a print with caption to the printer. The
command is then cleared. Note: this command also freezes the
display which must then be cleared using the un-freeze command.

'EXPRSH'

This routine sends the sharpness selected to the printer as
a function of MENUNO+48 (lo-med-hi).

'EXPRUFZ'

This routine sends an unfreeze message to the printer. The
unfreeze command is then reset.

'EXPRVPR'

This routine prevents entry to the printer set-up menu in the
event the printer is printing, off-line or malfunctioning.
If invalid, a print error message is displayed as an overlay
and return to the normal mode established else exit is to
BLK060 (normal operation).

'EXPSTORE'

This routine stores a video frame to printer memory and then
displays the memory (freeze) mode. The store-freeze command
is then reset.

'EXRTS'

This routine is an exit execute from the menu mode. The
screen is blanked, set transparent and the display mode
changed to overlay. The menu at the current entry number
(ENTNO) is displayed as an overlay at row #0 for 3 seconds.

'EXRTSND'

This routine is an exit execute from the menu mode. The screen is blanked and the display mode changed to normal.

'EXSENDC'

This routine sends a 160 byte string of print captions data located in External Ram at address CAPTION1 to the printer.

'EXSEV'

This routine selects the R-B-G video printer mode. The set command is cleared after execution.

'EXSFI'

This routine sets the printer image select to full mode, clears memory and then unfreezes the display. The menu image select (MENUNO+50) is also set to full mode. This insures a memory clear operation each time the image format is changed. Exit is to menu block BLK060D.

'EXSIO'

This routine controls external SIO access. A string sent to the Imager is 3 bytes:
- 1st Address Lo
- 2nd Address Hi + Code
- 3rd Data The HI address field is 4 bits (Lo nibble), the Code field is 4 bits (HI nibble).

Codes:
- 0   ram read
- 1   ram write
- 2   ext ram read (0-7FFH)
- 3   ext ram write (0-7FFH)
- 4   eprom read (0-FFFH)
- 5   enable switch ops (ext sio)
- 6   disable switch ops (int sio)
- 7   log on
- 8   standby toggle
- 9   call DATA:AL
- 10  easedrop UU IN toggle
- 11  easedrop UU OUT toggle
- 12  easedrop PRINTER IN toggle
- 13  easedrop PRINTER OUT toggle
- 14  easedrop WAND IN toggle
- 15  easedrop KEYBOARD IN toggle LOGON is an AAH in the data field which sets flag (FLAG10:D1). If the system is not logged on, all other commands are ignored.

'EXSMV'

This routine clears (9" video on) or sets (9" video off) the 9" video flag (FLAG10:D7). Return is to EXRTS.

'EXTIM'

This routine controls the elapsed timer overlay display.

'EXTSET'

This routine starts, stops or reset-starts the timer for entries at EXTSET1,EXTSET2 or EXTSET3 respectively.

'EXVCREX'

This routine outputs VCR commands with any change of the VCR control parameter (#32) at MENUNO+68. The 20" monitor is set to L1 for VCR = PLAY else to the RBG or COMPOSITE state of MENUNO+24.

'EXVCRLO'

This menu block prevents VCR menu entry if printing else BLK03 is loaded and the VCR stopped.

'EXVCROP'

This routine controls the operating functions of the VCR by transfering the contents of the vcr menu select (MENUNO+4) to the vcr control parameter (MENUNO+68) which initiates vcr control output.

'EXWHBAL'

This routine executes white balance set. If the menu is for white balance set, WHBAL is pulsed Lo and timer WBALC preset. If the exit menu is set, it is reset to white balance set and no pulse generated.

'FATAL'

This is the terminal error handler.

'FLUSHIN'

This routine flushes one of the five SIO input buffers, sets the corresponding E flag (buffer empty) and clears the corresponding F flag (buffer full). Enter with the SIO channel number in register R0:

```
R0  = 0  wand
    = 1  U-U
    = 2  Ext
    = 3  Printer
    = 4  Keyboard
```

Note: the IRQ3 interrupt is disabled during this routine.

'FLUSHOUT'

This routine flushes one of the five SIO output buffers, sets the corresponding E flag (buffer empty) and clears the corresponding F flag (buffer full). Enter with the SIO channel number in register R0:

```
R0  = 0  wand
    = 1  U-U
    = 2  Ext
    = 3  Printer
    = 4  Cbuss
```

Note: Interrupt IRQ3 is disabled during this routine.

'FPSWIN'

This routine returns a switch code corresponding to a key press from the front panel. The keypress must remain constant for two sequential entries else no change (debounce). The switch code is returned in ram variable FPSWITCH as:

```
FPSWITCH = 0   none
         = 1   auto iris
         = 2   print
         = 3   menu enter
         = 4   menu down
         = 5   menu up
         = 32  crosskey
```

'GENCRC'

This routine generates a CRC for each byte entered in R1 and returns it at RR10.

'GETDSR'

This routine returns the status of the SIO DSR input terminals in register R0 and DSRSAV:

```
SIO #1   D0   IRI, /autoiris
SIO #2   D1   UURTS (1 = shaver on-line)
SIO #3   D2   Spare 1
```

```
SIO #4    D3    Spare 2
SIO #5    D4    PDTR (1 = printer connected)
```

Bits D5-D7 = 0.

The UURTS input is copied to the Shaver On-Line Flag (FLAG2:D0).

'GETJUMP'

This routine forms a jump address returned in R0:R1 from
an index entered in R0 and a table address entered in R14:R15.

'GETKB'

This routine returns an ASCII character in R0 with carry
clear from the keyboard input buffer unless the buffer is
empty or the character is not recognizable in which case
the carry is returned set. The KSWITCH code is returned in
R2 for non-stored valid keys else zero.

'GETPARM'

This routine returns a parameter in R1 whose parameter number
(0-33) is contained in R0 from the last parameter set buffer
MENLAST. If the parameter number is 0-15, value R1 is a bit
(0/1) else a value (0-255).

'GUUCRC'

This routine generates a UU CRC on a string consisting of
three consequitive RMSWITCH bytes and returns it in RR10.

'GUUPCRC'

This routine generates a UU Parm CRC on a 3 byte string
-> UUPARM and returns the CRC at -> UUPARM+3.

'HEXASC'

This routine returns three ASCII characters in R2:R1:R0
from an unsigned 8 bit binary number contained in R0. If carry
is set on entry, leading edge zero suppression is executed.

'HEXASCL'

This routine returns four ASCII characters in DIGBUF thru DIGBUF+3
equal to the ASCII unsigned number 0000-9999 corresponding to
an unsigned binary number entered in R0:R1. If carry is set
on entry, leading edge zero suppression is executed.

'HEXASCS'

This routine returns four ASCII characters in DIGBUF thru DIGBUF+3 equal to a signed number -127 to +127 corresponding to a signed binary number entered in R0.

'HKEEP'

This routine is end of loop housekeeping.

'IDERASE'

This routine moves R9 files above file R0 such that file R0+1 then occupies the R0 file position which has then been effectively deleted. On entry, R14:R15 -> file (AUTOFILE or PATFILE).

'IDMOVE'

This routine moves all entries above entry # R0 one file down such that the R0-1 file then occupies the R0 file position which has been effectively deleted. Note R0 > 0 or NOP. On entry, FPTRTEMP -> AUTOFILE or PATFILE.

'IDOPS'

This routine enters an Auto Set-up ID in AUTOID into the Auto ID file. If the Auto ID to be entered is all spaces or '.', carry is returned set else clear. If the file is null, then the skip recall menu flag (FLAg6:3) is set.

Note: the routine must not be entered if the file is full.

'IDSEL'

This routine is the precursor for entry into the PID or Auto Set-up file blocks. If the respective file is empty, a null entry is made and the null entry flag set. If the file is full, the respective File Full flag is set. The ID Buffer is filled with <SP>. Exit is to BLK00C for the Auto Set-up select and BLK00B for the PID select. The request for Shaver Parameter Upload is issued.

'IDSKMNU'

This routine is entry into the yes/no recall menu.

'IRAMTEST'

This routine checks internal ram from 04H to RAMTOP.

'KEYBDOP'

This routine handles keyboard input from the SIO keyboard
input buffer. If the PID/AUTO ID menu flag (FLAG4:7) is
clear then the keyboard op error flag (FLAG5:1) is set for
all key entries except ENT, Up arrow or Down arrow.  On
the first entry with FLAG4:7 set, the keyboard, PATID/AUTOID and
the cursor (PIDCUR) is reset. Characters A-Z,'.' SP, and 0-9
are sent to buffer PATID/AUTOID at the cursor and also to the display
at row #0 and column #0. If the cursor exceeds 20 characters,
the beep is set and the character not stored. Control characters
are sent as keyboard codes to KSWITCH. ENT is honored for
the PID, normal and menu display modes.  UP or DN are honored
for only the PID and menu display modes.

```
                    A-Z, 0-9, '.',SP    stored
                    BSP (08H)   KSWITCH = 20
                    CR  (0DH)           = 21
                    UP  (5BH)           = 22
                    DN  (5DH)           = 23
                    DEL (B2H)           = 24
```

All other characters beep and perform NOP.
DEL (OMEGA=B2H) TEMP USING TAB (09H).

FPTRTEMP selects the target ID file as PATID or AUTOID.

'KTIMER'

This routine returns carry set every KTIMEHS entries for
the high speed update mode and every KTIMELS entries for
the low speed mode else carry is returned clear. A transition
from low to high speed is executed after KLOTOHI updates unless
the slow only flag (FLAG5:4) is set in which case the speed is
slow only.

'LASTSET'

This routine is a spare and occupies the last parameter
location (#33). The update complete flag (FLAG8:7) is
set.

'LOGO'

This routine displays the message at LOGOMSG in cyan on row
7 for LGTEST looptimes provided the color bar test is complete
(FLAG4:0=1) and the logo test is not complete (FLAG4:1=0) else
NOP. When the logo test is complete, flag FLAG4:1 is set and
the monitor sources are set to mode #7. TIMER0 must be initialized to LFTEST prior to first entry.

'LOGONB'

This routine displays the logo message on Row #7 provided the
9" background flag is ON (FALG10:D7=1) and the logo displayed
flag (FLAG12:D0) is clear else NOP. If entered at LOGONBX, the
display is unconditional but the Row must be loaded.

'MCENTER'

This routine centers a 20 character menu by returning a column
offset in COL. Enter with R14:R15 -> menu.

'MEMFILL'

This routine loads External Memory with R0:R1 bytes of R2
starting at address R14:R15.

'MEMMOVE'

This routine moves R0 bytes of External Memory from ->R12:R13
to ->R14:R15.

'MESS'

This routine loads a message from either Eprom (TABLES) or
cpu ram to the video ram buffer. The message start address
in Eprom is R14:R15, the video ram target row and column is
ROW and COL respectively. The message is loaded until either
an EOF character is reached ($) or the column (COL) = 20. The
column count is incremented after each character is loaded. If
a retrieved character is '!', the character is retrieved from
cpu ram at @R0 rather than Eprom and R0 is incremented.

'MESSEX'

This routine loads an ASCII string in external ram to the
the video buffer. The source string start address is R14:R15,
the video target are row = ROW and column = COL.

'MESSTO'

This routine prints a message at -> R10:R11 as a 3 second
overlay at row ROW. The overlay is cleared by routine MNUESC.
If the entry is at MESSTOV, the delay time (MNUTO) is variable
and must be loaded.

'MNUBLOCK'

This routine retrieves the following paramenters from a menu
block at R10:R11 based on the block parameters, the menu and
value numbers stored in external ram:

```
            NOENT      = # entries in this menu
            ENTYPE     = data entry type code
            ENTNO      = entry #
            MINVAL     = minimum value or zero
            MAXVAL     = maximum value or zero
            VALNO      = value
            MNUMP      = pointer to entry # and value in external ram
            MNUPTR     = pointer to menu base in tables
            NXBLK      = pointer to the next menu block in tables or
                         zero
            SKIPPTR    = pointer to the skip value list base
```

If the entry number (ENTNO) is greater than the number of
entries (NOENT), ENTNO and the entry number in external
ram are made zero (1st entry). The block pointer of the
block being loaded is saved in THISBLK. Note: display types
3 and #6 have ENTNO set = 0 unconditionally.

'MNUESC'

This routine starts a timer when the overlay or the
auto-iris set display modes are on. The timer must be
loaded at MNUTO:MNUTO+1 when any of these modes are set, and
may be re-triggered. After timeout, the normal display mode
is re-established. If entered at MNUESCX, the sequence is identical
to that of the timer timing out. Note that no menu execute is
performed when the return to normal sequence is performed.
The screen is cleared and PID re-established at exit.

'MENUDN'

This routine responds to menu down key commands according to
the menu type (ENTYPE):

1) TYPES #0,#1:  The entry number (ENTNO) is
   increased upto the maximum number of entries (NOENT).
   Slow update only.
2) TYPES #2,#4,#10,#11: The value number VALNO is decreased down
   to the minimum value (MINVAL). Slow or fast update.
3) TYPE #5: The value number VALNO is decreased without
   limit.  Slow update only.
4) TYPES #3,#6: The entry number in the patient data file
   is increased upto the maximum number of entries in the
   patient data file. Slow update only.
5) TYPE #7: NOP. Slow update only.
6) TYPE #8: Same as type #4 except slow update only.
7) TYPE #9: NOP. No update.

A command with CBAR ON exits menu.

'MENUUP'

This routine responds to menu up key commands according to the menu type (ENTYPE):

1) TYPES #0,#1: The entry number (ENTNO) is decreased down to zero. Slow update only.
2) TYPES #2,#4,#10,#11: The value number VALNO is increased upto the maximum value (MAXVAL). Slow or fast update.
3) TYPE #5: The value number VALNO is increased without limit. Slow update only.
4) TYPES #3,#6: The entry number in the patient data file is decreased down to zero. Slow update only.
5) TYPE #7: NOP. Slow update only.
6) TYPE #8: Same as #4 except slow update only.
7) TYPE #9: NOP. No update.

A command with CBAR ON exits menu.

'MNUOPEX'

This routine is used to execute a menu block. It is assumed that the system is already in the menu display mode. The type of the menu (ENTYPE) determines whether the next block address (NXBLK) is used as an execute or a next block display type. If an execute type, control is passed to that routine. If a next block type, the next block is loaded and displayed. Note that the display mode is not terminated by this routine Type #9 is a special case which performs no next block action but does immediately clear the overlay mode if it exists.

'MONITOR'

This routine sets the monitor and video sync sources.

| Mode | Sync | Description | 20" | 9" |
|---|---|---|---|---|
| #0 | printer | PFZ/Print adjust | PF OVLY ON | PF OVLY ON |
| #3 | camera | VCR Leader/CBAR/Init | RT OVLY ON | RT OVLY ON |
| #5 | printer | PFZ/Printing/PFZ Error | RT OVLY OFF | PF OVLY OFF |
| #7 | camera | All Others (default) | RT OVLY OFF | RT OVLY ON |

'MONSEL'

This routine selects the monitor and overlay functions. Enter with R0 as follows:

| R0 | *OVLENA | MONSELB | MONSELA | 20"/VCR | 9" | PRINTER |
|----|---------|---------|---------|---------|-----|---------|
| 0 | 0 | 0 | 0 | PF OVLY ON | PF OVLY ON | OVLY ON & |
| 1 | 0 | 0 | 1 | RT OVLY ON | PF OVLY ON | OVLY ON |
| 2 | 0 | 1 | 0 | PF OVLY ON | RT OVLY ON | OVLY ON |
| 3 | 0 | 1 | 1 | RT OVLY ON | RT OVLY ON | OVLY ON & |
| 4 | 1 | 0 | 0 | PF OVLY OFF | PF OVLY OFF | OVLY OFF |
| 5 | 1 | 0 | 1 | RT OVLY OFF | PF OVLY OFF | OVLY OFF & |
| 6 | 1 | 1 | 0 | PF OVLY OFF | RT OVLY ON | OVLY OFF * |
| 7 | 1 | 1 | 1 | RT OVLY OFF | RT OVLY ON | OVLY OFF & |

RT indicates real time image, PF is print freeze image as source.
Note: the Printer source is always real time.
 *: This mode is not to be used when the printer is displaying memory as the 9" monitor has no sync input.

&: Only modes currently used.

'NORMTERM'

This routine is the termination for the normalization parameter recall. If the normalize in progress flag (FLAG7:3) is clear then NOP else timeout after which FLAG7:3 is cleared.

'PARMGET'

This routine returns the value of a MENUNO location in R1. The location is at an address contained in PARMTBL indexed by R0. If the MENUNO address is zero then return carry set else clear.

'PARMLOAD'

This routine loads the value contained in R0 into the MENUNO location of an address contained in PARMTBL indexed by R1. If the MENUNO address is zero then NOP.

'PARMSET'

This routine modifies both MENUNO and MENLAST parameters according to a load code contained in a parameter table whose base is contained in -> R14:R15. The first table byte is the load code, the second byte the parameter.
Note: parameters 0-15 are bit (0/1), parameters 16-33 are values (0-255).

| Code | Action | |
|------|--------|---|
| 0 | No Load | Changes initiated by ID recall only. |

```
    1           Set MENUNO = MENLAST = PARM    Table Parm loaded, No
change.
    2           Set MENUNO = PARM              Table Parm loaded, Force
Change.
                Set MENLAST = /PARM
    3           Set MENLAST = MENUNO           Force No Change of Parm
already loaded.
    4           Set MENLAST = /MENUNO          Force Change of Parm already
loaded.
```

'PCONNECT'

This routine checks the DTR status of the printer. If the
printer is connected (DTR=1), the printer connected flag
(FLAG2:D3) is set. If the printer is disconnected, a print
error #12 (FLAG2:D5) is set.

'PIDCAP'

This routine loads the current Patient ID to the Print Caption
buffer (CAPTION1) at zone #0. Return is to the normal menu
after the PID is displayed (EXRTSND).

'PIDEX'

This routine displays the patient ID (PATFILE) on row #4 as
a centered overlay provided it is set ON else NOP. Entry at
PIDEX1 displays the ID unconditionally, but the Row # must be loaded.

'PIDLOAD'

This routine moves the contents of the PID/AUTO ID buffer to the
display and PID/AUTO-ID data file at row #2 and entry #0
respectively.
On entry, FPTRTEMP -> AUTOFILE or PATFILE.

'PIDOPS'

This routine enters a Patient ID in PATID into the
PID file. If the PID to be entered is all spaces or '.',
carry is returned set else clear.

Note: the routine must not be entered if the file is full.

'POFFLINE'

This routine is the print error recovery handler. If the
printer is on line (FLAG6:2=0) then NOP. Else the routine attempts first to get a good status return from the printer
and then executes an initialization cycle with values from
table PIRTBL. Only after the printer initializes without
error is the printer off-line status cleared else the process
is repeated.

'PRETURN'

This routine scans the printer SIO Input Buffer for R9
bytes. The first byte must contain 02H, the last byte 03H
(else PERR=9), the buffer empty (else PERR=1), and no receiver
errors detected (else PERR=2) and the print error flag (FLAG2:5)
is returned set. If on entry the print error flag is set, then
NOP unless the Get Status Only flag (FLAG8:1) is set. Byte
N-2 is returned as PRBYTE1 and byte N-1 as PRBYTE2.

```
            PERR = 1  No response, buffer empty
                 = 2  Receiver errors detected
                 = 9  Status return error start/stop byte
```

'PRINTERR'

This routine is the on-line print error handler. If no
print error exists (FLAG2:5=0) or the printer if off-line
(FLAG6:2=1) then NOP. If not in the main loop or not in the
normal display mode then clear print ops (POPS) but retain
print error status. If the print error is no response (PERR=1)
or buffer full (PERR=8), the printer off-line flag (FLAG6:2) is
set, a printer off-line message is displayed, the print error
flag is cleared and print ops (POPS) is reset. Other print error
codes produce a print error message. The last error code (PERR)
is saved in PRERRA.

'PRMESS'

This routine sends a message to the printer. The message is
located in the print command table at R10:R11. Values must
be loaded in PRSENDB & PRSENDB+1 if used. If the SIO printer
output buffer is full, return carry set else clear.

'PROPS'

(1)
This routine sends a single message to the printer. The status of
the printer is checked. If an error is found, the print error flag
(FLAG2:5) is set and the print error code returned in PERR. Enter
with PRCOM:PRCOM+1 -> message string to be sent and send values #1
and #2 loaded as PRSENDB:PRSENDB+1 respectively (if any). If the
print error flag is set on entry then (2). This routine is entered
each loop cycle. PRSTATUS is returned each time the status is
interrogated. If the print operation is an INQUIRE type, a print
inquire flag must be set (FLAG3:6 for 9 byte, FLAG6:0 for 10 byte) on

100 entry. These flags are cleared at exit. Inquire returns are saved in PR9RTN for the 9 byte type and either PR10RTN (FLAG6:7 set) or PRIBLEFT:PRIBLEFT+1 (FLAG6:7 clear) for the 10 byte type.

(2)
If a get status in progress flag is set (FLAG8:1) then only a get status cycle is performed.

(3)
A get printer captions cycle is initiated by entry to state #4 (POPS). This sends a preamble, then an 160 byte string from CAPTION1 (at 600 baud), then a postamble.

```
PERR = 0   no errors
     = 1   no response, buffer empty
     = 2   receiver errors detected
     = 3   abnormal execute return
     = 4   illegal execute return
     = 5   invalid execute return
     = 6   status return error
     = 7   Request while busy
     = 8   buffer full
     = 9   status return start/stop byte
     = 10  Print recovery error
     = 11  No which error response
     = 12  Printer Disconnected
```

'PRFZTERM'

This routine is entered once per loop and controls the end of the print-freeze and printing cycles.

'PUTPARM'

This routine puts a parameter contained in R1 into the last parameter buffer MENLAST whose parameter number (0-33) is contained in R0. If the parameter number is 0-15, value R1 is a bit (0/1) else a value (0-255).

'RECALLI'

This routine is a post recall ID operation. Parms are downloaded from table RECTBL and the recall in progress flag (FLAG7:2) is set. The screen is cleared and a 'set system' message with the AUTO-ID file name is displayed.

'RECALLID'

This routine either recalls the new ID system parameters (RECALLY entry) or retains the same system parameters (RECALLN entry).

'RECALLP'

This routine retrieves the system parameters of an Auto Set-up ID # = R2 from the MENUSAV buffer and installs them in MENUNO positions.

'RECTERM'

This routine is the termination for the recall ID mode.
If the recall in progress flag (FLAG7:2) is clear then NOP else timeout after which FLAG7:2 is cleared.

'REMKEY'

This routine returns a switch code corresponding to a key press from the Remote. The keypress must remain constant for two sequential entries else no change (debounce). The switch code is returned in ram variable RMSWITCH as 0-33.
(See table RSWTBLA in TABLES)

'REMSCAN'

This routine scans the remote terminal and returns RSCOL1 thru RSCOL4 corresponding to switch columns 1 thru 4. D0 thru D7 of each column corresponds to rows 0 thru 7. A one bit indicates switch closure. RCLOCK and /RSYNC are returned HI (at the connector) on exit.

'ROWCOLOR'

This routine sets the character color and row background color for each of the 8 rows. Enter with the R0 register as follows:

```
Row Background
        R0   = 0  transparent (row bkgnd off)
             = 1  black
             = 2  blue
             = 3  green
             = 4  cyan
             = 5  red
             = 6  magenta
             = 7  yellow
             = 8  white Character color
        R1   = 0  transparent (character off)
             = 1  black
             = 2  blue
             = 3  green
             = 4  cyan
             = 5  red
```

```
            = 6  magenta
            = 7  yellow
            = 8  white

Row number = R2 = 0 - 7
```

'RTCIPT'

This routine is the real time clock interrupt (500hz). Each entry, the SEC:MIN:HR registers are incremented up to 11:59:59 and then roll-over to 0:0:0. The RTC tick flag FLAG1(0) is set each second unconditionally. If the elapsed timer on flag is clear (FLAG1:6=0) then the timer registers remain unchanged.

'SBCTRL'

This routine loads the S buss output buffer as a function of register R0 as follows:

```
            R0   =0   VCR RECORD (059DH)
                 =1   VCR STOP (0598H)
                 =2   VCR REWIND (059BH)
                 =3   VCR PLAY (059AH)
                 =4   VCR STOP (0598H)
                 =5   VCR FF (059CH)
                 =6   VCR POWER-ON (05AEH)
                 =7   TV POWER-ON (00AEH)
                 =8   TV VOLUME UP (0092H)
                 =9   TV VOLUME DOWN (0093H)
                 =10  TV SELECT CAMERA LINE B (00C5H)
                 =11  TV SELECT VCR LINE A (00C0H)
                 =12  TV POWER OFF (00AFH)
                 =13  ENTRY -> SBCSPARE (TEST)
                 =14  VCR SPEED TOGGLE (05D8H)
                 =15  VCR DATA SCREEN TOGGLE (05DAH)
                 =16  VCR POWER-ON (05AEH)
                 =17  VCR POWER-OFF (05AFH)
                 =18  VCR TOGGLE ANT VTR/TV (05AAH)
                 =19  VCR TOGGLE LINE INPUT (05CFH)
                 =20  VCR MENU SELECT (05CDH)
                 =21  VCR MENU UP (05C3H)
                 =22  VCR MENU DN (05C2H)
                 =23  VCR MENU EXECUTE (05D1H)
                 =24  VCR MENU LEFT (05E2H)
                 =25  VCR MENU RIGHT (05E1H)
```

Note: the command is repeated four times.

'SBUSSGET'

This routine returns a character in register R1 from the

S buss output buffer unless the buffer is empty. If data
is available on exit, carry is returned clear else set.
If the buffer is empty before or after data is retrieved,
the E flag (buffer empry) is set. Note: not to be used
if the S buss is sending active (FLAG7:7=1).

'SBUSSIPT'

This routine is the S buss interrupt handler and is serviced
once every 0.6ms. If the S buss sending flag (FLAG7:7) is
clear then NOP else the S buss working buffer (SBUSSWB) is
shifted out to pin P35.

'SENDDAT'

This routine sends a word contained in R10:R11 to an SIO
output buffer identified by R0:

```
          R0 = 0    wand
             = 1    UU
             = 2    EXT
             = 3    printer
             = 4    Sbuss
```

Note: R10 byte is sent first.

'SENDSB'

This routine converts the contents of the S buss output buffer
into the S buss working buffer and enables transmission until
the S buss output buffer is empty. If the S buss sending flag
(FLAG7:7) is set, then the busy flag (OUTSTAT+4:D2) is set and
NOP. If the output buffer is empty then the empty flag (OUSTAT+4:D0)

is set and NOP. The routine is accessed every 4th loop to insure
frame timing requirements. Format of the S buss code in the S buss
output buffer is two bytes (12 bits) MSB:LSB.

'SIOGET'

This routine returns a character in register R1 from one of
the five SIO input buffers unless the buffer is empty. Enter with
the channel number in register R0:

```
          R0  = 0   wand
              = 1   U-U
              = 2   EXT
              = 3   printer
              = 4   keyboard
```

If data is available on exit, carry is returned clear else set.
   If the buffer is empty before or after data is retrieved, the E flag (buffer empty) is set.
Note: the IRQ3 interrupt is disabled during this routine.

'SIOINIT'

This routine initializes the five SIO channels. Format is set to table SIOX, baud rate is set to table SIOBDR and /DTR output is set to table SIOCTBL. On exit, each SIO receiver and xmitter is disabled and /RTS output is set = 1. Note: this routine must be entered only after a hardware reset (RS HI) of the 82C51 and only once per hardware reset.

'SIOIPT'

This routine polls the SIO receive interrupt (IRQ3) for a received character. A valid received character is stored in the Input buffer whose SIO received the character. If the error status is set, the X flag (rcvr error) is set, the error cleared, but the character not stored. If the Input buffer is full, the F flag (buffer full) is set, the E flag (buffer empty) is cleared, but the character not stored. The receiver SIO is cleared unconditionally.
If the buffer is full, /RTS is set hi to stop reception.

'SIOOUT'

This routine checks the first four SIO Output buffers. If any buffer is not empty, a character is sent to the corresponding SIO for transmission, the B (xmitt busy) and F (buffer full) flags are cleared provided the SIO is empty (TXE=1). If the SIO is not empty, the character is not sent and the B flag (xmit busy) flag is set. If after sending a character to the SIO, the Output buffer is empty, the E flag (buffer empty) is set.
Note that channel #5 (CBUSS) is not an SIO channel and is handled by routine CBUSSOUT.

'SIOPUT'

This routine puts a character contained in register R1 into one of the five Output buffers unless the buffer is full in which case the F flag (buffer full) is set. Enter with the SIO channel number in register R0:

```
R0  = 0   wand
    = 1   U-U
    = 2   EXT
    = 3   Printer
    = 4   Sbuss
```

If the buffer is full, carry is returned set else clear.
Interrupt IRQ3 is disabled during this routine. Note: although Cbuss is not an SIO channel, this routine is used to load it's output buffer.

'SIORXEN'

This routine enables the SIO receivers and xmitters. The /RTS pin is set LO and the receiver error flag and status INSTAT error flag (X) is cleared. Note: IRQ3 is disabled during this routine.

```
              CH 0 =    wand
                 1 =    U-U
                 2 =    EXT
                 3 =    printer
                 4 =    keyboard *
```

* Receiver section only.

'SMULT'

This routine is a single precision unsigned multiply:

R2:R3 = R2 * R3

'SMULTD'

This routine multiplies an unsigned 16 bit number (R2:R3) by an 8 bit unsigned number (R4):

R2:R3:R4 = R2:R3 * R4

'STANDBY'

This routine services the External SIO in a system standby state when FLAG11:D6 is set.

'SUERASE'

This routine moves R9 save parameter blocks in MENUSAV above file R0 such that file R0+1 then occupies the R0 file position which has then been effectively deleted.

'SUMOVE'

This routine moves all save parameter blocks in MENUSAV above block #R0 one file down such that the R0 - 1 file then occupies the R0 file position which has been effectively deleted. Note: R0 > 0 or NOP.

'SUSTORE'

This routine stores the current machine parameters in a 20 byte file in MENUSAV for entry #0. The save file consists of 2 packed bytes (MENUSAV+0, MENUSAV+1) followed by 18 bytes. The packed bytes are bit entry numbers, the 18 bytes are value numbers (MENUNO+1). A list of the MENUNO locations is located in table PARMTBL.

'SWITCHES'

This routine processes a switch code entered in R0:
```
              R0   = 0  none
                   = 1  auto iris (R+FP)
                   = 2  print (R+FP)
                   = 3  menu enter (R+FP)
                   = 4  menu down (R+FP)
                   = 5  menu up (R+FP)
                   = 6  pump start/stop     (R)
                   = 7  pump flow up (R)
                   = 8  pump flow down (R)
                   = 9  lavage (R)
                   = 10 shaver start/stop (R)
                   = 11 shaver rpm up (R)
                   = 12 shaver rpm down (R)
                   = 13 shaver mode (R)
                   = 14 vcr (R)
                   = 15 timer (R)
                   = 16 illum up (R)
                   = 17 illum down (R)
                   = 18 spare
                   = 19 wand input ready
                   = 20 keyboard BSP
                   = 21 keyboard CR
                   = 22 keyboard up
                   = 23 keyboard down
                   = 24 keyboard DEL
                   = 25 keyboard END
                   = 26 Pump pressure up
                   = 27 Pump pressure down
                   = 32 crosskey
                   = 33 remote disconnected
                   = 34 shaver upload
                   = 35 shaver download
```

'SWITCHOP'

This routine arbitrates switch requests from the front panel, remote, keyboard and wand. Simultaneous or crosskey requests result in NOP with an op error beep. An init, recall or normalize operation in progress, bypasses the keyboard and wand.

'SYNCSEL'

This routine sets the source of video sync to either the
camera (SYNCSEL=0) or the printer PRFZ (SYNCSEL=1). Enter
with carry as follows:
```
            C = 0       source = camera
              = 1       source = printer
```

'SYSINIT'

This routine is used to initialize the system for the first
time or after a catestrophic external ram failure. All of
external ram is zeroed, the normalize parameters loaded, and
a screen alignment pattern presented. SYSINIT is activated
by grounding TP2 (P31) PRIOR to system power-up. The LOGO
is transfered to CAPTIONS zone #3. The first PID and AUTO ID
files are each filled with 20 <SP> (null entry).

'TOTALIZE'

This routine is entered each second tick. If the condition
of the lamp reset switch input (P25) has changed, the lamp
elapsed time total in external ram is zeroed else it is
incremented. The system elapsed time total is incremented
unconditionally.

'UPDATE'

This routine compares the contents of the current parameter
buffer MENLAST with the corresponding parameter contents of
MENUNO. If the parameters in each buffer are not identical, the
new parameter in MENUNO is stored in MENLAST and a routine
corresponding to the parameter at an address in table EXRTBL
is executed. If the address is zero, no execution is performed.
If a routine is not executed, the next parameter is examined
until all parameters have been scanned. This routine will,
therefore, not exit until at least one routine is executed or
all parameters have been examined. If a print operation is
in progress then NOP. UPDATE is entered once per loop.
Each time a scan is completed, the update complete flag (FLAG2:7)
is set.

'UUPARMOP'

This routine controls the UU Parm upload and download. If
the shaver is off-line then NOP.

'UUPGET'

This routine retrieves and loads UUPARM upto 5 bytes from the

UU SIO Input bufffer. On the 5th input, if the 1st byte (code) is 35H and the CRC is correct, the 2 byte UU Parms are loaded into the AUTO-ID else the buffer is flushed and no load.

'VCRLOUT'

This routine displays a print busy message if the printer is printing and returns carry set else clear.

'VCRMESS'

This routine displays the VCR record or play status on Row #0 if in the Normal Page mode and the message has not yet been displayed. If not in the VCR record or play mode and the message has been displayed it is erased.

'VCRROVL'

This routine puts the captions overlay on the 20" and 9" monitors as an overlay immediately following a set of flag FLAG8:D5.

'VLIMIT'

This routine tests the value number VALNO with the contents of R1 and returns carry as :
```
                CF SET      VALNO < R1
                ZF SET      VALNO = R1
                CF CLEAR    VALNO > R1
```

'VSYNCIPT'

This routine services the video vertical sync interrupt (IRQ1). Flag FLAG1:5 is set.

'VSYNCW'

This routine waits for the vertical sync interrupt flag (FLAG1:5) and then clears it. If the flag is not set within 35ms, a jump to FATAL is executed. During the wait period, any SIO output available is sent to the SIO and housekeeping tests are performed.

'WANDC'

This routine decodes and executes the first character code (3-7) as a target zone for the data contained in WANDBUF and loads that data into the target zone. If the code = 8, then the captions are sent to the printer. If the code = 9, then the captions of zones 4 thru 7 are erased. Enter with R14:R15 -> WANDBUF and the ASCII code in R2. If the non-displayable flag (FLAG12:D2) is set then NOP.

'WANDH'

This routine scans the Wand Input SIO buffer and sets the wand data flag (FLAG4:6) when an '0DH' EOF character is found. The data (less EOF) is then transfered to a buffer in External Ram (WANDBUF) as a 20 byte data file with <SP> as fill.

'WARM'

This routine performs the initialization warm-up procedure with CBAR and message display.

'WARMSET'

This routine is set up procedures executed during the warm up operation.

APPENDIX C:

LISTING OF THE SUBROUTINES USED WITH THE
INTRA-ARTICULAR UNIT 14 SHOWING THE NESTING OF THE SUBROUTINES 1.0  COLD
        1.000 FLUSHIN0
        1.001 FLUSHIN1
        1.002 FLUSHO0
        1.003 FLUSHO1
        1.004 SIOINIT
        1.005 LD_DAC8
            1.0050 LOOPDLY
        1.006 LOADRPM
            1.0060 LD_DAC8 (1.005)

1.1 WAKE
        1.010 DISIOWRB 1.2 DREGINIT
        1.020 DISIOWRB
        1.021 DISIORD
        1.022 COLORIR
            1.0220 DISIOWRB 1.3 COLORSET
        1.030 DISIOWRB 1.4 CLS 1.5 COLORLD
        1.050 DISIOROT
        1.051 DISIOWRB 1.6 TEMPLATE
        1.060 COLORSET (1.3)
        1.061 VBOX
        1.062 VGRID
        1.063 MESS16
            1.0630 MAP16
            1.0631 CHAR16
        1.064 DISMNUM
            1.0640 BINASC
                1.06400 BINBCD
            1.0641 MAP16
            1.0642 CHAR16
        1.065 RPMLBL
            1.0650 COLORSET (1.3)
            1.0651 MESS32
                1.06510 MAP32
                1.06511 CHAR32

```
1.066 DISRPM
      1.0660 COLORSET (1.3)
      1.0661 DLNERASE
      1.0662 DISLNUM
             1.06620 BINBCD
             1.06621 BINSEG
             1.06622 VSEG
             1.06623 HSEG
      1.0663 LOOPDLY
1.067 PLABEL
      1.0670 COLORSET (1.3)
      1.0671 MESS32 (1.0651)
1.068 DISPR
      1.0680 COLORSET (1.3)
      1.0681 DLNERASE
      1.0682 DISLNUM (1.0662)
      1.0683 LOOPDLY
1.069 DISFLOW
      1.0690 COLORSET (1.3)
      1.0691 DLNERASE
      1.0692 DISLNUM (1.0062)
      1.0693 LOOPDLY
1.070 DSHWIN
1.071 WINSH
      1.0710 COLORSET (1.3)
      1.0711 WINDOW
      1.0712 MESS16 (1.063)
      1.0713 LOOPDLY
      1.0714 DISMNUM (1.064)
1.072 DPWIN
1.073 WINP
      1.0730 COLORSET (1.3)
      1.0731 WINDOW
      1.0732 MESS16 (1.063)
      1.0733 LOOPDLY
1.074 SHADOWV
      1.0740 COLORSET (1.3)
      1.0741 VLINE
1.075 PPRSET
      1.0750 COLORSET (1.3)
      1.0751 ERICON
             1.07510 LOOPDLY
      1.0752 ICON
             1.07520 LOOPDLY
1.076 DRPMSET
      1.0760 COLORSET (1.3)
      1.0761 ERICON (1.0751)
      1.0762 MUL8X16
      1.0763 DIV8
      1.0764 ICON (1.0752)
1.077 FLSET
      1.0770 COLORSET (1.3)
      1.0771 MUL8X16
```

```
            1.0772 ERICON (1.0751)
            1.0773 ICON (1.0752)
      1.078 LINEH
            1.0780 CALCDISA
            1.0781 HLINE
      1.079 LINEV
            1.0790 CALCDISA
            1.0791 VLINE
            1.0792 LDIVL
      1.080 DISBYTEW
      1.081 VMESS16
            1.0810 MAP16 (1.0630)

1.7 CALENTRY
      1.70 GZINIT
            1.700 EPIN
                  1.7000 EE_BYTER
                        1.70000 EE_WSUB
                        1.70001 EE_RSUB
                  1.7001 GENCRC
                  1.7002 FATAL
                        1.70020 COLORSET (1.3)
                        1.70021 DISMNUM (1.064)
                        1.70022 BEEP
                              1.700220 GETJUMP
      1.71 CALDIS
            1.0710 DSHWIN
      1.72 WINSH (1.071)

1.8 ENABLES

MAIN LOOP 1.10 CAL
      1.100 GETJUMP
      1.101 CALDIS (1.71)
      1.102 DSHWINTO
      1.103 EPOUT
            1.1030 GENCRC
```

```
            1.1031 EE_PAGEW
                1.10310 EE_WSUB 1.11 PRVALUE
        1.110 INTERP16
            1.1100 MUL8X16
        1.111 MUDV256
            1.1110 MUL16X16
                1.11100 MUL8X16

1.12 PRDIS 1.13 FLDIS 1.14 UUEN 1.15 UUSWITCH
        1.150 UUSIOGET
        1.151 GENCRC
        1.152 GETJUMP
        1.153 UUXCODE
        1.154 UUTVCODE
        1.155 UUNPACK
            1.1550 DPWINTO
            1.1551 FLSET (1.077)
            1.1552 DRPMSET (1.076)
            1.1553 DSHWINTO
        1.156 UUPACK
            1.1560 DIV8
            1.1561 MUL8X16

1.16 COMMERR
        1.160 FLUSHIN0
        1.161 FLUSHIN1
        1.162 DHSWINTO 1.17 REMKEY
        1.170 REMSCAN
        1.171 LOOPDLY 1.18 SWITCHOP
        1.180 GSWITCH
        1.181 FTSWITCH
        1.182 SWITCHES
            1.1820 GETJUMP
            1.1821 DPWIN
            1.1822 CALDIS (1.71)
            1.1823 DPWINTO
```

```
              1.1824 SETLBL
                  1.18240 DSHWINTO
                  1.18241 DPWINTO
              1.1825 KTIMER
              1.1826 FLSET (1.077)
              1.1827 DRPMSET (1.076)
              1.1828 PRSET (1.075)
              1.1829 DSHWINTO 1.19 CALCBARS
        1.190 MUL8X16
        1.191 DIV8

1.20 TASKER
        1.200 GETJUMP
        1.201 SHSPEED
              1.2010 LDIVL
              1.2011 TACHCOMP
        1.202 SHRPMD
        1.203 SETRPM
              1.2030 TCOR
              1.2031 TCORC
              1.2032 MUDV256
                  1.20320 MUL16X16
                      1.203200 MUL8X16
        1.204 P2SPEED
              1.2040 LDIVL
              1.2041 TACHCOMP
        1.205 SETPUMP2
              1.2050 TCOR
              1.2051 TCORC
              1.2052 MUDV256 (1.2032)
        1.206 FLVALUE
              1.2060 MUL16X16 (1.20320)
              1.2061 LDIVL
        1.207 SHSPEED
              1.2070 LDIVL
              1.2071 TACHCOMP
        1.208 SHRPMD
        1.209 SETRPM (1.203)
        1.210 P1SPEED
              1.2100 LDIVL
              1.2101 TACHCOMP
        1.211 P2SPEED (1.204)
        1.212 SETPUMP1
              1.2120 TCOR
              1.2121 TCORC
              1.2122 MUDV256 (1.2032)
```

```
        1.213 SETPUMP2 (1.205)
        1.214 PRIMTEO
              1.2140 DPWIN
              1.2141 DPWINTO
        1.215 SPOSTD
              1.2150 COLORSET (1.3)
              1.2151 CHAR8
              1.2152 MESS32 (1.0651)
        1.216 WINP (1.073)
        1.217 ADC_I
        1.218 SHSPEED (1.207)
        1.219 SHRPMD
        1.220 SETRPM (1.203)
        1.221 P2SPEED (1.204)
        1.222 SETPUMP2 (1.205)
        1.223 SHSPEED (1.207)
        1.224 SHRPMD
        1.225 SETRPM (1.203)
        1.226 P2SPEED (1.204)
        1.227 SETPUMP1 (1.212)
        1.228 SETPUMP2 (1.205)
        1.229 DLABEL
        1.230 SETTO
        1.231 DSOURCE
        1.232 DUPDATE
        1.233 WINDTO
        1.234 DPRIOR
        1.235 DISRPM (1.066)
        1.236 DISPR (1.068)
        1.237 PLABEL (1.067)
        1.238 RPMLBL (1.065)
        1.239 DISFLOW (1.069)

1.21 SETBARS
        1.210 CHNGBAR
              1.2100 DISBAR
                    1.21000 COLORSET (1.3)
                    1.21001 BAR
                    1.21002 LOOPDLY 1.22 BEEP (1.070022)

1.23 SEXECUTE
        1.230 GETJUMP
        1.231 MCTRL
        1.232 SHBRAKE
              1.2320 MCTRL
              1.2321 LOOPDLY
```

```
1.24 PEXECUTE
        1.240 GETJUMP
        1.241 MCTRL 1.25 DELAY
        1.250 EXSIO
            1.2500 EXSIOGET
            1.2501 EXSIOPUT
            1.2502 GETJUMP
        1.251 SIOOUT0
        1.252 SIOOUT1

INTERRUPTS 1.26 P1TIPT
        1.260 P2TIPT
            1.2600 P1TOVFL
            1.2601 P2TOVFL
        1.261 EXSIOIPT
            1.2610 UUSIOIPT
                1.26100 STACHIPT
                    1.261000 TACHOVFL
```

APPENDIX D:

DESCRIPTION OF THE PROGRAM USED WITH THE INTRA-ARTICULAR UNIT 14

1. MAIN ROUTINE

The following is a listing of the MAIN routine used with the intra-articular unit 14. The portions of MAIN labled MAINY, MAINO, and MAINAA are for initilization, while the portion of MAIN labled MAINB is the primary loop for the program.

```
;       Reset Vector at 0000H

JP MAINY                ;JMP TO MAIN

DS 35H

;       RST 0038H
;       Interrupt vector for /INT0, Watchdog Fail.

LD A,0                  ;FAIL CODE
                JP FATAL                ;DONE FAIL

DS 29H

;       /NMI 0066H
;       Non-maskable interrupt vector (not used).

DI
                LD A,19                 ;FAIL CODE
                JP FATAL                ;DONE FAIL

DS 20

;       0080H
;       Interrupt vector table

DW P1TIPT               ;PUMP #1 TACH IPT (/INT1)
                DW P2TIPT               ;PUMP #2 TACH IPT (/INT2)
                DW P1TOVFL              ;PUMP #1 TACH OVERFLOW
                DW P2TOVFL              ;PUMP #2 TACH OVERFLOW
                DW GMIOIPT1             ;DMA CH 0 (NOT USED)
                DW GMIOIPT2             ;DMA CH 1 (NOT USED)
                DW GMIOIPT3             ;CSIO (NOT USED)
                DW EXSIOIPT             ;EXT SIO IPT
                DW UUSIOIPT             ;U-U SIO IPT
                DW STACHIPT             ;SHAVER TACH IPT (IC)
                DW GMIOIPT5             ;OC (NOT USED)
                DW TACHOVFL             ;SHAVER TACH COUNTER OVERFLOW

DS 68H

0100H
```

```
;       Color Loader SIO CALL

MAINC:
                RET                     ;DONE

Program start

MAINY:
                DI
                LD SP,RAMTOP            ;INIT STACK POINTER
                CALL COLD               ;INIT
                CALL WAKE               ;WAKE-UP VGA
                CALL DREGINIT
                LD E,0                  ;BLUE WIPE
                CALL COLORSET
                LD D,0                  ;CLEAR MEMORY
MAINY0:
                CALL CLS                ;MEM=D
                LD IX,TCOLOR
                CALL COLORLD

CALL TEMPLATE

MAINAA:
                CALL CALENTRY           ;CK CAL ENTRY
                LD HL,LDELAYI           ;INIT LOOP DELAY
                LD (LDELAY),HL
                LD HL,0FFFFH            ;INIT MIN LOOP MEASURE
                LD (LOOPTMIN),HL
                CALL ENABLES            ;RELAY ENABLE
                EI
MAINB:
                CALL TICKX
                CALL TESTSET            ;TEST ONLY P1 & P2 SPEED SET
                CALL CASSETTE           ;CK CASSETTE
                CALL CAL                ;CALIBRATE
                CALL PRVALUE            ;GET PRESSURE VALUE
                CALL PRDIS              ;PRESSURE DISPLAY AVERAGE
                CALL FLDIS              ;FLOW DISPLAY AVERAGE
                CALL UUEN               ;CONFIGURE UU SIO
                CALL UUSWITCH           ;SELECT UU MODE
                CALL COMMERR            ;COMM ERROR HANDLER
                CALL REMKEY             ;SCAN REMOTE
                CALL SWITCHOP           ;ARBITRATE SWITCHES
                CALL CALCBARS           ;CALCULATE BARS
                CALL TASKER             ;TASK POLLER
                CALL SETBARS            ;DISPLAY BARS
                CALL BEEP               ;BEEPER
                CALL SEXECUTE           ;SHAVER MOTOR CONTROL
                CALL PEXECUTE           ;PUMP MOTOR CONTROL
                CALL DELAY              ;END OF LOOP DELAY
                JR MAINB                ;LOOP

END
```

2. DATA SECTION

The following is the data section used with the intra-articular unit 14.

```
    'DATA'

CFLAG
FLAG1           DS      1       ;(IY+0)
                                ;D0 = SPARE
                                ;D1 = HP UNATTACHED = 1
                                ;D2 = HP HAS CHANGED = 1
                                ;D3 = 28V ON = 1
                                ;D4 = DISPLAY XFR COMPLETE = 1
                                ;D5 = DISPLAY WRITE SOURCE (0 =CPU)
                                ;D6 = SPARE
                                ;D7 = SPARE

FLAG2   DS      1       ;(IY+1)
                                ;D0 = SPARE
                                ;D1 = SPARE
                                ;D2 = SHAVER TACH READY UPDATE
                                ;D3 = PUMP #1 TACH READY UPDATE
                                ;D4 = PUMP #2 TACH READY UPDATE
                                ;D5 = SHAVER IPT INHIBIT
                                ;D6 = PUMP #1 IPT INHIBIT
                                ;D7 = PUMP #2 IPT INHIBIT

FLAG3   DS      1       ;(IY+2)
                                ;D0 = CH0 (EXT) SIO RCVR ERROR
                                ;D1 = CH1 (UU) SIO RCVR ERROR
                                ;D2 = DISPLAY KEY TOGGLE
                                ;D3 = MIN/MAX TOGGLE
                                ;D4 = REQUEST FOR UPLOAD
                                ;D5 = DOWNLOAD
                                ;D6 = UU SIO ON LINE
                                ;D7 = UUEN HAS CHANGED

FLAG4   DS      1       ;(IY+3)
                                ;D0 = KEY TOGGLE
                                ;D1 = SPARE
                                ;D2 = ENABLE CH 0 ADC
                                ;D3 = ENABLE CH 1 ADC
                                ;D4 = ENABLE CH 2 ADC
                                ;D5 = ENABLE CH 3 ADC
                                ;D6 = FLOW SET MODE
                                ;D7 = PRIMING IN PROGRESS

FLAG5   DS      1       ;(IY+4)
                                ;D0 = DISPLAY RPM ENABLE
                                ;D1 = DISPLAY FLOW ENABLE
                                ;D2 = DISPLAY PRESSURE ENABLE
                                ;D3 = DISPLAY RPM LABEL ENABLE
                                ;D4 = DISPLAY SPARE ENABLE
                                ;D5 = DISPLAY PRESSURE LABEL ENABLE
                                ;D6 = DISPLAY SHAVER WINDOW ENABLE
```

```
                        ;D7 = DISPLAY PUMP WINDOW ENABLE

FLAG6       DS    1     ;(IY+5)
                        ;D0 = DISPLAY RPM REQUEST
                        ;D1 = DISPLAY FLOW REQUEST
                        ;D2 = DISPLAY PRESSURE REQUEST
                        ;D3 = DISPLAY RPM LABEL REQUEST
                        ;D4 = DISPLAY SPARE REQUEST
                        ;D5 = DISPLAY PRESSURE LABEL REQUEST
                        ;D6 = DISPLAY SHAVER WINDOW REQUEST
                        ;D7 = DISPLAY PUMP WINDOW REQUEST

FLAG7       DS    1     ;(IY+6)
                        ;D0 = SHORT BEEP REQUEST
                        ;D1 = DOUBLE BEEP REQUEST
                        ;D2 = LONG BEEP REQUEST
                        ;D3 = SPARE
                        ;D4 = TEST ONLY
                        ;D5 = KEY UP FLAG
                        ;D6 = KEY DOWN FLAG
                        ;D7 = LAVAGE IN PROGRESS

FLAG8       DS    1     ;(IY+7)
                        ;D0 = KEY TIMER AT MIN
                        ;D1 = KEY TIMER AT MAX
                        ;D2 = LIMIT SET TO TENS
                        ;D3 = SPARE
                        ;D4 = SHAVER WINDOW ALARM COLOR
                        ;D5 = PUMP WINDOW ALARM COLOR
                        ;D6 = DISPLAY SHAVER SOURCE=SET
                        ;D7 = DISPLAY PUMP SOURCE=SET

FLAG9       DS    1     ;(IY+8)
                        ;D0 = SHAVER BRAKE
                        ;D1 = SHAVER DISPLAY AVG READY
                        ;D2 = PRESSURE DISPLAY AVG READY
                        ;D3 = OSC-JOG READY
                        ;D4 = SHAVER WINDOW NUMERIC
                        ;D5 = UU SIO FORMAT/CRC ERROR
                        ;D6 = SHAVER/PUMP CAL MODE
                        ;D7 = CAL MODE IN PROGRESS

FLAG10      DS    1     ;(IY+9)
                        ;D0 = RAM READ REPEAT #0 ENABLE
                        ;D1 = RAM READ REPEAT #1 ENABLE
                        ;D2 = RAM READ REPEAT #2 ENABLE
                        ;D3 = RAM READ REPEAT #3 ENABLE
                        ;D4 = EXT SIO LOGGED ON
                        ;D5 = ENABLE EXT SIO SWITCH OPS
                        ;D6 = EXT SIO STANDBY TOGGLE (1=ON)
                        ;D7 = UU SIO EASEDROP TOGGLE (1=ON)

FLAG11      DS    1     ;(IY+10)
                        ;D0 = EEPROM DATA <> 0
                        ;D1 = PUMP CAL MODE = P2
                        ;D2 = DIGIT DISPLAY TICK

121
```

```
                                ;D3 = CASSETTE INSTALLED
                                ;D4 = DISPLAY SHAVER LABEL POST
                                ;D5 = DISPLAY PUMP LABEL POST
                                ;D6 = FLOW DISPLAY AVG READY
                                ;D7 = DISPLAY FLOW SOURCE = SET
FLAG12          DS      1       ;(IY+11)
                                ;D0 = 3/4 DIGIT FLAG (1=4 DIGITS)
                                ;D1 = COMM ERROR TOGGLE

PASAVE          DS      1       ;PORT A OUTPUT SAVE
PBSAVE          DS      1       ;PORT B OUTPUT SAVE
PCSAVE          DS      1       ;PORT C OUTPUT SAVE
PDSAVE          DS      1       ;PORT D OUTPUT SAVE
HPID            DS      1       ;HAND PIECE ID
MFAULT          DS      1       ;MOTOR FAULT = 1
                                ;D0 = SHAVER
                                ;D1 = PUMP 1
                                ;D2 = PUMP 2
TEMP1           DS      2       ;TEMPORARY
TEMP2           DS      5       ;TEMPORARY
DISBUF          DS      128     ;DISPLAY BUFFER
RPMLO           DS      2       ;RPM LO LIMIT
RPMHI           DS      2       ;RPM HI LIMIT
SIPTC           DS      1       ;SHAVER TACH IPT COUNT
OLDCOUNT        DS      4       ;SHAVER TACH OLD COUNT
MSBTACH         DS      2       ;SHAVER TACH NEW COUNT MSB
TACH            DS      4       ;SHAVER TACH COUNT BETWEEN IPTS
P1IPTC          DS      1       ;PUMP #1 TACH IPT COUNT
OLDCPT1         DS      4       ;PUMP #1 TACH OLD COUNT
MSBPT1          DS      2       ;PUMP #1 TACH NEW COUNT MSB
PTACH1          DS      4       ;PUMP #1 TACH COUNT BETWEEN IPTS
P2IPTC          DS      1       ;PUMP #2 TACH IPT COUNT
OLDCPT2         DS      4       ;PUMP #2 TACH OLD COUNT
MSBPT2          DS      2       ;PUMP #2 TACH NEW COUNT MSB
PTACH2          DS      4       ;PUMP #2 TACH COUNT BETWEEN IPTS
ADCVALUE        DS      7       ;ADC AVERAGES
                                ;+0 = ISENSE SHAVER
                                ;+1 = ISENSE PUMP 1
                                ;+2 = ISENSE PUMP 2
                                ;+3 = PUMP PRESSURE (16 BIT SIGNED VALUE)
                                ;+5/+6 = BUFFER
ACCUM           DS      9       ;ACCUMULATOR
ACCUMD          DS      13      ;ACCUMULATOR
DIGBUF          DS      6       ;DIGIT BUFFER
RSCOL1          DS      4       ;REMOTE SWITCH ARRAY (4)
RLAST           DS      1       ;REMOTE LAST SWITCH CODE
RMSWITCH        DS      1       ;REMOTE SWITCH CODE
RPMDIS          DS      2       ;DISPLAYED DIGIT RPM
RPMDISL         DS      2       ;DISPLAYED DIGIT RPM LAST
DIGDUPC         DS      1       ;DIGIT DISPLAY UPDATE COUNT
SRPMDIS         DS      1       ;DISPLAYED RPM BAR (0-199)
SMODE           DS      1       ;MODE 0=FWD,1=REV,2=OSC,3=JOG
RUNL            DS      1       ;RUN LABEL SHAVER
                                ;0=OFF
                                ;1=ON
```

```
                        ;2=SET
INBUF0      DS    11    ;CH0 SIO IN BUFFER
IB0TOP      DS    1     ;TOP OF BUFFER
OUTBUF0     DS    11    ;CH0 SIO OUT BUFFER
OB0TOP      DS    1     ;TOP OF BUFFER
INBUF1      DS    15    ;CH1 SIO IN BUFFER
IB1TOP      DS    1     ;TOP OF BUFFER
OUTBUF1     DS    11    ;CH1 SIO OUT BUFFER
OB1TOP      DS    1     ;TOP OF BUFFER
INPTRIB0    DS    2     ;CH0 SIO IN BUFFER IN PTR
OTPTRIB0    DS    2     ;CH0 SIO IN BUFFER OUT PTR
INPTROB0    DS    2     ;CH0 SIO OUT BUFFER IN PTR
OTPTROB0    DS    2     ;CH0 SIO OUT BUFFER OUT PTR
INPTRIB1    DS    2     ;CH1 SIO IN BUFFER IN PTR
OTPTRIB1    DS    2     ;CH1 SIO IN BUFFER OUT PTR
INPTROB1    DS    2     ;CH1 SIO OUT BUFFER IN PTR
OTPTROB1    DS    2     ;CH1 SIO OUT BUFFER OUT PTR
RUNP        DS    1     ;RUN LABEL PUMP
                        ;0=OFF
                        ;1=ON >>
                        ;2=ON <<
                        ;3=SET
                        ;4=PRIME
FLOWSET     DS    2     ;FLOW PRESET
FLOWSETV    DS    2     ;FLOW PRESET LAST
PUMPDIS     DS    2     ;DISPLAYED DIGIT PRESSURE
PUMPDISL    DS    2     ;DISPLAYED DIGIT PRESSURE LAST
RPMBAR      DS    1     ;SHAVER BAR RPM
PRBAR       DS    1     ;PUMP BAR PRESSURE
SHSBAR      DS    1     ;SHAVER ARROW LOAD
SHSBARL     DS    1     ;SHAVER ARROW LOAD LAST
PMPSBAR     DS    1     ;PUMP BAR PRESSURE (ARROW)
PMPSBARL    DS    1     ;PUMP BAR PRESSURE (ARROW) LAST
PRBARDIS    DS    1     ;DISPLAYED PUMP BAR PRESSURE (0-199)
SHEXCODE    DS    1     ;SHAVER RUN STATE
                        ;0=IDLE,1=RUN,2=BRAKE-REV,3=BRAKE-IDLE
SHEXL       DS    1     ;LAST SHAVER RUN STATE
PEXCODE     DS    1     ;PUMP RUN STATE
                        ;0=IDLE,1=ON NORMAL,2=ON REVERSE,3=ON LAVAGE
PHEXL       DS    1     ;LAST PUMP RUN STATE
TSTATE      DS    1     ;TASKER MACHINE STATE
SHRPM       DS    2     ;SHAVER RPM
P1RPM       DS    2     ;PUMP #1 RPM
P2RPM       DS    2     ;PUMP #2 RPM
RPMSET      DS    2     ;SHAVER RPM PRESET
PRSET       DS    1     ;PUMP PRESSURE PRESET
PRSETV      DS    1     ;PUMP PRESSURE LAST PRESET
PRSETA      DS    2     ;LAST PRESSURE SET ARROW ADDRESS
EXTRERR     DS    1     ;EXT SIO RECIEVER ERROR CODE
UURERR      DS    1     ;UU SIO RECEIVER ERROR CODE
UUCNT       DS    1     ;COUNT OF RCVD UU SIO CHARACTERS
LUUCODE     DS    1     ;LAST UU CODE RECEIVED
UUCRC       DS    2     ;UU CRC
BEEPCMND    DS    1     ;BEEP CODE
TIMC        DS    1     ;KEY TIMER TICK COUNT
TIMENC      DS    1     ;KEY TIMER ENTRY COUNT
```

```
TADDER      DS  2   ;KEY TIMER COUNT ADDER
LRPMSA      DS  2   ;LAST RPM SET ARROW ADDRESS
JOC         DS  1   ;SHAVER OSC-JOG CYCLE TIMER
SHDIR       DS  1   ;SHAVER MOTOR DIRECTION 0=FWD,1=REV)
BEEPC       DS  1   ;BEEP COUNT
BEEPT       DS  1   ;BEEP TIME
LDELAY      DS  2   ;LOOP DELAY COUNT
PMPLAST     DS  1   ;LAST PUMP LABEL
RUNLAST     DS  1   ;LAST SHAVER LABEL
SHLBTO      DS  1   ;SHAVER SET LABEL TIMEOUT
PMPLBTO     DS  1   ;PUMP SET LABEL TIMEOUT
TIMDELC     DS  1   ;KEY CHANGE DELAY COUNT
RQSTL       DS  2   ;+0=LAST DISPLAY REQUEST
                    ;+1=LAST DISPLAY ENABLE MASK
TSTAGE      DS  1   ;KEY TIMER STATE COUNTER
SHWMSG      DS  2   ;-> CURRENT SHAVER WINDOW MESSAGE
SHWMSGL     DS  2   ;-> LAST SHAVER WINDOW MESSAGE
WSHTOC      DS  1   ;SHAVER WINDOW TIME-OUT
PMPWMSG     DS  2   ;-> CURRENT PUMP WINDOW MESSAGE
PMPWMSGL    DS  2   ;-> LAST PUMP WINDOW MESSAGE
WPMPTOC     DS  1   ;PUMP WINDOW TIME-OUT
MCSAVE      DS  1   ;MOTOR CONTROL SAVE
PRDIGIT     DS  2   ;PRESSURE DIGIT DISPLAY
RPMDIGIT    DS  2   ;RPM DIGIT DISPLAY
LPCSV       DS  1   ;LAST PUMP CTRL
SBRKTC      DS  1   ;SHAVER BRAKE COUNTER
DISAVCNT    DS  1   ;SHAVER DISPLAY AVERAGE COUNT
SHAVTMP     DS  3   ;SHAVER DISPLAY AVERAGE BUFFER
SHGTR       DS  2   ;SHAVER GAIN
SHOFR       DS  2   ;SHAVER OFFSET
SHCORR      DS  2   ;SHAVER TACH CORRECTION
P1CORR      DS  2   ;PUMP #1 TACH CORRECTION
P2CORR      DS  2   ;PUMP #2 TACH CORRECTION
PCHL        DS  1   ;LAST PUMP EXECUTE CODE (TACH)
PCHLMC      DS  1   ;LAST PUMP MOTOR CODE
P1GTR       DS  2   ;PUMP #1 GAIN
P1OFR       DS  2   ;PUMP #1 OFFSET
P2GTR       DS  2   ;PUMP #2 GAIN
P2OFR       DS  2   ;PUMP #2 OFFSET
PRESS       DS  1   ;CORRECTED PRESSURE TRANSDUCER
PRMM        DS  1   ;CORRECTED PRESSURE FOR BARS
PROF        DS  2   ;PRESSURE TRANSDUCER OFFSET TERM
PROFL       DS  2   ;LAST PRESSURE OFFSET
EXBUFC      DS  4   ;EXT SIO COMMAND BUFFER
EXSWITCH    DS  1   ;EXTERNAL SIO SWITCH CMND
P1S         DS  2   ;PUMP #1 SPEED SET
P2S         DS  2   ;PUMP #2 SPEED SET
LOOPTMIN    DS  2   ;MIN LOOP DELAY
LOOPTMAX    DS  2   ;MAX LOOP DELAY
LOOPTST     DS  1   ;MIN DELAY STATE
SLAVC       DS  1   ;SHAVER LOAD AVG COUNT
SLOADAV     DS  2   ;SHAVER LOAD AVERAGE
SHNOAV      DS  2   ;# SHAVER DISPLAY AVERAGES
SHIDLY      DS  1   ;SHAVER IPT DELAY ADDER
SHWNMSG     DS  1   ;SHAVER WINDOW NUMERIC
SIOCC       DS  1   ;EXT SIO CHAR COUNT
```

```
UUFERR          DS   1    ;UU SIO FORMAT/CRC ERROR
CDLYC           DS   1    ;CALIBRATE DELAY COUNT
CPASSC          DS   1    ;CALIBRATE PASS COUNT
CALOP           DS   1    ;CAL STATE
CALSHFG         DS   1    ;CAL CORRECTION FLAG
CALP1FG         DS   1    ;CAL CORRECTION FLAG PUMP #1
CALP2FG         DS   1    ;CAL CORRECTION FLAG PUMP #2
SCELO           DS   2    ;CAL RPM ERROR LO
SCEHI           DS   2    ;CAL RPM ERROR HI
FTSW            DS   1    ;FOOT SWITCH CODE
FTSWL           DS   1    ;FOOT SWITCH LAST STATUS
FPSW            DS   1    ;FRONT PANEL SWITCH CODE
GSWL            DS   2    ;FRONT PANEL SWITCH LAST STATUS
PRMCNT          DS   1    ;PRIME TIME-OUT COUNT
CASICNT         DS   1    ;CASSETTE INSERT DELAY
PDISAV          DS   2    ;DISPLAYED PRESSURE AVERAGER
PRAVCNT         DS   1    ;DISPLAYED PRESSURE AVERAGE COUNT
FLDIGIT         DS   2    ;FLOW DISPLAY DIGIT
FLACT           DS   2    ;FLOW ACTUAL
FLACTL          DS   2    ;FLOW ACTUAL LAST
FLOW            DS   2    ;CALCULATED FLOW
FLAVCNT         DS   1    ;FLOW AVG COUNT
FLDISAV         DS   2    ;FLOW AVG BUFFER
FLSETA          DS   2    ;LAST FLOW SET ARROW
FLBAR           DS   1    ;FLOW BAR VALUE (0-180)
FLOWDIS         DS   1    ;FLOW BAR DISPLAY (0-180)
CALMD           DS   1    ;CAL MENU POINTER
UUPARM1         DS   1    ;UU PARM #1
UUPARM2         DS   1    ;UU PARM #2

STKBOT          DS   30   ;PROGRAM STACK
STK             DS   1
RAMTOP          DS   1    ;TOP OF RAM
        END
```

3. EQUATE SECTION

The following is the Equate Section used with the intra-articular unit 14.

'EQ'

This is the equate section. This module is to be used for emulation only. The microchip emulate requiring a code offset of the Port B, C. D, E and F registers 80H. This offset must be set to zero prior to code compiled for Eprom download.

```
EMUOFF          EQU   80H          ;EMULATION OFFSET
DERA            EQU   53H          ;PORT DISABLE REGISTER
ODRA            EQU   60H          ;PORT A DATA OUTPUT REGISTER
IDRA            EQU   ODRA         ;PORT A DATA INPUT REGISTER
ODRB            EQU   61H+EMUOFF   ;PORT B DATA OUTPUT REGISTER
IDRB            EQU   ODRB         ;PORT B DATA INPUT REGISTER
```

| | | | |
|---|---|---|---|
| ODRC | EQU | 62H+EMUOFF | ;PORT C DATA OUTPUT REGISTER |
| IDRC | EQU | ODRC | ;PORT C DATA INPUT REGISTER |
| ODRD | EQU | 63H+EMUOFF | ;PORT D DATA OUTPUT REGISTER |
| IDRD | EQU | ODRD | ;PORT D DATA INPUT REGISTER |
| ODRE | EQU | 64H+EMUOFF | ;PORT E DATA OUTPUT REGISTER |
| IDRE | EQU | ODRE | ;PORT E DATA INPUT REGISTER |
| ODRF | EQU | 65H+EMUOFF | ;PORT F DATA OUTPUT REGISTER |
| IDRF | EQU | ODRF | ;PORT F DATA INPUT REGISTER |
| IDRG | EQU | 66H | ;PORT G DATA INPUT REGISTER |
| DDRA | EQU | 70H | ;PORT A DIRECTION REGISTER |
| DDRB | EQU | 71H+EMUOFF | ;PORT B DIRECTION REGISTER |
| DDRC | EQU | 72H+EMUOFF | ;PORT C DIRECTION REGISTER |
| DDRD | EQU | 73H+EMUOFF | ;PORT D DIRECTION REGISTER |
| DDRE | EQU | 74H+EMUOFF | ;PORT E DIRECTION REGISTER |
| DDRF | EQU | 75H+EMUOFF | ;PORT F DIRECTION REGISTER |
| CCSRA | EQU | 50H | ;COMPARITOR CONTROL ADDRESS |
| TMDR0L | EQU | 0CH | ;PRT DATA LSB CH0 |
| TMDR0H | EQU | 0DH | ;PRT DATA MSB CH0 |
| TMDR1L | EQU | 14H | ;PRT DATA LSB CH1 |
| TMDR1H | EQU | 15H | ;PRT DATA MSB CH1 |
| RLDR0L | EQU | 0EH | ;PRT0 RELOAD LSB |
| RLDR0H | EQU | 0FH | ;PRT0 RELOAD MSB |
| RLDR1L | EQU | 16H | ;PRT1 RELOAD LSB |
| RLDR1H | EQU | 17H | ;PRT1 RELOAD MSB |
| T2FRCL | EQU | 40H | ;PRT2 COUNTER LSB |
| T2FRCH | EQU | 41H | ;PRT2 COUNTER MSB |
| T2ICRL | EQU | 46H | ;PRT2 CAPTURE LSB |
| T2ICRH | EQU | 47H | ;PRT2 CAPTURE MSB |
| T2CSR1 | EQU | 48H | ;TIMER 2 CTRL REG |
| TCR | EQU | 10H | ;PRT CONTROL ADDRESS |
| ACIA | EQU | 00H | ;ACIA REGISTER ARRAY BASE |
| CNTLA0 | EQU | 00H | ;ACIA CTRL REG A0 |
| CNTLA1 | EQU | 01H | ;ACIA CTRL REG A1 |
| CNTLB0 | EQU | 02H | ;ACIA CTRL REG B0 |
| CNTLB1 | EQU | 03H | ;ACIA CTRL REG B1 |
| STAT0 | EQU | 04H | ;ACIA STATUS REG 0 |
| STAT1 | EQU | 05H | ;ACIA STATUS REG 1 |
| TDR0 | EQU | 06H | ;ACIA XMITT DATA REG 0 |
| TDR1 | EQU | 07H | ;ACIA XMITT DATA REG 1 |
| RDR0 | EQU | 08H | ;ACIA RCVD DATA REG 0 |
| RDR1 | EQU | 09H | ;ACIA RCVD DATA REG 1 |
| ITC | EQU | 34H | ;IPT ENABLE REGISTER |
| DCNTL | EQU | 32H | ;WAIT STATE REGISTER |
| RCR | EQU | 36H | ;REFRESH CONTROL REGISTER |
| ILV | EQU | 33H | ;INTERRUPT RQST VECTOR |
| RCBAR | EQU | 3AH | ;COMMON AREA REGISTER |
| RCBR | EQU | 38H | ;COMMON BASE REGISTER |
| RBBR | EQU | 39H | ;BANK BASE REGISTER |

Program constants

| | | | |
|---|---|---|---|
| RAMSTART | EQU | 0FE00H | ;START OF RAM |
| RAMSTOP | EQU | 0FFFFH | ;END OF RAM |
| DTESTAD | EQU | 1C3BH | ;TEST BOX DISPLAY ADDRESS |
| SIPTMAX | EQU | 2 | ;SHAVER IPTS TO VALID READING |
| P1IPTMAX | EQU | 2 | ;PUMP #1 IPTS TO VALID READING |

```
P2IPTMAX     EQU    2        ;PUMP #2 IPTS TO VALID READING
SHORTBP      EQU    4        ;SHORT BEEP DURATION
LONGBP       EQU    20       ;LONG BEEP DURATION
OFFBP        EQU    20       ;OFF BEEP DURATION
LDELAYI      EQU    500      ;LOOP DELAY INIT (*100US)
PLBTOI       EQU    20       ;PUMP LABEL TIMEOUT (*.15)
SHLBTOI      EQU    20       ;SHAVER LABEL TIMEOUT (*.15)
TIMDELI      EQU    8        ;KEY MOVE TIMEOUT (*.05)
FLOWLV       EQU    800      ;LAVAGE FLOW RATE
LVGPR        EQU    10       ;LAVAGE PRESSURE
FLOWPR       EQU    100      ;PRIME FLOW SET
WSHTOI       EQU    20       ;SHAVER WINDOW TIMEOUT (*.2S)
WPMPTOI      EQU    20       ;PUMP WINDOW TIMEOUT (*.2S)
PRIMEPR      EQU    20       ;PRIMING PRESSURE
PRTIM        EQU    75       ;PRIME CYCLE TIME OUT (*.2S)
SHBKTIME     EQU    5        ;SHAVER BRAKE TIME (*100US)
SHGT         EQU    2BDH     ;SHAVER GAIN DEFAULT
SHOF         EQU    0F9H     ;SHAVER OFFSET DEFAULT
P1GT         EQU    2D0H     ;PUMP #1 GAIN DEFAULT
P1OF         EQU    0BCH     ;PUMP #1 OFFSET DEFAULT
P2GT         EQU    2D6H     ;PUMP #2 GAIN DEFAULT
P2OF         EQU    99H      ;PUMP #2 OFFSET DEFAULT
PRGF         EQU    1024     ;PRESSURE TRANSDUCER GAIN
PRIMEFL      EQU    100      ;PRIME FLOW SET
DIGDUP       EQU    8        ;DIGIT DISPLAY RATE (*.2S)
SHTCLIM      EQU    200      ;SHAVER TACH CORRECTION LIMIT
P1CLIM       EQU    200      ;PUMP #1 TACH CORRECTION LIMIT
P2CLIM       EQU    200      ;PUMP #2 TACH CORRECTION LIMIT
CPASS        EQU    6        ;CALIBRATE PASSES TO ZERO
CSETDLY      EQU    120      ;CALIBRATE SET DELAY
CASIV        EQU    -137     ;CASSETTE INSERTED THRESHOLD
CASIDLY      EQU    16       ;CASSETTE INSERT DELAY (*.05)
FLOWK        EQU    4096     ;FLOW CONVERSION CONSTANT
MINFLOW      EQU    100      ;MINIMUM SET FLOW
MAXFLOW      EQU    800      ;MAXIMUM SET FLOW
             END
```

4. TABLE SECTION

The following is the Table Section used for the intra-articular unit 14.

'TABLES'

SYMBOLS ON
CODE

```
;    SIO Initialization
;
;    First Value is Data Bit Configuration:  0 = 7DB/1SB/NP
;                               1 = 7DB/2SB/NP
;                               2 = 7DB/1SB/P
;                               3 = 7DB/2SB/P
;                               4 = 8DB/1SB/NP
;                               5 = 8DB/2SB/NP
;                               6 = 8DB/1SB/P
```

```
;                                       7 = 8DB/2SB/P
;

;       Second Value is Baud Rate:      0 = 38400
;                                       1 = 19200
;                                       2 = 9600
;                                       3 = 4800
;                                       4 = 2400
;                                       5 = 1200
;                                       6 = 600
;                                       7 = DO NOT USE
;
;       Third Value is Parity:          0 = Evern Parity
;                                       1 = Odd Parity
;
S0ITBL          DB      5               ;EXT SIO 8DB/2SB/NP
                DB      2               ;EXT SIO 9600 BAUD
                DB      0               ;EXT SIO NP
;
S1ITBL          DB      4               ;UU SIO 8DB/1SB/NP
                DB      5               ;UU SIO 1200 BAUD
                DB      0               ;UU SIO NP
;
;       Command Tables
;
;
;       Calibrate
;
CALTBL          DW      CAL0            ;IDLE
                DW      CAL1            ;SHAVER CAL ZERO
                DW      CAL2            ;SHAVER CAL GAIN
                DW      CAL3            ;SHAVER CAL CK HI
                DW      CAL4            ;SHAVER CAL CK LO
                DW      CAL5            ;PUMP #1 CAL ZERO
                DW      CAL6            ;PUMP #1 CAL GAIN
                DW      CAL7            ;PUMP #1 CAL CK HI
                DW      CAL8            ;PUMP #1 CAL CK LO
                DW      CAL9            ;PUMP #2 CAL ZERO
                DW      CAL10           ;PUMP #2 CAL GAIN
                DW      CAL11           ;PUMP #2 CAL CK HI
                DW      CAL12           ;PUMP #2 CAL CK LO
;
PRUNTBL         DW      PEX0            ;IDLE
                DW      PEX1            ;RUN NORMAL
                DW      PEX2            ;RUN REVERSE, SHAVER ON
                DW      PEX2            ;RUN REVERSE, LAVAGE
                DW      PEX1            ;RUN NORMAL, PRIME
;
```

```
BPCTBL          DW      BEEP7           ;OFF
                DW      BEEP1           ;SHORT BEEP
                DW      BEEP4           ;DOUBLE BEEP
                DW      BEEP5           ;LONG BEEP
                DW      BEEP6           ;OP ERROR
                DW      BEEP8           ;SHORT IN PROGRESS
                DW      BEEP10          ;DOUBLE IN PROGRESS ON
                DW      BEEP8           ;LONG IN PROGRESS
                DW      BEEP11          ;DOUBLE IN PROGRESS OFF
                DW      BEEP12          ;OP ERROR IN PROGRESS
                DW      BEEP14          ;OFF IN PROGRESS
;
KTIMTBL         DW      KTIM6           ;STAGE #0
                DW      KTIM8           ;STAGE #1
                DW      KTIM10          ;STAGE #2
                DW      KTIM11          ;STAGE #3
;
SRUNTBL         DW      SWE0            ;IDLE
                DW      SWE1            ;RUN
                DW      SWE2            ;BRAKE-REV
                DW      SWE3            ;BRAKE-IDLE
;
SCOMTBL         DW      SW0             ;NO SWITCHES
                DW      SW0B            ;AUTO IRIS
                DW      SW2             ;PRINT (PRIME TEMP)
                DW      SW0B            ;MENU ENTER
                DW      SW0B            ;MENU DOWN
                DW      SW0B            ;MENU UP
                DW      SW6             ;PUMP START
                DW      SW7             ;PUMP FLOW UP
                DW      SW8             ;PUMP FLOW DOWN
                DW      SW9             ;LAVAGE
                DW      SW10            ;SHAVER START
                DW      SW11            ;SHAVER RPM UP
                DW      SW12            ;SHAVER RPM DOWN
                DW      SW13            ;SHAVER MODE
                DW      SW0B            ;VCR
                DW      SW0B            ;TIMER
                DW      SW0B            ;ILLUM UP
                DW      SW0B            ;ILLUM DOWN
                DW      SW0B            ;SPARE
                DW      SW0B            ;19
                DW      SW0B            ;20
                DW      SW0B            ;21
                DW      SW0B            ;22
                DW      SW0B            ;23
                DW      SW0B            ;24
                DW      SW0B            ;25
                DW      SW26            ;PUMP PRESSURE UP
                DW      SW27            ;PUMP PRESSURE DOWN
                DW      SW28            ;PRIME ON/OFF
                DW      SW29            ;SHAVER SWITCH TO OFF
                DW      SW30            ;SHAVER SWITCH TO ON
```

```
                DW      SW0B                    ;31
                DW      SW32                    ;32
;
;       UU Switch.
;
UUCTBL          DW      UUSW1                   ;(NOT USED)
                DW      UUSW1                   ;1ST CODE BYTE
                DW      UUSW2                   ;2ND CODE BYTE
                DW      UUSW2                   ;3RD CODE BYTE
                DW      UUSW3                   ;CRC HI
                DW      UUSW4                   ;CRC LO
;
;       Tasker
;
TASKTBL         DW      TASKE2                  ;LOOP #0
                DW      TASKE3                  ;LOOP #1
                DW      TASKE5                  ;LOOP #2
                DW      TASKE6                  ;LOOP #3
;
;       External SIO
;
ESITBL          DW      EXSIO0                  ;RAM READ
                DW      EXSIO1                  ;RAM WRITE
                DW      EXSIO2                  ;I/O IN
                DW      EXSIO3                  ;I/O OUT
                DW      EXSIO4                  ;EPROM READ
                DW      EXSIO5                  ;ENABLE SW OPS
                DW      EXSIO6                  ;DISABLE SW OPS
                DW      EXSIO7                  ;LOG-ON
                DW      EXSIO8                  ;STNDBY TOGGLE
                DW      EXSIO9                  ;CALL
                DW      EXSIO10                 ;UU SIO EASEDROP
;
;       Shaver Label codes
;
SHLAB           DB      0                       ;OFF
                DB      1                       ;RUN
                DB      1                       ;BRAKE-REV
                DB      0                       ;BRAKE-IDLE
;
;       Pump Label codes
;
PMPLAB          DB      0                       ;IDLE
                DB      1                       ;RUN NORMAL
                DB      2                       ;RUN REVERSE (SHAVER ON)
                DB      2                       ;RUN REVERSE (LAVAGE)
                DB      4                       ;RUN NORMAL (PRIME)
;
;       Key timer speeds for Stages #0-6
;
KTSTBL          DB      11,10,8,8               ;*.05S

;
```

```
;       UU Switch valid codes table.
;       0 = Valid, 1= Invalid.
;
UUVCTBL         DB      0                       ;NO KEYS
                DB      1                       ;
                DB      1                       ;
                DB      1                       ;
                DB      1                       ;
                DB      1                       ;
                DB      0                       ;PUMP START/STOP
                DB      0                       ;FLOW UP
                DB      0                       ;FLOW DOWN
                DB      0                       ;LAVAGE
                DB      0                       ;SHAVER START/STOP
                DB      0                       ;SHAVER RPM UP
                DB      0                       ;SHAVER RPM DOWN
                DB      0                       ;SHAVER MODE
                DB      1                       ;
                DB      1                       ;
                DB      1                       ;
                DB      1                       ;
                DB      1                       ;
                DB      1                       ;
                DB      1                       ;
                DB      1                       ;
                DB      1                       ;
                DB      1                       ;
                DB      0                       ;PUMP PRESSURE UP
                DB      0                       ;PUMP PRESSURE DOWN
;
MLTBL           DB      'FWD$'                  ;MODE LABELS
                DB      'REV$'
                DB      'OSC$'
                DB      'JOG$'
;
MLTBLD          DB      '>>$'                   ;MODE DIRECTION
                DB      '<<$'
                DB      '<>$'
                DB      '>>$'
;
HIL             DB      'HI$'                   ;HI-MED-LO MSG
MEL             DB      'MED$'
LOL             DB      'LO$'
;
RLTBL           DB      'OFF$'                  ;RUN STATUS LABELS
                DB      ' ON$'
                DB      'SET$'
;
FLLBL           DB      'ML/MIN$'               ;FLOW LABEL
PRLBL           DB      'MMH#  $'               ;PRESSURE LABEL
;
PMLTBL          DB      'OFF  $'                ;PRESSURE MODE
                DB      'ON >>$'
                DB      'ON <<$'
```

```
                DB      'SET  $'
                DB      'PRIME$'
;
SHTIT           DB      'SHAVER$'               ;SHAVER TITLE
SHOLTIT         DB      'SHAVER OVERLOAD$'      ;SHAVER MSG
SHSRPTIT        DB      'SET RPM$'              ;SHAVER MSG
PMPTIT          DB      'PUMP$'                 ;PUMP TITLE
PSPRTIT         DB      'SET PRESSURE$'         ;PUMP MSG
PSFTIT          DB      'SET FLOW$'             ;PUMP MSG
PMGTIT          DB      'PUMP PRIMING$'         ;PUMP MSG
SHMBOTIT        DB      'SHAVER MUST BE OFF$'   ;PUMP MSG
PMBOTIT         DB      'PUMPS MUST BE OFF$'    ;PUMP MSG
LVGTIT          DB      'LAVAGE$'               ;PUMP MSG
LVGMOTIT        DB      'LAVAGE MUST BE OFF$'   ;PUMP/SHAVER MSG
CALPTIT         DB      'CALIBRATION PASS$'     ;CAL PASS
CALFTIT         DB      'CALIBRATION FAIL$'     ;CAL FAIL
CALITIT         DB      'CALIBRATION NOT DONE$' ;CAL INCOMPLETE
PRETIT          DB      'PRIMING NOT COMPLETE$' ;PUMP/SHAVER MSG
TERTIT          DB      'TERMINAL ERROR CODE$'  ;TERMINAL ERROR
PMCTIT          DB      'PRIMING COMPLETE$'     ;PRIME COMPLETE
CNITIT          DB      'NO CASSETTE$'          ;NO CASSETTE
CRMTIT          DB      'REMOVE CASSETTE$'      ;REMOVE CASSETTE
ECETIT          DB      'EXT COMM ERROR$'       ;EXT SIO ERROR
UUCETIT         DB      'UU COMM ERROR$'        ;U-U SIO ERROR
RPMMSG          DB      'RPM$'                  ;RPM
;
CALONTIT        DB      'CALIBRATING SHAVER$'   ;CAL ON TITLES
                DB      'CALIBRATING PUMP 1$'
                DB      'CALIBRATING PUMP 2$'
;
CALOFTIT        DB      'CAL SHAVER$'           ;CAL OFF TITLES
                DB      'CAL PUMP 1$'
                DB      'CAL PUMP 2$'
;
;       14 bit DAC table, 64 LSB values.
;
DAC14TBL        DB      0,4,8,12,16,20,24
                DB      28,32,36,40,44,48,52,56
                DB      60,64,68,72,76,80,84,88
                DB      92,95,99,103,107,111,115,119
                DB      123,127,131,135,139,143,147,151
                DB      155,159,162,167,171,175,179,183
                DB      187,191,195,199,203,207,211,215
                DB      219,223,227,231,235,239,243,247,251
;
;       Messages
;       Note: $ = eof, ! = ASCII FFH
;
SPTIT           DB      'SPEED$'                ;SPEED
PRTIT           DB      'PRESSURE$'             ;PRESSURE
FLTIT           DB      'FLOW$'                 ;FLOW
;
;       ADC mux address shift out byte table.
;       Byte format = xxxcbawz where x = n/c, cba = mux address
;       w = sgl/diff (=0) and z = start (=1).
;
```

```
ADCS0           DB      1H,11H,9H,19H,5,15H,0DH,1DH    ;CH0-3+,CH0-3-
;
;
;       Color register initialization values.
;       Values are decimal (0-63) for R-G-B respectively.
;       (#CB) refers to color bar #1-7 of Basic Program COLORAL.BAS
;
COLORR1         DB      0,0,0                  ;0  (#CB6)
                DB      63,63,63               ;1  (#CB7)
                DB      0,42,0                 ;2
                DB      0,42,42                ;3
                DB      42,0,0                 ;4
                DB      42,0,42                ;5
                DB      42,21,0                ;6
                DB      42,42,42               ;7
                DB      21,21,21               ;8
                DB      0,0,27                 ;9  (#CB2)
                DB      23,63,0                ;10 (#CB3)
                DB      21,63,63               ;11
                DB      63,0,0                 ;12 (#CB5)
                DB      63,21,63               ;13
                DB      63,63,63               ;14 (#CB4)
                DB      63,56,37               ;15 (#CB1)
;
;       Following are for reference only.
;
                ;DB     0,0,63                 ;16
                ;DB     16,0,63                ;17
                ;DB     31,0,63                ;18
                ;DB     47,0,63                ;19
                ;DB     63,0,63                ;20
                ;DB     63,0,47                ;21
                ;DB     63,0,31                ;22
                ;DB     63,0,16                ;23
                ;DB     63,0,0                 ;24
                ;DB     63,16,0                ;25
                ;DB     63,31,0                ;26
                ;DB     63,47,0                ;27
                ;DB     63,63,0                ;28
                ;DB     47,63,0                ;29
                ;DB     31,63,0                ;30
                ;DB     16,63,0                ;31
;
                ;DB     0,63,0                 ;32
                ;DB     0,63,16                ;33
                ;DB     0,63,31                ;34
                ;DB     0,63,47                ;35
                ;DB     0,63,63                ;36
                ;DB     0,47,63                ;37
                ;DB     0,31,63                ;38
                ;DB     0,16,63                ;39
                ;DB     31,31,63               ;40
                ;DB     39,31,63               ;41
                ;DB     47,31,63               ;42
                ;DB     55,31,63               ;43
                ;DB     63,31,63               ;44
```

```
            ;DB    63,31,55                ;45
            ;DB    63,31,47                ;46
            ;DB    63,31,39                ;47
;
            ;DB    63,31,31                ;48
            ;DB    63,39,31                ;49
            ;DB    63,47,31                ;50
            ;DB    63,55,31                ;51
            ;DB    63,63,31                ;52
            ;DB    55,63,31                ;53
            ;DB    47,63,31                ;54
            ;DB    39,63,31                ;55
            ;DB    31,63,31                ;56
            ;DB    31,63,39                ;57
            ;DB    31,63,47                ;58
            ;DB    31,63,55                ;59
            ;DB    31,63,63                ;60
            ;DB    31,55,63                ;61
            ;DB    31,47,63                ;62
            ;DB    31,39,63                ;63
;
;       VGA register initialization values.
;
DREGITBL    DB     0E3H                    ;VGA EXT MISSC
            DB     00H                     ;VGA EXT FC
;
            DB     3,1,0FH,0,6,5,0         ;SEQUENCER SR0-SR6
;
            DB     5FH,4FH,50H,82H         ;CRTC CR0-CR3
            DB     54H,80H,0BH,3EH         ;CR4-CR7
            DB     0,40H,1EH,0             ;CR8-CR11
            DB     0,0,0,0                 ;CR12-CR15
            DB     0EAH,8CH,0DFH,28H       ;CR16-CR19
            DB     0,0E7H,4,0E3H,0FFH      ;CR19-CR24
;
            DB     0,0,0,0,0,0,5,0FH,0FFH  ;GRAPHICS GR0-GR8
NCOLOR:
            DB     0,1,2,3                 ;ATTRIBUTE AR0-AR3
            DB     4,5,6,7                 ;AR4-AR7
            DB     8,9,10,11               ;AR8-AR11
            DB     12,13,14,15             ;AR12-AR15
            DB     1,12H,0FH,0,0           ;AR16-AR20

;
;       Ones address bit position mask table.
;
OMTBL           DB     0FFH         ;0
                DB     0FEH         ;1
                DB     0FCH         ;2
                DB     0F8H         ;3
                DB     0F0H         ;4
                DB     0E0H         ;5
```

```
                DB      0C0H            ;6
                DB      80H             ;7
;
;       Pixel position mask.
;
PIXOM           DB      80H             ;0
                DB      40H             ;1
                DB      20H             ;2
                DB      10H             ;3
                DB      08H             ;4
                DB      04H             ;5
                DB      02H             ;6
                DB      01H             ;7
;
;       Color code mask table.
;       First byte is data load (1/0), 2nd byte is SR2 plane enable mask
;
CMTBL           DB      0,0FH           ;0  BLUE WIPE
                DB      0FFH,0FH        ;1  WHITE WIPE
                DB      0,01H           ;2  GREEN ON WHITE
                DB      0FFH,01H        ;3  WHITE ON GREEN
                DB      0,03H           ;4  YELLOW ON WHITE
                DB      0FFH,03H        ;5  WHITE ON YELLOW
                DB      0FFH,0EH        ;6  GREEN ON BLUE
                DB      0,0EH           ;7  BLUE ON GREEN
                DB      0FFH,0CH        ;8  YELLOW ON BLUE
                DB      0,0CH           ;9  BLUE ON YELLOW
                DB      0,07H           ;10 RED ON WHITE
                DB      0FFH,07H        ;11 WHITE ON RED
                DB      0FFH,08H        ;12 RED ON BLUE
                DB      0,08H           ;13 BLUE ON RED
                DB      0,02H           ;14 BLACK ON WHITE
                DB      0FFH,02H        ;15 WHITE ON BLACK
;
;       Template pallate table.
;
TCOLOR          DB      9               ;0
                DB      1               ;1
                DB      2               ;2
                DB      3               ;3
                DB      4               ;4
                DB      5               ;5
                DB      6               ;6
                DB      7               ;7
                DB      12              ;8
                DB      9               ;9
                DB      10              ;10
                DB      11              ;11
                DB      14              ;12
                DB      0               ;13
                DB      10              ;14
                DB      15              ;15
;
;       Binary to BCD conversion table.
;
BINTBL          DB      01,00,00
```

```
            DB      02,00,00
            DB      04,00,00
            DB      08,00,00
            DB      16H,00,00
            DB      32H,00,00
            DB      64H,00,00
            DB      28H,01,00
            DB      56H,02,00
            DB      12H,05,00
            DB      24H,10H,00
            DB      48H,20H,00
            DB      96H,40H,00
            DB      92H,81H,00
            DB      84H,63H,01
            DB      68H,27H,03
;
;       Character Font table 8x8
;       21H (!) = 0FFH, 19H = Left Arrow
;
ASCII8:     DB      0,0,0,0,0,0,0,0                         ;20H, SP
            DB      0FFH,0FFH,0FFH,0FFH                     ;21H, !, FILL
            DB      0FFH,0FFH,0FFH,0FFH
            DB      0,0,0,0,0,0,0,0                         ;22H
            DB      0,78H,48H,78H,8,8,48H,78H               ;23H, #, 'g'
            DB      0,0,0,0,0,0,0,0                         ;24H
            DB      0C0H,0C8H,10H,20H,40H,98H,18H,0         ;25H,%
            DB      10H,20H,40H,0FFH,40H,20H,10H,0          ;26H, &, LEFT ARROW
            DB      0,0,0,0,0,0,0,0                         ;27H
            DB      8,10H,10H,10H,10H,10H,8,0               ;28H, (
            DB      40H,20H,20H,20H,20H,20H,40H,0           ;29H, )
            DB      0,0,0,0,0,0,0,0                         ;2AH
            DB      0,0,0,0,0,0,0,0                         ;2BH
            DB      0,0,0,0,0,0,0,0                         ;2CH
            DB      0,0,0,0F8H,0,0,0,0                      ;2DH, -
            DB      0,0,0,0,60H,60H,0,0                     ;2EH, .
            DB      0,8,10H,20H,40H,80H,0,0                 ;2FH, /
            DB      70H,88H,88H,88H,88H,88H,70H,0           ;30H, 0
            DB      20H,60H,20H,20H,20H,20H,70H,0           ;31H, 1
            DB      70H,88H,8,30H,40H,80H,0F8H,0            ;32H, 2
            DB      70H,88H,8,30H,8,88H,70H,0               ;33H, 3
            DB      10H,30H,50H,90H,F8H,10H,10H,0           ;34H, 4
            DB      0F8H,80H,0F0H,8,8,88H,70H,0             ;35H, 5
            DB      30H,40H,80H,0F0H,88H,88H,70H,0          ;36H, 6
            DB      0F8H,8,10H,20H,20H,20H,20H,0            ;37H, 7
            DB      70H,88H,88H,70H,88H,88H,70H,0           ;38H, 8
            DB      70H,88H,88H,78H,8,10H,60H,0             ;39H, 9
            DB      0,0,0,0,0,0,0,0                         ;3AH
            DB      0,0,0,0,0,0,0,0                         ;3BH
            DB      08H,10H,20H,40H,20H,10H,08H,0           ;3CH,<
            DB      0,0,0,0,0,0,0,0                         ;3DH
            DB      80H,40H,20H,10H,20H,40H,80H,0           ;3EH,>
            DB      0,0,0,0,0,0,0,0                         ;3FH
            DB      0,0,0,0,0,0,0,0                         ;40H
            DB      70H,88H,88H,0F8H,88H,88H,88H,0          ;41H, A
            DB      0F0H,88H,88H,0F0H,88H,88H,0F0H,0        ;42H, B
            DB      70H,88H,80H,80H,80H,88H,70H,0           ;43H, C
```

```
        DB      0F0H,88H,88H,88H,88H,88H,0F0H,0         ;44H, D
        DB      0F8H,80H,80H,0F0H,80H,80H,0F8H,0        ;45H, E
        DB      0F8H,80H,80H,0F0H,80H,80H,80H,0         ;46H, F
        DB      70H,88H,80H,80H,98H,88H,78H,0           ;47H, G
        DB      88H,88H,88H,0F8H,88H,88H,88H,0          ;48H, H
        DB      70H,20H,20H,20H,20H,20H,70H,0           ;49H, I
        DB      8,8,8,8,8,88H,70H,0                     ;4AH, J
        DB      88H,90H,0A0H,0C0H,0A0H,90H,88H,0        ;4BH, K
        DB      80H,80H,80H,80H,80H,80H,0F8H,0          ;4CH, L
        DB      88H,0D8H,0A8H,0A8H,88H,88H,88H,0        ;4DH, M
        DB      88H,88H,0C8H,0A8H,98H,88H,88H,0         ;4EH, N
        DB      70H,88H,88H,88H,88H,88H,70H,0           ;4FH, O
        DB      0F0H,88H,88H,0F0H,80H,80H,80H,0         ;50H, P
        DB      70H,88H,88H,88H,0A8H,90H,38H,0          ;51H, Q
        DB      0F0H,88H,88H,0F0H,0A0H,90H,88H,0        ;52H, R
        DB      70H,88H,80H,70H,8,88H,70H,0             ;53H, S
        DB      0F8H,20H,20H,20H,20H,20H,20H,0          ;54H, T
        DB      88H,88H,88H,88H,88H,88H,70H,0           ;55H, U
        DB      88H,88H,88H,50H,50H,20H,20H,0           ;56H, V
        DB      88H,88H,88H,0A8H,0A8H,0D8H,88H,0        ;57H, W
        DB      88H,88H,50H,20H,50H,88H,88H,0           ;58H, X
        DB      88H,88H,50H,20H,20H,20H,20H,0           ;59H, Y
        DB      0F8H,8,10H,20H,40H,80H,0F8H,0           ;5AH, Z
                                                        ;5BH-7FH (NOT USED)
;
;       Left arrow Icon
;
LAICON  DB      1,0,3,0,7,0,0FH,0
        DB      1FH,0,3FH,0,7FH,0FFH,0FFH,0FFH
        DB      7FH,0FFH,3FH,0,1FH,0,0FH,0
        DB      7,0,3,0,1,0,0,0
;
;       Right arrow Icon
;
RAICON  DB      0,80H,0,0C0H,0,0E0H,0,0F0H
        DB      0,0F8H,0,0FCH,0FFH,0FEH,0FFH,0FFH
        DB      0FFH,0FEH,0,0FCH,0,0F8H,0,0F0H
        DB      0,0E0H,0,0C0H,0,80H,0,0

;
;       7 segment code table (DATA load = 1)
;       Segment format 0cgfdeba
;
SEGTBL  DB      5FH,0CH,76H,7CH,2DH                     ;0-4
        DB      79H,7BH,1CH,7FH,3DH                     ;5-9
        DB      00H                                     ;SP
;
;       7 segment code table (/DATA load = 0)
;       Segment format 0cgfdeba
;
NSEGTBL DB      0A0H,0F3H,89H,83H,0D2H                  ;0-4
        DB      86H,84H,0E3H,80H,0C2H                   ;5-9
        DB      0FFH                                    ;SP
;
```

```
;       Remote Unit switch code table.
;       Arthrotek prototype.
;
RSWTBLA         DB      0,0,0,0,0,0,0,0                 ;0-7
                DB      0,7,8,10,0,2,16,5               ;8-15
                DB      0,6,9,11,12,14,1,3              ;16-23
                DB      0,26,27,13,0,15,17,4            ;24-31
                DB      32,0                            ;CROSSKEY,DISCONNECT
;
;       Switch code tables
;
FPSWTBL         DB      10,13,11,12,7,8,27,26,28        ;FRONT PANEL
;
;       Pump #1 Flow vs RPM linearization Table, 32 segments each 32 ml/min.
;
P1FTBL          DW      0
;
;       Pump #2 Zero Pressure Flow vs RPM lineariztion Table, 32 segments
;       each 32 ml/min.
;
P2FTBL          DW      0
;
;
;       Pressure Transducer Linearization Table.
;       16 segments each 16 mmHg.
;
PRLTBL          DB      0,16,32,48,64,80,96,112,128
                DB      144,160,176,192,208,224,240,255
;
                END
```

5. SUBROUTINES

The following is a description of the subroutines used with the intra-articular unit 14.

'ADC_I'

This routine acquires the converted value for the 4 analog channels of the I sense ADC and returns the values in array ADCVALUE provided the convert enable bit (IY+3) is set else NOP. Channels 0-2 are returned as positive 8 bit values, CH3 is returned as a signed 16 bit value.

'BAR'

This routine writes a horizontal segment 4 bytes wide to one of the vertical charts at a VGA left border address in HL. On entry, SR2 contains the color mask and ACCUM contains the DATA load.

'BEEP'

This routine controls the beeper as a function of beep requests in FLAG7.

```
BEEPCMND  =  0    off
          =  1    short
          =  2    double
          =  3    long
          =  4    spare
          =  5    short in progress
          =  6    double in progress on
          =  7    long in progress
          =  8    double in progress off
          =  9    spare in progress
          =  10   off in progress
```

'BINASC'

This routine converts a 16 bit unsigned binary number in DE into 5 ASCII digits returned in DIGBUF+0 thru DIGBUF+4 (lsb-msb). The numbers are leading zero suppressed.

'BINBCD'

This routine converts a 16 bit unsigned binary number in DE and returns it in ACCUMD thru ACCUMD+4 as 5 BCD numbers.

'BINSEG'

This routine converts 4 BCD digits at ACCUMD+0 thru ACCUMD+3 (lsb-msb) into 7 segment code returned in ACCUMD+0 thru ACCUMD+3 (lsb-msb) with leading zero suppression. The 7 segment code syntax:
        0cgfdeba where:
        a-e are the vertical and c-f the horizontal segments.

If the BCD number > 9999 then NOP. On entry, SR2 contains the color mask and ACCUM the DATA load.

'CAL'

This routine is the calibration mode handler if in CAL mode (IY+8:D6) else NOP.

'CALCBARS'

This routine converts the RPM Tach value SHRPM (0-4500) into
SRPMDIS (0-180), a zeroed pump pressure value PRMM (0-180mmHg),
and a flow value in FLOWDIS (0-180).

'CALCDISA'

This routine calculates a display byte and bit address given
a pixel address entered as a row in DE (0-479) and a column
in BC (0-639). The pixel address is returned as a byte
address in HL (0-38399) and a bit position (0-7) in A.

'CALDIS'

This routine displays a CAL message in the shaver window.  Enter
with CALMD and Carry as follows:

```
                      CALMD = 0 shaver
                            = 1 pump #1
                            = 2 pump #2

C     = 0 Cal
                            = 1 Calibrating
```

'CALENTRY'

This routine checks for entry into the Calibration Mode. If
PC3 (/ADCSDA)=0, the calibration mode is set (IY+8:D6=1) and
exit is delayed until release of PC3 (set Hi) else normal
operation is executed with immediate exit.

'CALSET'

This routine sets the RPM at location -> HL to a value in DE.
After CSETDLY looptimes, carry is returned set else clear.

'CASSETTE'

This routine detects the presence or absence of the Pump
cassette. If the pressure value detected is < CASIV, the
cassette is assumed absent and the cassette inserted flag
(IY+10:D3) is cleared. If the pressure is => CASIV, the
cassette is assumed present and (IY+10:D3) is set. When
a change occurrs from absent to present, the pressure
reading is stored as Pressure Zero Offset in PROF. The

140 cassette present status is measured after a CASIDLY delay
and the value must remain constant within +/- 1 count for
two consequitive entries.

'CHAR8'

This routine outputs an 8x8 ASCII character entered in ACCUM+2
to the VGA at byte address HL. Characters must reside on
byte boundries. On entry, SR2 contains the color mask and
ACCUM the DATA load. Note: ACCUM+3 must = 0 on entry.

'CHAR16'

This routine outputs an ASCII character in DISBUF to the VGA
at starting address HL. On entry, SR2 contains the color mask
and ACCUM the DATA load.

'CHAR32'

This routine outputs an ASCII character in DISBUF to the VGA
at starting address HL. On entry, SR2 contains the color mask
and ACCUM the DATA load.

'CHNGBAR'

This routine changes the Bar graph display up or down one
segment to a maximum of 180 or a minimum of zero. Enter
as follows:

```
            C = 0     down
              = 1     up

A = 0     Shaver
              = 1     Pressure
              = 2     Flow
```

'CLS'

This routine sets all enabled memory planes of display memory
to a value contained in D.

'COLD'

This routine is the cold start initialization.

141

'COLORAL'

This routine is used to change the colors in the color pallatte table to the contents of data array CLARR (0-63) at pallatte address CLARRA (0-15).

'COLORIR'

This routine loads the color registers with a 16 x 3 byte table located at (IX).

'COLORLD'

This routine loads the pallate registers AR0-AR15 with the contents of a table at -> IX. Video is disabled on entry and re-enabled on exit (ARX:D5).

'COLORSET'

This routine sets the SR2 plane enable register to a color code entered in E and returns the DATA load in ACCUM.

'COMMERR'

This routine displays a Comm Error for EXT or UU SIO. The respective Input buffer is then flushed. Note: the respective error flag is reset by the Display time-out routine WINDTO.

'DELAY'

This routine provides an end of loop delay based on variable LDELAY (*100us). On exit, LDELAY is initialized to LDELAYI.

'DISBAR'

This routine displays a bar value (0-180) contained in either RPMBAR (shaver), PRBAR (pressure) or FLBAR (flow) as a line offset in the bar given by the value. Enter as follows:

```
            C = 0    erase
              = 1    write

A = 0    Shaver
```

```
               = 1     Pressure
               = 2     Flow
```

'DISBYTER'

This routine reads a byte of data from one of the four
VGA memory planes at address 0A:B:C and returns it in
D. The plane selected is determined by the Read Map
register (GR4).

'DISBYTEW'

This routine writes a byte of data in D to one or more of
the four VGA planes at address 0A:B:C. The bit mask register
(GR8) and plane enable register (SR2) determine which planes
and which pixels respectively are written.

'DISDS'

This routine sets the set/rs enable register (GR1) of the VGA
to either write CPU or write set/rs data (GR0) to the display
memory on the next memory write cycle. Enter with the source
flag (IY+0:5) as follows:
```
               IY+0:5 = 0     CPU data
               IY+0:5 = 1     GR0 data
```

'DISFLOW'

This routine displays pump flow in FLDIGIT.
Note: the ml/min title is not displayed by this routine.
If the display enable flag (IY+4:D1) is clear then NOP else
flags (IY+4:D1) and (IY+5:D1) are cleared.

'DISIORD'

This routine reads a byte of data from the VGA I/O at address
0:03H:C (20 bits) and returns the data in D.

'DISIOROT'

This routine reads a byte of data from the VGA I/O at address
0:03H:C (20 bits) and returns the data in D. The data returned is
rotated to the right one bit and D7 is actually D0 of the
previous read.

'DISIOWRB'

This routine loads a byte of data in D into the VGA I/O at target address 0:03H:C (20 bits).

'DISLNUM'

This routine displays a 16 bit binary number in DE at VGA byte address ACCUM+3:ACCUM+2 (upper-left). On entry, SR2 contains the color mask and ACCUM contains the DATA load. The numbers are 16x32 pixels seperated by 8 pixels. If the number is >9999 then NOP. If the 3/4 digit flag (IY+11:D0) is set then 4 digits are displayed else 3 digits.

'DISMAP'

This routine downloads the display address space (A0000H-AFFFFH) with the contents of ROM data at address (xy0000H-xyFFFFH) where xy = 0-3 for one of each of the four VGA memory planes. Note: display address space A9600H-AFFFFH is not active for VGA mode 12.

'DISMASK'

This routine sets the bit position mask (GR8) to data entered in L.

'DISMNUM'

This routine displays a 16 bit binary number in DE at VGA address HL (upper-left). On entry, SR2 contains the color mask and ACCUM the DATA load. The numbers are displayed as four 16x16 pixel fields.

'DISMOVE'

This routine moves H bytes of memory from address 0AH:B:C to 0AH:D:E within the VGA display. The write mode register (GR5) must be set to mode #1. All 4 planes of memory are moved simultaneously.

'DISPR'

This routine displays pump pressure in PRDIGIT.
Note: the mmhg title is not displayed by this routine.
If the display enable flag (IY+4:D2) is clear then NOP else
flags (IY+4:D2) and (IY+5:D2) are cleared.

'DISRPM'

This routine displays the contents of RPMDIGIT as RPM. If the
display enable flag (IY+4:D0) is clear then NOP else
flags (IY+4:D0) and (IY+5:D0) are cleared.

'DIV8'

This routine divides HL by a power of 2 contained in B and
returns the rounded result in DE.

'DLABEL'

This routine sets the Shaver and/or Pump labels each time
SHEXCODE or PEXCODE changes and aborts the respective SET
time-out. The Digit Set display source flags (IY+7:D6) for
Shaver and (IY+7:D7) for Pump are cleared. The SHEXCODE change
is determined by 0 (idle) to <> 0 (<> idle) or <> 0 to 0 only.

'DLNERASE'

This routine erases a x digit field (X*32 pixels x 32 rows)
used for large number arrays. On entry, SR2 contains the
color mask and ACCUM the DATA load. The VGA start address
(upper-left) is entered in HL. If the 3/4 digit flag (IY+11:D0)
is set then x = 4 digits else x = 3 digits.

'DPRIOR'

This routine sets the Display Enable Flag register (IY+4) as
a function of the Display Request Flag register (IY+5). Requests
are serviced on a round-robin protocol until all requests have
been serviced.

'DPWIN'

This routine sets the pump window to a message at -> HL.
Any window time-out in progress is aborted, PMPWMSG and PMPWMSGL
are set to the message address. If the message is Pump Title, colors are set normal else alarm.

'DPWINTO'

This routine sets the pump window with a message at -> HL with time-out. The message -> is saved in PMPWMSG. After the timeout expires, the message -> in PMPWMSGL is re-instated. Alarm colors are set.

'DREGINIT'

This routine initializes the VGA registers to a cold start condition for Mode #12 from table DREGITBL in TABLES. The Color Register table is loaded from COLORR1 in TABLES.

'DRPMSET'

This routine sets an arrow to the bar value of RPMSET. Color is Green on Blue.

'DSHWIN'

This routine sets the shaver window to a message at -> HL. Any window time-out in progress is aborted, SHWMSG and SHWMSGL are set to the message address. If the message is Shaver Title, colors are set normal else alarm.

'DSHWINTO'

This routine sets the shaver window with a message at -> HL with time-out. The message being displayed is saved in SHWMSG. After the time-out expires, the message -> in SHWMSGL is re-instated. Alarm colors are set.

'DSOURCE'

This routine selects the source variable for the Shaver and Pump digit displays as a function of the display source flags (IY+7:D6), (IY+10:D7) and (IY+7:D7).

| flag | 0 | 1 |
|---|---|---|
| (IY+7:D6) | RPMDIS | RPMSET |
| (IY+7:D7) | PUMPDIS | PRSET |

(IY+10:D7)          FLACT          FLOWSET

If in the CAL mode, PUMPDIS is loaded as zero and RPMDIGIT
is loaded as either RPMDIS, P1RPM or P2RPM depending on
the cal selected (CALMD).

'DUPDATE'

This routine sets the display requests for Shaver RPM, Pump
pressure and flow every average ready or DIGDUP entries whichever
is longer provided the respective source flags are in the Read
Actual mode and a change has occurred from the last entry.
If the Shaver and/or Pumps are off, the reading is displayed
for any update change.

'EE_BYTER'

This routine reads a byte of EEprom data at address E and
returns it in the D register. If the EEprom does not
acknowledge, return carry set else clear. If a NACK is
retured, the EEprom must be checked by the caller.

'EE_PAGEW'

This routine writes L bytes (0<L<=8) of data starting at
Ram address (IX) into the EEprom starting at address E.
If the EEprom does not acknowledge, return carry set else
clear. The EEprom will not respond for <= 10ms following
this routine.

'EE_RSUB'

This routine reads a byte of EEprom data into D. On exit,
SCL is returned LO and SDA is returned as INPUT (HI). C must
contain PBSAVE.

'EE_WSUB'

This routine writes 8 bits contained in D into the EEprom.
It is assumed on entry that the device is started with SDA
LO and SCL HI and C is the curent state of port B. On exit,
SCL is returned LO. Carry is returned as the acknowledge bit.
SDA direction is assumed OUTPUT on entry and is OUTPUT on exit.
If a NACK is returned, the EEprom must be reset by the caller.

'ENABLES'

This routine enables the relay.

'EPIN'

This routine loads B bytes of data (8 max) from the EEprom starting at address E into ACCUMD. A CRC is performed on the data and carry returned set if invalid. The CRC must be the last 2 bytes of the data, MSB byte first.

'EPOUT'

This routine stores B bytes of data (6 max) to the EEprom at address E from ACCUMD. A CRC is generated on the data and stored at N+1 and N+2, MSB byte first, such that B+2 bytes are stored.

'ERICON'

This routine erases an icon 16 pixels wide by 16 pixels Hi at a VGA upper-left address in HL.

'EXSIO'

This routine controls external SIO access. A string sent to the Shaver is 3 bytes:
              1st   Address Lo
              2nd   Address Hi + Code
              3rd   Data The Hi address field is 4 bits (Lo nibble), the Code field is 4 bits (Hi nibble). Ram addresses are offsets into FE00H-FFFFH Ram space, Eprom Read and Calls are absolute (DATA:AL). Logon is an AAH in the data field which sets flag (IY+9:D4). If the system is not logged on, all other commands are ignored.

Codes:
              0     = ram read (0-511)
              1     = ram write (0-511)
              2     = I/O In (0-FFH)
              3     = I/O Out (0-FFH)
              4     = Eprom Read (DATA:AL)
              5     = enable switch ops (ext sio)
              6     = disable switch ops (int sio)
              7     = log on
              8     = standby toggle
              9     = Call DATA:AL
              10    = Easedrop UU SIO IN toggle

'EXSIOGET'

This routine returns a character from the EXT SIO Input buffer in the B register with carry clear unless the buffer is empty in which case carry is returned set. If a character is retrieved, /RTS0 is set LO. If the receiver error flag (IY+2:D0) is set, then carry is returned set and NOP.

'EXSIOIPT'

This routine handles the SIO CH0 (EXT) receiver interrupts. If receiver errors are found, Flag (IY+2):D0 is set and /RTS0 set HI else data is stored in the Input Buffer. If the buffer is full on exit, /RTS0 is set HI.

'EXSIOPUT'

This routine puts a character contained in A into the EXT SIO Output bufer. If the buffer is full, return carry set else clear.

'FATAL'

This is the terminal error handler. Enter with the error code in the A register.

'FLDIS'

This routine averages 16 readings of calculated flow in FLOW and then displays the average as FLACT provided the system is not in the CAL mode else NOP.

'FLSET'

This routine sets an arrow to the set value of flow FLOWSET. Color is green on blue.

'FLUSHINO'

This routine flushes the EXT SIO Input buffer, and sets /RTS0 LO.

'FLUSHIN1'

This routine flushes the UU SIO Input buffer.

'FLUSHO0'

This routine flushes the EXT SIO Output buffer.

'FLUSHO1'

This routine flushes the UU SIO Output buffer.

'FTSWITCH'

This routine acquires the foot switch status. If the foot switch is disconnected, FTSW is returned zero else FTSW is returned with the switch code provided a change of status has occurred else switch code is returned zero. If a foot switch to ON condition occurrs, the Shaver Mode is set.

```
            FTSW =  0  none or no change
                 = 29  Foot switch to OFF
                 = 30  Foot switch to ON
```

'GENCRC'

This routine generates a CRC returned at -> IX+0 for each byte entered in A.

'GSWITCH'

This routine acquires the front panel switches, HP ID and 28v status. A front panel switch code is returned in FPSW. The HP ID code is returned in HPID with flag (IY+0:D2) set if a change in HP ID status has occurred. The 28v status is returned as flag (IY+0:D3), set = 28V ON.

'GMIOIPT'

This routine is an interrupt for guarded I/O or memory. Entry at GMIOIPT1 thru GMIOIPT5 indicates an attempt to vector from an unused interrupt.

'GZINIT'

This routine loads the Shaver and Pump Tachometer calibration values as Gain and Zero parameters. If an invalid CRC is detected, a terminal error is executed. Defaults for calibration are loaded by module COLD.

'HBOX'

This routine writes a box 50 bytes wide by 80 rows tall for the horizontal charts. On entry, SR2 contains the color mask and ACCUM the DATA load. The upper-left corner is at VGA address HL.

'HLINE'

This routine draws a line A bytes long from VGA address HL
On entry, SR2 contains the data mask and ACCUM the DATA load.

'HSEG'

This routine writes a horizontal segment of 2 rows 2 bytes wide starting at VGA address HL. The segment must reside on byte boundries. On entry, SR2 contains the color mask and ACCUM contains the DATA load.

'ICON'

This routine writes an icon 16 pixels wide by 16 pixels Hi at -> IX at a VGA upper-left address in HL. The icon is contained in a table as 32 values and is written from the table left-upper to right-upper. On entry, SR2 contains the color mask and ACCUM the DATA load.

'INTERP16'

This routine performs an interpolation between points of a 16 segment table at -> IX. Enter with the X axis value (X) in E. The Y value is returned in A.

'INTERP32'

This routine performs an interpolation between points of a 32 segment table at -> IX. Enter with the X axis value (X)

in DE. The Y value is returned in HL.

'KTIMER'

If key UP (IY+6:D5=1) then count up to DE, if key DOWN
(IY+6:D6=1) then count down to DE. Count is entered and
returned in BC. Init with key release TIMC=TIMLO, TIMENC=5,
and TADDER=10. If (IY+7:D2=1) then limit at TSTAGE #1.
If BC => DE then MAX flag (IY+7:D1) is set, if BC <= DE then
MIN flag (IY+7:D0) is set.

'LD_DAC8'

This routine loads a value contained in the D register into
the octal DAC at an address in the A register (0-8). If the
address is zero then the full buffer mode is initialized for
all channels.

```
            A = 0      Init All
              = 1      Shaver MSB
              = 2      Shaver LSB
              = 3      Spare
              = 4      Spare
              = 5      Pump #1 MSB
              = 6      Pump #1 LSB
              = 7      Pump #2 MSB
              = 8      Pump #2 LSB
```

'LDIVL'

This routine is a general purpose 32 bit unsigned integer
divide utility. The 32 bit dividend is entered in accumulators
ACCUMD+3:ACCUMD+2:ACCUMD+1:ACCUMD and the 32 bit divisor is
entered in ACCUMD+11:ACCUMD+10:ACCUMD+9:ACCUMD+8. The quotient
is returned with the remainder rounded off in ACCUMD+3:ACCUMD+2:
ACCUMD+1:ACCUMD. An attempt to divide by zero returns carry set
else clear.

'LINEH'

This routine draws a horizontal line given the pixel line
address a start BC',DE' (x,y:0-639,0-479) and stop BC,DE
(x,y:0-639,0-479). The line must be on byte boundries.

'LINEV'

This routine draws a vertical line (<=255 rows) given the
line pixel address as start BC',DE' (x,y:0-639,0-479) and stop as BC,DE (x,y:0-639,0-479). The line must be on byte boundries and Ys=Ye.

'LOADRPM'

This routine loads the RPM DAC with a value DE (0-3FFFH) such that Vout = Vref*(DE/16384). Enter with the A register as follows:

A = 2    Shaver
            = 6    Pump #1
            = 8    Pump #2

'LOOPDLY'

This subroutine subtracts DE * 100us from the loop delay.

'MAP16'

This routine maps an ASCII 8x8 character in E into DISBUF as a 16x16 character. Each pixel is doubled horizontally and that row doubled vertically.

'MAP32'

This routine maps an ASCII 8x8 character in E into DISBUF as a 32x32 character. Each pixel is quadrupled horizontally and that row quadrupled vertically.

'MCTRL'

This routine controls the motor drives. Enter with the A register as follows:

| D7 | D6 | D5 | D4 | D3 | D2 | D1 | D0 |
|----|----|----|----|----|----|----|----|
| CCWP2 | RUNP2 | x | x | RUNP1 | CCWSH | BKSH | RUNSH |

1 = True

'MESS16'

This routine writes a message string terminated by an EOF = '$' located at -> (IX) starting at VGA address HL. On entry, SR2 contains the color mask and ACCUM the DATA load. The character font is 16x16.

'MESS32'

This routine writes a message string terminated by an EOF = '$' located at -> (IX) starting at VGA address HL. On entry, SR2 contains the color mask and ACCUM the DATA load. The character font is 32x32. Note: 8 characters maximum.

'MUDV256'

This routine performs the multiply-divide operation:

HL = (HL*BC)/256

'MULDIV'

This routine multiplies an 8 bit unsigned integer in A by an 8 bit unsigned integer in E and returns a rounded product in A as:
   A = (A*E)/256

'MUL8X16'

This routine multiplies an 8 bit unsigned value in A by a 16 bit unsigned value in HL returning a 24 bit product as H:L:E.

'MUL16X16'

This routine multiplies a 16 bit unsigned value in BC by a 16 bit unsigned value in HL returning a 32 bit unsigned product in H:L:B:C.

'NMIIPT'

Dick:   We need a description.

'PCHANGE'

This routine initializes the Pump Tachometers for each change of Pump motor control.

'PEXECUTE'

This routine controls the Pump motors. The operation is a function of PEXCODE:

```
PEXCODE = 0    Idle
        = 1    Run Normal
        = 2    Run Reverse (Shaver ON)
        = 3    Run Reverse (Lavage)
        = 4    Run Normal (Prime)
```

Note: Direction refers to Pump #2 only. Pump #1 is always counter clockwise.

'PLABEL'

This routine displays the pressure header as:

RUNP where:
```
RUNP = 0    OFF
     = 1    ON>>
     = 2    ON<<
     = 3    SET
     = 4    PRIME
```

If the display enable flag (IY+4:D5) is clear then NOP else flags (IY+4:D5) and (IY+5:D5) are cleared.

'PPRSET'

This routine sets an arrow to the bar value of PRSET. Color is Green on Blue.

'PRDIS'

This routine averages 16 readings of corrected pressure PRESS and then displays the average as PUMPDIS provided the system is not in the CAL mode else NOP.

'PRIMETO'

This routine times out the prime cycle.

'PRVALUE'

This routine returns a value from the pressure transducer
(PRESS) as a 16 bit signed number corrected for offset and gain.

$$PRESS = (PCOR)(PRGF)/1024$$

where:

$$PCOR = LINEAR [(ADCVALUE+3) - PROF]$$

and:

PRESS= Pressure (8 bit unsigned)
PRFG = Gain Term (1024 = x1.000)
PROF = Offset Term (16 bit signed)

'P1SPEED'

This routine converts the pump #1 tachometer count PTACH1 into
P1RPM provided the Tach Ready Flag (IY+1:D2)=1 else P1RPM = 0.
If PTACH1 > 184320 (100rpm), then P1RPM is set zero else P1RPM is
calculated as:
$$P1RPM = 18432000/PTACH1$$

Correction for interrupt latency:

$$P1RPM = P1RPM - [(P1RPM-500)/256] -2$$

'P2SPEED'

This routine converts the PUMP #2 tachometer count PTACH2 into
P2RPM provided the Tach Ready Flag (IY+1:D4)=1 else P2RPM = 0.
If PTACH2 > 184320 (100rpm), then P2RPM is set zero else P2RPM is
calculated as:
$$P2RPM = 18432000/PTACH2$$

Correction for interrupt latency:

$$P2RPM = P2RPM - [(P2RPM-500)/256] -2$$

'P1TCOR'

This routine is the digital tach servo which returns a tach
error term P1CORR:

$$P1CORR = (P1S-P1RPM)$$

and:

$$-P1CLIM < P1CORR <= +P1CLIM$$

'P2TCOR'

This routine is the digital tach servo which returns a tach error term P2CORR:

$$P2CORR = (P2S-P2RPM)$$

and:

$$-P2CLIM < P2CORR <= +P2CLIM$$

'P1TCORC'

This routine calculates the tach error for calibration mode. RPM SET - P1RPM is returned as a flag in CALP1FG.

'P2TCORC'

This routine calculates the tach error for calibration mode. RPM SET - P2RPM is returned as a flag in CALP2FG.

'P1TIPT'

This routine is the pump #1 tachometer interrupt handler (/INT1). The captured LSB count and MSBPT1 (new count) minus the last interrupt count OLDCPT1 are stored in PTACH1 (32 bits) and OLDCPT1 is set equal to the new count. RPM is K/PTACH1 where K = 18342000. Shaver interrupt count is P1IPTC is incremented each entry upto P1IPTMAX. If Flag IY+1:3 is set, PTACH1 is not updated.

'P2TIPT'

This routine is the pump #2 tachometer interrupt handler (/INT2). The captured LSB count and MSBPT2 (new count) minus the last interrupt count OLDCPT2 are stored in PTACH2 (32 bits) and OLDCPT2 is set equal to the new count. RPM is K/PTACH2 where K = 18342000. Shaver interrupt count is P2IPTC is incremented each entry upto P2IPTMAX. If Flag IY+1:4 is set, PTACH2 is not updated.

'P1TOVFL'

This routine is the pump #1 tach count overflow interrupt handler (Timer #0).

'P2TOVFL'

This routine is the pump #2 tach count overflow interrupt handler (Timer #1).

'REMCONFG'

This routine configures the Shaver for Remote Scan.

'REMKEY'

This routine returns a switch code corresponding to a key press from the Remote provided the Imager is Off-Line else NOP. The keypress must remain constant for two sequential entries (debounce) else no change. The switch code is returned in Ram variable RMSWITCH as 0-33. (see RSWTBLA in TABLES).

'REMSCAN'

This routine scans the remote terminal and returns RSCOL1 thru RSCOL4 corresponding to switch columns 1 thru 4. D0 thru D7 of each column corresponds to rows 0 thru 7. A one bit indicates switch closure. RCLOCK and RSYNC are returned HI (at the connector) on exit and must be HI on entry.

'RLYENSTB'

This routine strobes the relay enable line (/RLYEN) Lo then HI.

'RPMLBL'

This routine displays the RPM header label as:

SMODED
        SMODE where:
        SMODED = 0    >>
                   = 1    <<
                   = 2    <>
                   = 3    >>
and:
        SMODE  = 0    FWD
                   = 1    REV
                   = 2    OSC
                   = 3    JOG If the display enable flag (IY+4:D3) is clear then NOP else flags (IY+4:D3) and (IY+5:D3) are cleared and the shaver display label post flag (IY+10:D4) is set.

'SETBARS'

This routine changes the bar graphs to correspond to either SRPMDIS, PRBARDIS, or FLOWDIS (0-180).

'SETLBL'

This routine sets the Shaver and/or Pump labels for the SET mode. The currently displayed labels are saved in RUNLAST and PMPLAST and re-instated at the set time-out. The Digit source display flags (IY+7:D6) for shaver, (IY+7:D7) for pressure and (IY+10:D7) for flow are set. The set time-out is initialized. Enter with Carry as follows:

C = 0    Shaver
                  = 1    Pressure or Flow

'SETPUMP1'

This routine loads the Pump #1 DAC with a value:

DAC (0-3FFFH)=(P1GTR*P1S/256)+P1OFR+P1CORR unless the Pumps are off then DAC = 0.

Where:
- P1GTR = Gain Term (1024 = 1.000x)
- P1S = RPM (0-4000)
- P1OFR = Offset Term (signed 16 bit)
- P1CORR = Tach correction Term (signed 16 bit)

Note: P1GTR,P1CORR and P1OFR are Ram locations which must be intialized.

'SETPUMP2'

This routine loads the Pump #2 DAC with a value:

DAC (0-3FFFH)=(P2GTR*P2S/256)+P2OFR+P2CORR unless the Pumps are off then DAC = 0.

Where:
- P2GTR = Gain Term (1024 = 1.000x)
- P2S = RPM (0-4000)
- P2OFR = Offset Term (signed 16 bit)
- P2CORR = Tach correction Term (signed 16 bit)

Note: P2GTR,P2CORR and P2OFR are Ram locations which must be intialized.

'SETRPM'

This routine loads the Shaver DAC with a value:

DAC (0-3FFFH)=(SHGTR*RPMSET/256)+SHOFR+SHCORR unless the Shaver is off then DAC = 0.

Where:
- SHGTR = Gain Term (1024 = 1.000x)
- RPMSET = RPM (0-4000)
- SHOFR = Offset Term (signed 16 bit)
- SHCORR = Tach correction Term (signed 16 bit)

Note: SHGTR,SHCORR and SHOFR are Ram locations which must be intialized.

'SETTO'

This routine returns the RPM or Pressure SET label to the previous label after SHLBTO (shaver) or PMPLBTO (pump) entries. RPM SET is returned to OFF or ON, Pressure SET is returned to OFF, ON>> or ON<<.

'SEXECUTE'

This routine countrols the Shaver motor and brake operations. The operation is a function of SHEXCODE:

```
         SHEXCODE  = 0 Idle
                   = 1 Run
                   = 2 Brake-Rev (osc,jog)
                   = 3 Brake-Idle
```

'SHADOWV'

This routine shadows the vertical sides of white boxes in the template. Enter as follows:

```
            A = shadow width (bytes)
            B = shadow height (rows)
            E = pixel mask
            HL= VGA start address (left-top)
```

Shadow is dark blue on blue.

'SHBRAKE'

This routine turns the shaver OFF for then waits SHBKTIME *100us before returning.

'SHRPMD'

This routine returns the true average of X readings of SHRPM provided SIPTC = SIPTMAX (ipt ready) else NOP. The average is returned in RPMDIS with flag (IY+8:D1) set when ready. The number of averages is determined by RPMSET:

```
                <=800      4 avg
                >800       8 avg
```

'SHSPEED'

This routine converts the shaver tachometer count TACH into SHRPM provided the Tach Ready Flag (IY+1:D2)=1 else SHRPM = 0. If TACH > 921600 (100rpm), then SHRPM is set zero else SHRPM is calculated as:

$$SHRPM = 92160000/TACH$$

Correction factor for interrupt latency:

$$SHRPM = SHRPM - [(SHRPM-500)/256] -2$$

'SHTCOR'

This routine is the digital tach servo which returns a tach error term SHCORR:
$$SHCORR = (RPMSET-SHRPM)$$

and:

$$-SHTCLIM < SHCORR <= +SHTCLIM$$

'SHTCORC'

This routine calculates the tach error for calibration mode. RPM SET - SHRPM is returned as a flag in CALSHFG.

'SIO1EN'

This routine enables or disables the UU SIO and configures the Shaver for either UU SIO or Remote Scan service. Enter with the carry as follows:

```
Carry = 0 Disable
      = 1 Enable
```

'SIOOUT0'

This routine outputs the CH0 Output buffer to the SIO unless the SIO is NOT empty.

'SPOSTD'

This routine displays the shaver on-off set label provided the shaver display post flag (IY+10:D4) is set else NOP.

'SRPLANE'

This routine sets the display memory read pointer (GR4) to a plane # contained in D. During memory reads, only that plane is read.

'STACHIPT'

This routine is the shaver tachometer interrupt handler (IC). The captured LSB count and MSBTACH (new count) minus the last interrupt count OLDCOUNT are stored in TACH (32 bits) and OLDCOUNT is set equal to the new count. RPM is K/TACH where K = 92160000. Shaver interrupt count is SIPTC is incremented each entry upto SIPTMAX. If Flag IY+1:2 is set, TACH is not updated.

'STBDOG'

This routine strobes the watchdog (STBDOG) Hi then LO.

'SWITCHES'

This routine processes a switch code entered in A:

```
A   = 0  none
    = 1  auto iris (R)
    = 2  print (R)
    = 3  menu enter (R)
    = 4  menu down (R)
    = 5  menu up (R)
    = 6  pump start/stop (R)
    = 7  pump flow up (R+FP)
    = 8  pump flow down (R+FP)
    = 9  lavage (R)
    = 10 shaver start/stop (R+FP)
    = 11 shaver rpm up (R+FP)
    = 12 shaver rpm down (R+FP)
    = 13 shaver mode (R+FP)
    = 14 vcr (R)
    = 15 timer (R)
    = 16 illum up (R)
    = 17 illum down (R)
    = 18 spare
    = 26 pump pressure up (R+FP)
    = 27 pump pressure down (R+FP)
    = 28 pump prime (FP)
    = 29 shaver switch to OFF (FT)
```

```
         = 30 shaver switch to ON (FT)
         = 32 crosskey
```

'SWITCHOP'

This routine arbitrates switch requests from the front panel, shaver foot and remote controls. RMSWITCH is the remote input which is derived from the Remote scanner if the Imager is not present or from the UU SIO if the Imager is present. If the EXT switch ops flag (IY+9:D5) is set, the switch code is derived from Ram variable EXSWITCH.

'TACHOVFL'

This routine is the Shaver tachometer count overflow interrupt (16 bit PT2 overflow). The MSB of the new tach count is incremented.

'TASKER'

This routine arbitrates routines executed according to one of three loops executed sequentially (TSTATE = 0, 1,2 or 3).

'TEMPLATE'

This routine draws the template.

'UUCONFG'

This routine configures the Shaver for UUSIO.

'UUEN.'

This routine configures the Shaver for UU SIO or Remote Scan depending on the state of /UUEN. If a change from /UUEN=1 to /UUEN=0 is detected (Imager OFF to ON status), the Shaver is configured from Remote Scan to UU SIO service. If a change of /UUEN=0 to /UUEN=1 is detected (Imager ON to OFF status), the Shaver is configured from UU SIO to Remote Scan service else NOP.

'UUPACK'

This routine packs parameters UUPARM1 and UUPARM2 as follows:

F4:F3:F2:P4:P3:P2:P1:P0     UUPARM1
    F1:F0:R5:R4:R3:R2:R1:R0     UUPARM2 where:

F4:F3:F2:F1:F0 (0-31) = FLOW * 50 (0-1550ml/min)
    P4:P3:P2:P1:P0 (0-25) = PRESSURE * 10 (0-250mmHg)
    R5:R4:R3:R2:R1:R0 (0-40) = RPM * 100 (0-4000rpm)

sources are:

Pressure = PRSETV/10   (P*205/2048)
    Flow     = FLOWSETV/50 (F*41/2048)
    RPM      = RPMSET/100  (RPM*41/4096)

'UUSIOGET'

This routine returns a character from the UU SIO Input buffer in the C register with carry clear unless the buffer is empty in which case carry is returned set. If the receiver error flag (IY+2:D1) is set, then carry is returned set and NOP.

'UUSIOIPT'

This routine handles the SIO CH1 (UU) receiver interrupts. If receiver errors are found, Flag (IY+2:D1) is set else data is stored in the Input buffer. If the buffer is full on entry, then NOP. If the Imager is Off-Line then NOP.

'UUSIOPUT'

This routine puts a character contained in A into the UU SIO Output buffer. If the buffer is already full, return carry set else clear.

'UUSWITCH'

This routine unloads characters from the UU SIO Input buffer and decodes valid RMSWITCH codes which are then returned in RMSWITCH. If the UU CRC or codes are invalid, RMSWITCH is set to zero (no keys) and the Format/CRC error flag (IY+8:D5) is set. If the UU SIO is Off-Line, then the decoding process is reset. Codes 34 and 35 are special request for upload and download which execute immediate and do not affect RMSWITCH.

'UUTVCODE'

This routine tests whether a UU code byte entered in the C
register is valid. If valid return carry clear else set.

'UUXCODE'

This routine tests whether a UU code entered in the C register
is code 34 or 35. If code is 34 or 35 return carry set else clear.

'VBOX'

This routine fills a box 10 bytes wide and 180 rows tall
for the vertical charts. On entry, SR2 contains the color
mask and ACCUM the DATA load. The upper-left corner is at
VGA address HL.

'VGRID'

This routine draws 8 horizontal grid lines for the vertical
charts 8 pixels wide spaced every 20 rows. Enter with VGA
address upper-left corner in HL, SR2 containing the color
mask and ACCUM the DATA load.

'VLINE'

This routine draws a vertical line B bytes tall at VGA address
ACCUM+3:ACCUM+2. On entry, E is the pixel mask, SR2 contains
the color mask and ACCUM contains the DATA load.

'VMESS16'

This routine writes a message string terminated by an EOF = '$'
located at -> (IX) starting at VGA address HL. On entry, SR2
contains the color mask and ACCUM the DATA load. The character
font is 16x16. The message is written vertically from the start
address.

'VSEG'

This routine writes a vertical segment of a pixel map
contained in E 16 rows tall starting at VGA address ACCUM+3:ACCUM+2.
On entry, SR2 contains the color mask and ACCUM the DATA load.

'WAKE'

This routine wakes up the VGA card:

```
1EH to 46E8H    Enter Set-up
01H to 0302H    Global Enable
0EH to 46E8H    Exit Set-up
```

'WINDOW'

This routine creates a window of ACCUM+2 * 2 bytes x B rows.
On entry, SR2 contains the color mask and ACCUM the DATA load.
The VGA start address (upper-left) is entered in HL.

'WINP'

This routine creates a window at starting address -> 4F33H with
a message at -> PMPWMSG. The window size is 2 characters (32 pixels)
larger than the message. The window is yellow in the Pump section.
If flag (IY+D5=1) then color is white on red.

'WINDTO'

This routine is the message time-out for the shaver and pump
windows. After WSHTOC and/or WPMPTOC turn zero, the last
messages at -> SHWMSGL and -> PMPWMSGL are restored. If
the last message was 'SHAVER' or 'PUMP', alarm colors are
set normal.

What is claimed is:

1. An apparatus for performing endoscopic surgical procedures within an internal body cavity, said apparatus comprising:

imaging means for viewing said internal body cavity in response to operating parameters which define at least one operational characteristic of said imaging means for controlling said viewing, said imaging means including camera means for generating optical signals of said internal body cavity;

intra-articular means for controlling irrigation within said internal body cavity in response to said operating parameters which define at least one operational characteristic of said intra-articular means for controlling irrigation, said intra-articular means including pumping means for providing a flow of fluid into said internal body cavity and for withdrawing fluid from said internal body cavity;

means for allowing electrical intercommunication between said imaging means and said intra-articular means;

auto setup means for retrieving existing operating parameters and storing new operating parameters, said auto setup means associates different operating parameters with different users, wherein said operating parameters are associated with a user by means of a name identifying said user and recalled by said user by said name to set said operational characteristics of said imaging means and said intra-articular means in response to said operating parameters recalled by said user; and whereby the operation of said imaging means and said intra-articular means can be easily set to different operating parameters recalled by the different users.

2. The apparatus according to claim 1, further comprising a remote control unit for controlling the operation of said imaging means from a region proximate to said internal body cavity.

3. The apparatus according to claim 2, wherein said remote control unit is further operable to control the operation of said intra-articular means.

4. The apparatus according to claim 2, wherein said remote control unit is autoclavable and operable to be used in a sterile operating field.

5. The apparatus according to claim 2, further comprising a video printer electrically communicating with said imaging means, said remote control unit being further operable to control the operation of said video printer.

6. The apparatus according to claim 2, further comprising a video cassette recorder electrically communicating with said imaging means, said remote control unit being further operable to control the operation of said video cassette recorder.

7. The apparatus according to claim 1, wherein said means for allowing electrical communication between said imaging means and said intra-articular means includes means for receiving said imaging means and said intra-articular means, said means for receiving said imaging means and said intra-articular means including an electrical bus being operable to cause electrical intercommunication between said imaging means and said intra-articular means.

8. The apparatus according to claim 1, wherein said imaging means further includes a camera and a light source, said imaging means being operable to automatically white balance said camera with respect to said light source.

9. The apparatus according to claim 1, wherein said apparatus further includes a shaver handpiece, said intra-articular means being operable to control the flow of fluid into and withdrawn from said internal body cavity at least partially in response to the activation of said shaver handpiece.

10. An apparatus for use in performing endoscopic surgical procedures within an internal body cavity, said apparatus comprising:

an imaging unit for viewing said internal body cavity, said imaging unit including:
(a) a first chassis,
(b) a video camera disposed within said first chassis,
(c) a light source disposed within said first chassis,
wherein said imaging unit is responsive to operating parameters which define at least one operational characteristic of said imaging unit;

a camera head tethered to said first chassis and being operable to deliver light from said light source to said internal body cavity and to allow said video camera to receive images from said internal body cavity;

an intra-articular unit for controlling irrigation within said internal body cavity and operating interdependently with said imaging unit, said intra-articular unit including:
(a) a second chassis,
(b) a pumping unit disposed within said second chassis,
(c) a cassette adapted to be inserted into said pumping unit and being operable to deliver and withdraw fluid from said internal body cavity,
(d) a shaver power unit disposed within said second chassis, wherein said intra-articular unit is responsive to said operating parameters which define at least one operational characteristic of said intra-articular unit;

auto setup means for retrieving existing operating parameters and storing new operating parameters, said auto setup means associates different operating parameters with different users, wherein said operating parameters are associated with a user by means of a name identifying said user and recalled by said user by said name to set said operational characteristics of said imaging unit and said intra-articular unit upon recalling said operating parameters by said user;

a shaver handpiece tethered to said second chassis and being operable to allow endoscopic surgical procedures to be performed within said internal body cavity, said shaver handpiece being in electrical communication with said shaver power unit;

a cart for receiving said imaging unit and said intra-articular unit and for allowing electrical communication therebetween; and a remote control unit for controlling both said imaging unit and said intra-articular unit.

11. The apparatus of claim 10, wherein said imaging unit includes means for automatically white balancing said video camera with respect to said light source.

12. The apparatus of claim 11, wherein said intra-articular unit is operable to control the delivery and withdrawal of fluid from said internal body cavity at least partially in response to the activation of said shaver power unit.

13. The apparatus of claim 12, further comprising a video printer and a video cassette recorder for recording the output of said video camera, said video printer and said video cassette recorder being controlled by said remote control unit.

14. The apparatus of claim 13, wherein said remote control unit is autoclavable so as to be operable to be used in a sterile operating field.

15. The apparatus of claim 14, further comprising a keyboard for inputing information into said apparatus.

16. The apparatus of claim 15, further comprising a bar code wand for imputing information into said apparatus.

17. An apparatus for performing endoscopic surgical procedures within an internal body cavity, said apparatus comprising:

an imaging unit operable to view said internal body cavity, said imaging unit being responsive to operating parameters which define at least one operational characteristic of said imaging unit;

an intra-articular unit operable to control irrigation within said internal body cavity, said intra-articular unit being responsive to said operating parameters which define at least one operational characteristic of said intra-articular unit;

electrical conductors coupled to said imaging unit and said intra-articular unit, said electrical conductors allow said imaging unit to communicate with said intra-articular unit; and auto setup means for retrieving existing operating parameters and storing new operating parameters, said auto setup means associates different operating parameters with different users, wherein said operating parameters are stored and associated with a user by means of a name identifying said user and recalled by said user by said name, whereby said imaging unit and said intra-articular unit are set to said operating parameters recalled by said user by said name to control the operational characteristics of said imaging unit and said intra-articular unit.

18. The apparatus of claim 17, wherein said at least one operational characteristic of said imaging unit is selected from the group consisting of white balance, iris contrast and auto gain.

19. The apparatus of claim 17, wherein said at least one operational characteristic of said intra-articular unit is selected from the group consisting of flow rate and cavity pressure.

20. The apparatus of claim 17, wherein said auto setup means is menu-driven.

* * * * *